(12) United States Patent
Golding, Jr. et al.

(10) Patent No.: US 10,344,470 B2
(45) Date of Patent: *Jul. 9, 2019

(54) INTEGRATED WATERPROOFING AND DRAINAGE SYSTEM WITH INTRINSIC LEAK DETECTION FOR BUILDING STRUCTURES AND METHODS OF USE

(71) Applicant: BuildTech Solutions LLC, Hamburg, NY (US)

(72) Inventors: Aaron W. Golding, Jr., Derby, NY (US); George S. Baggs, Hamburg, NY (US)

(73) Assignee: BuildTech Solutions LLC, Hamburg, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/709,980

(22) Filed: Sep. 20, 2017

(65) Prior Publication Data

US 2018/0010329 A1    Jan. 11, 2018

Related U.S. Application Data

(63) Continuation-in-part of application No. 14/958,124, filed on Dec. 3, 2015, now Pat. No. 9,771,703.
(Continued)

(51) Int. Cl.
*E04B 1/66* (2006.01)
*G01M 3/04* (2006.01)
(Continued)

(52) U.S. Cl.
CPC .............. *E04B 1/665* (2013.01); *B32B 3/02* (2013.01); *B32B 3/18* (2013.01); *B32B 3/266* (2013.01); *B32B 3/30* (2013.01); *B32B 5/02* (2013.01); *B32B 5/022* (2013.01); *B32B 5/26* (2013.01); *B32B 7/06* (2013.01); *B32B 7/08* (2013.01); *B32B 7/12* (2013.01); *B32B 7/14* (2013.01); *B32B 11/06* (2013.01); *B32B 11/08* (2013.01);
(Continued)

(58) Field of Classification Search
CPC ......... B32B 7/12; B32B 5/02; B32B 2607/00; B32B 2307/73; B32B 2395/00; E04B 1/665; G01M 3/16; G01M 3/045; G01M 3/40; E02D 31/025; E02D 2600/10; E02D 31/06; G01N 27/221
See application file for complete search history.

(56) References Cited

U.S. PATENT DOCUMENTS 3,186,896 A    6/1965 Clem
3,445,322 A    5/1969 Saiia et al.
(Continued)

OTHER PUBLICATIONS

Polyguard's 650 Membrane Product Data Sheet for sheet waterproofing membrane; published prior to Apr. 15, 2015; five pages.
(Continued)

*Primary Examiner* — Adriana Figueroa
(74) *Attorney, Agent, or Firm* — Terrence M. Wyles, Esq.; Startup IP Law, LLC

(57) ABSTRACT

The inventive disclosures are directed to a factory-controlled process for making improved, risk-optimized commercial-building waterproofing systems. The improved waterproofing-panel systems also include improved intrinsic leak-detection capabilities.

20 Claims, 22 Drawing Sheets

Related U.S. Application Data

(60) Provisional application No. 62/148,312, filed on Apr. 16, 2015.

(51) Int. Cl.

| | | |
|---|---|---|
| *G01M 3/16* | (2006.01) | |
| *E02D 31/02* | (2006.01) | |
| *B32B 5/02* | (2006.01) | |
| *B32B 7/12* | (2006.01) | |
| *E04C 2/52* | (2006.01) | |
| *G01N 27/22* | (2006.01) | |
| *G01N 27/24* | (2006.01) | |
| *B32B 5/26* | (2006.01) | |
| *B32B 7/06* | (2019.01) | |
| *B32B 7/08* | (2019.01) | |
| *B32B 7/14* | (2006.01) | |
| *B32B 11/06* | (2006.01) | |
| *B32B 11/08* | (2006.01) | |
| *B32B 11/10* | (2006.01) | |
| *B32B 15/02* | (2006.01) | |
| *B32B 15/085* | (2006.01) | |
| *B32B 15/18* | (2006.01) | |
| *B32B 15/20* | (2006.01) | |
| *B32B 27/12* | (2006.01) | |
| *B32B 27/30* | (2006.01) | |
| *B32B 27/32* | (2006.01) | |
| *B32B 3/02* | (2006.01) | |
| *B32B 3/18* | (2006.01) | |
| *B32B 3/26* | (2006.01) | |
| *B32B 3/30* | (2006.01) | |
| *G01N 27/04* | (2006.01) | |
| *G01N 27/20* | (2006.01) | |

(52) U.S. Cl.
CPC .............. *B32B 11/10* (2013.01); *B32B 15/02* (2013.01); *B32B 15/085* (2013.01); *B32B 15/18* (2013.01); *B32B 15/20* (2013.01); *B32B 27/12* (2013.01); *B32B 27/302* (2013.01); *B32B 27/32* (2013.01); *E02D 31/025* (2013.01); *E04C 2/528* (2013.01); *G01M 3/045* (2013.01); *G01M 3/16* (2013.01); *G01N 27/223* (2013.01); *G01N 27/24* (2013.01); *B32B 2260/02* (2013.01); *B32B 2260/046* (2013.01); *B32B 2262/0253* (2013.01); *B32B 2307/202* (2013.01); *B32B 2307/50* (2013.01); *B32B 2307/554* (2013.01); *B32B 2307/7145* (2013.01); *B32B 2307/73* (2013.01); *B32B 2307/732* (2013.01); *B32B 2307/748* (2013.01); *B32B 2395/00* (2013.01); *B32B 2419/00* (2013.01); *B32B 2607/00* (2013.01); *E02D 2600/10* (2013.01); *G01N 27/048* (2013.01); *G01N 27/20* (2013.01)

(56) References Cited

U.S. PATENT DOCUMENTS

| | | |
|---|---|---|
| 3,654,765 A | 4/1972 | Healy et al. |
| 3,888,087 A | 6/1975 | Bergland |
| 4,404,516 A | 9/1983 | Johnson |
| 4,467,015 A | 8/1984 | Clem |
| 4,490,072 A | 12/1984 | Glasser |
| 4,574,541 A | 3/1986 | Raidt et al. |
| 4,704,048 A | 11/1987 | Ahlgrimm |
| 4,720,669 A | 1/1988 | Owen |
| 4,725,785 A | 2/1988 | Converse et al. |
| 4,730,953 A | 3/1988 | Tarko |
| 4,740,757 A | 4/1988 | Converse et al. |
| 4,751,467 A | 6/1988 | Cooper |
| 4,840,515 A | 6/1989 | Freese |
| 4,897,313 A | 1/1990 | Wiercinski |
| 4,943,185 A | 7/1990 | McGuckin et al. |
| 5,081,422 A | 1/1992 | Shih |
| 5,184,083 A | 2/1993 | Groover |
| 5,263,792 A | 11/1993 | Davis et al. |
| 5,288,168 A | 2/1994 | Spencer |
| 5,463,377 A | 10/1995 | Kronberg |
| 5,540,085 A | 7/1996 | Sakata et al. |
| 5,763,036 A | 6/1998 | Terry et al. |
| 5,850,144 A | 12/1998 | Howells et al. |
| 6,331,778 B1 | 12/2001 | Daily et al. |
| 7,292,155 B2 | 11/2007 | Vokey et al. |
| 7,488,523 B1 | 2/2009 | Muncaster et al. |
| 7,686,903 B2 | 3/2010 | Muncaster et al. |
| 7,872,479 B2 | 1/2011 | Lorenz et al. |
| 8,039,081 B2 | 10/2011 | Ianniello et al. |
| 8,291,668 B2 * | 10/2012 | Iske |
| 8,319,508 B2 | 11/2012 | Vokey |
| 8,566,051 B2 | 10/2013 | Gunness |
| 9,157,828 B2 | 10/2015 | Jaman et al. |
| 9,244,030 B2 | 1/2016 | Vokey et al. |
| 9,341,540 B2 * | 5/2016 | Gunness |
| 2009/0044595 A1 | 2/2009 | Vokey |
| 2010/0141281 A1 * | 6/2010 | Johnsen |
| 2012/0074967 A1 | 3/2012 | Vokey et al. |
| 2014/0049247 A1 | 2/2014 | Gunness |
| 2014/0361796 A1 | 12/2014 | Vokey et al. |

OTHER PUBLICATIONS

Caplinq's Technical Data Sheet for LINQSTAT XVCF-Series, published Jul. 2014; four pages.
National Instruments' data sheet for 6-½-Digit Digital Multimeter, 1.8 MS/s Isolated Digitizer, and LCR Meter, published in 2007; five pages.
The Concrete Society—electrical conductivity webpage; published prior to Apr. 15, 2015; one page.
Military Handbook: Grounding, Bonding, and Shielding for Electronic Equipments and Facilities vols. 1 and 2 of Two Volumes, basic theory, Dec. 1987; 812 pages.
Grace Waterproofing System's data sheet for Bituthene 6000 EIM, published 2014; two pages.
Melexis Microelectroni Integrated Systems data sheet for MLX90129, published 2012; 60 pages.

* cited by examiner

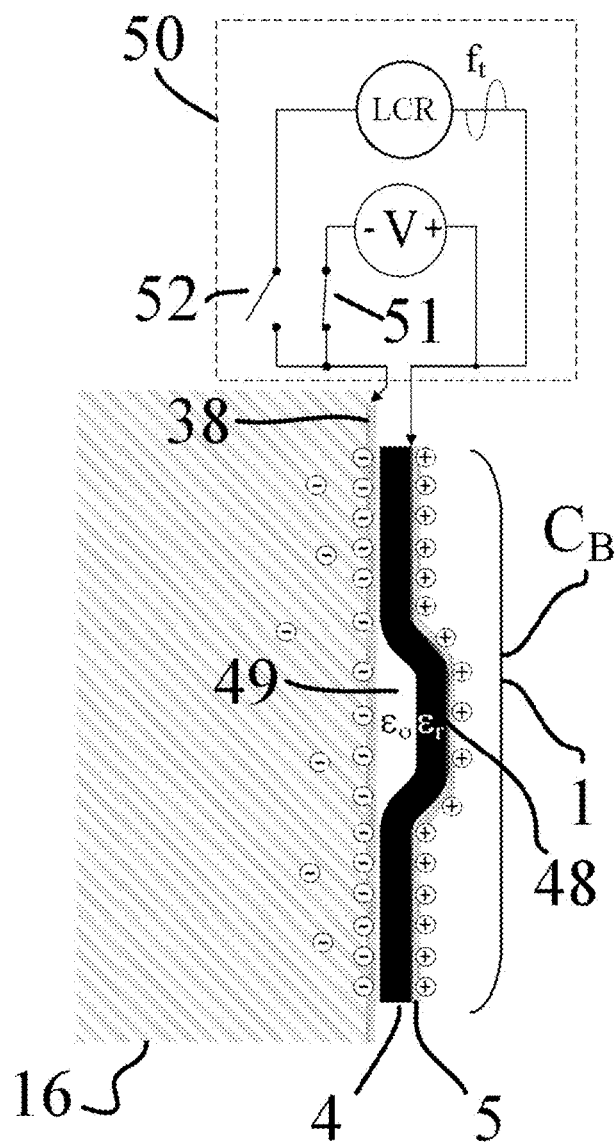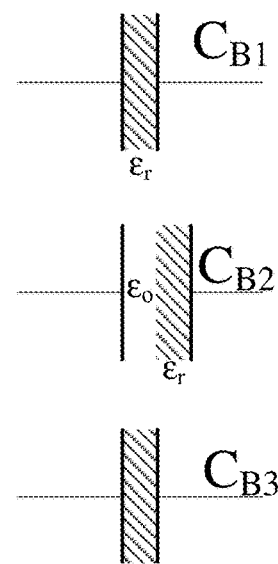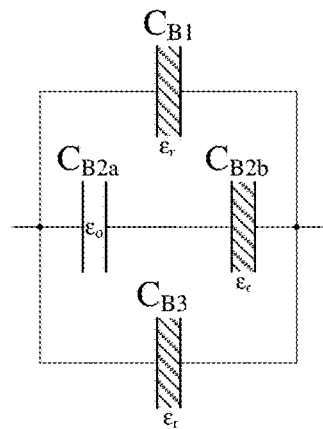
FIG. 11A
FIG. 11B
FIG. 11C

INTEGRATED WATERPROOFING AND DRAINAGE SYSTEM WITH INTRINSIC LEAK DETECTION FOR BUILDING STRUCTURES AND METHODS OF USE

CROSS-REFERENCE TO RELATED APPLICATIONS

This patent application is a Continuation-in-Part of, and claims the priority benefit of U.S. patent application Ser. No. 14/958,124, filed on Dec. 3, 2015 for "Integrated Waterproofing and Drainage System With Intrinsic Leak Detection", which was issued a Notice of Allowance on May 30, 2017, and which also claims the priority benefit of U.S. Provisional Patent Application No. 62/148,312, filed on Apr. 16, 2015 for "Integrated Waterproofing and Drainage System With Intrinsic Leak Detection". In addition, this patent application hereby incorporates by reference U.S. patent application Ser. No. 14/958,124 and U.S. Provisional Patent Application No. 62/148,312 for all purposes. If there are any irreconcilable conflicts between this patent application and the disclosures of U.S. patent application Ser. No. 14/958,124 and/or U.S. Provisional Patent Application No. 62/148,312 for purposes of claim construction, then the present patent application's teachings shall govern.

BACKGROUND

The inventive disclosures contained herein pertain to the protection of building surfaces, especially subterranean walls and floor under slabs, from water penetration.

Prefabricated waterproofing panels or sheets using natural water absorbing materials such as bentonite clay have been disclosed in U.S. Pat. Nos. 3,186,896, 3,445,322, and 4,467,015 and used for structural waterproofing. Water activates the clay material's characteristics. The clay material is not stable over time and will eventually wash away.

Water drainage is another component of a waterproofing system. Water drainage is used sometimes in combination with the waterproofing mechanism. Separate drainage devices are disclosed in U.S. Pat. Nos. 3,888,087 and 4,490,072. To inhibit clogging of the drainage passages by soil infiltration, a filter layer is sometimes bonded to prefabricated drain panels, as disclosed in U.S. Pat. Nos. 3,654,765; 4,574,541; 4,730,953; and 4,840,515. In U.S. Pat. No. 4,704,048, Ahlgrimm discloses the use of a filter material with enough strength to resist deformation into the drainage channels by back-fill loading.

Currently, commercial waterproofing membranes are dominated by rubberized-asphalt materials, while commercial drainage products are dominated by (a) a prefabricated, geocomposite panel having a polystyrene dimpled core, which is (b) covered on one side with a polypropylene non-woven filter fabric(s). The above-identified commercial drainage products are applied over the above-identified waterproofing membrane using an applied liquid adhesive, which represents a three-step installation process—the first step applies the waterproofing membrane; the second step applies the adhesive; and the third step applies the drainage products, in that order.

Waterproofing membranes using this application method are susceptible to imperfections from variation in the field installation of the membrane under uncontrolled or less-than-ideal conditions; these imperfections typically appear in the form of wrinkles and voids that are termed "fish-mouths" by those of ordinary skill in the art. These imperfections have the potential to degrade the waterproofing integrity of the installation, which will reduce functional reliability and therefore negatively impact structural warranties.

Furthermore, rubberized-asphalt waterproofing membranes are sensitive to the ultraviolet (UV) spectrum of light and will chemically degrade with exposure to the sun's rays, necessitating a maximum allowed time of 30 days before geocomposite drain panels must be installed. (See, e.g., 650 Membrane Technical Data Sheet, Ultraviolet Protection section, Polyguard® Products Inc.) Hence, it would be advantageous to apply such rubberized-asphalt waterproofing membranes in a controlled environment away from UV light (as well as any other potentially damaging environmental factors that are typically encountered at a construction site) so that such time constraints on the installation of geocomposite panels can be eliminated.

Still further, despite the rugged polypropylene non-woven filter fabric material, the earthen backfill must be applied with care to prevent damage to the filter material from rocks or other discrete material that can puncture or even rip the filter fabric, thereby introducing a latent defect into the installed drainage panel. Commercial horizontal drainage panels for under slab applications use void-maintaining woven laminates and sometimes woven fabrics bonded to the crush-resistant geocomposite panels; however, these are susceptible to de-bonding which would allow infiltration of poured non-hardened concrete or earth into the drainage channels.

In U.S. Pat. No. 8,039,081, Ianniello discloses a method for improving the bonding of filter material to the geocomposite panel. That disclosure, however, does not improve the protection of said filter material.

An improved drainage system structure able to resist crush and impact damage is disclosed in U.S. Pat. No. 5,263,792. In that patent, Davis teaches the limitations of filter fabric with respect to keeping the drainage channels free from clogging and other impediments; however, again, the filter material of this configuration would still be susceptible to damage from the application of earthen back-fill.

A combined waterproofing and drainage filter panel system is revealed in U.S. Pat. No. 4,943,185. In that patent, McGuckin discloses that using a captured bentonite-clay waterproofing material in conjunction with a structure for drainage and filtering. That system has structural and functional limitations, including the stability of the waterproofing material, the mass and inflexibility of the panels, the inability to ship and store the system in rolls, and the need to secure the system to the wall that is being protected using mechanical means such as nails or tacks. Those limitations conform to the current commercial waterproofing standard configuration.

After a waterproofing system has been applied, there is no real way to verify the quality of the installation, and furthermore, functional failures can only be detected after leakage has already occurred, usually through evidence of moisture or water within the protected structure itself. Still further, location of the actual leakage point is often difficult because water that has infiltrated a building may travel a good distance along a wall, behind the defeated waterproofing membrane, before actually entering the wall (aka, structure). Even further, the problem can be compounded by water damage to the foundation of the structure and to materials or items within the below-ground levels of a building. This may explain why standard warranties on existing commercial waterproofing systems are typically offered for only one year after installation and, under special conditions, for only five years after installation. These issues have created the need for improved reliability of the waterproofing installation, as well as the necessity for leakage detection before water can damage the protected structure.

For commercial structures, electrical leak-detection methods have been developed that map the electric-field potential across a conductive surface to measure the current flow to the grounded building structure along the leakage path (see, e.g., U.S. Pat. Nos. 6,331,778, and 8,566,051). To enhance leak detection, other techniques introduce a current-carrying channel external to the waterproofing barrier undergoing test, such as using an electrically conductive primer coating (see, e.g., U.S. Patent-Application Publication No. US 2014/0361796). While these methods are useful for above-ground horizontal waterproofing installations such as roofing, they do not address solving the below-ground leak detection problem. Moreover, while electrically-based methods for the detection of leaks have been developed to monitor for waste or chemical leakage from industrial containment facilities (see, e.g., U.S. Pat. Nos. 4,404,516; 4,725,785; 5,288,168; and 6,331,778), these techniques are not suited for below-grade structural waterproofing systems.

To sense the presence of water, an electrical-moisture-detection mechanism using inductive coupling between a sensor and reader, or alternatively, an electrically connected sensor and reader using direct current (DC) is revealed in U.S. Pat. No. 5,463,377, while other devices make use of tape-based or film-based sensors to detect the presence and/or location of moisture (see, e.g., U.S. Pat. No. 7,292,155 and U.S. Patent-Application Publication No. US 2012/0074967). These methods require the placement of a plurality of sensor and reader pairs in close proximity to each other, or a plurality of electrically-connected sensors switched or linked to a single reader. Furthermore, because the sensors are discrete from the monitored structure, their use requires installation after standard waterproofing materials are applied and/or to accommodate sensor placement before or during the installation of waterproofing materials, which reflects nonstandard modifications to the underlying structure itself. Commercially available hand-held moisture-sensing instruments are available such as those from Tramex Ltd.; however, both the discrete sensing mechanisms and the hand-held instrumentation, cannot be used with existing commercial below-grade structural waterproofing systems.

In the construction industry, a below-grade commercial waterproofing system installation represents situation where the costs of failure can be very high, and as such, methodologies to address and mitigate the risks are needed. For the aerospace, medical devices, automotive, and other failure-adverse fields, the FMEA (Failure Modes and Effects Analysis) method has been in use for decades as a necessary engineering tool to enhance the reliability of systems through identification of potential failure modes and then mitigating the associated risks. Many companies—in what would be considered non-critical industries such as consumer electronics—have also adopted FMEA as part of their normal design and process development cycles, because total costs are reduced by identifying potential failure modes and mitigating the risks.

Similarly, a below-grade commercial waterproofing system installation is an application where the costs of failure are often high. Unlike above-grade waterproofing applications such as roofing and decks, a latent defect within a below-grade system may not be readily detected until considerable progression of the leakage has already occurred, and the below-grade nature of the installation makes locating and correcting the problem an expensive proposition. If a building's contents such as computer infrastructure, vital, records or laboratory facilities (to name but a few) are damaged or destroyed by the water infiltration, the costs increase even more. If people become ill from the formation of toxic mold, and a structure becomes unusable to the occupants, the liability and costs can become catastrophic. With this perspective, it is surprising that risk-control methodologies such as FMEA are not used routinely in the below-grade waterproofing field despite the fact that FMEA processes are relatively simple to implement, and the benefits of FMEA have been demonstrated by over half a century of use in critical applications where failure is literally not an option.

The process FMEA, as applied to an existing current-art below-grade waterproofing system—installed on existing vertical concrete foundation walls for new-construction structures—identifies 15 potential failure modes, which will result in water infiltration into the structure. The associated risks are shown to be unacceptably high. What is needed is an alternative waterproofing system (including fabrication methodologies) that mitigates the risk down to an acceptable level.

BRIEF SUMMARY

The inventive disclosures contained herein are designed to address the limitations of the above-identified existing art. To improve and/or eliminate the variation in installation quality from the layered multistep field-installation of commercial waterproofing systems, the job-site assembly technique is replaced and improved with a factory-controlled process that bonds geocomposite drainage panels to waterproofing membranes prior to installation in the field. Additionally, a filter layer of each geocomposite drainage panel is mechanically captured by a factory-applied outer perforated anti-abrasion layer made from the same material as the core of the drainage panel, which acts to protect the filter material from puncturing and tearing. Thus, because of a factory-controlled manufacturing process with inherently low variation in quality, only the improved waterproofing-panel assembly is installed on a wall as a pre-fabricated unit. Finally, the waterproofing membrane incorporates an electrically conductive layer that allows the membrane itself to serve as an electronic sensor and provide a means for continuous monitoring of installation integrity through capacitance measurement, characterization of the installation topography by capacitance and resistance measurements, and intrinsic post-installation functional validation (i.e., leakage detection) by resistance measurement. Overall, this improved waterproofing-panel configuration and related processes serves to reduce the total costs of the system to the contractors, building owners, and occupants.

In embodiments, the improved waterproofing-panel assembly comprises a composite waterproofing membrane, a drain-board core, and a filter fabric over the drain board. In variations, the composite waterproofing membrane also has a rubberized-asphalt layer, and the rubberized-asphalt layer has a proximal surface side and a distal surface side, wherein the proximal side surface is positioned, relative to the distal surface side, closest to a building's surface. In some variations, a pressure-sensitive rubberized-asphalt adhesive coating under the proximal surface side, the proximal surface side being designated the composite waterproofing membrane's base. Also included, in other variations, are a film backing positioned over the distal surface side, and an electrically-conductive membrane layer with metal strips is between the rubberized-asphalt layer and the film backing. The drain-board core is disposed over the film backing. In addition, there can also be an electrical conduit that couples the electrically-conductive membrane layer or metal strips to an electrical-condition-measurement device. In even more variations, the improved waterproofing-panel assembly also comprises a fluid-applied membrane on the target building's concrete substrate.

In embodiments, an electrical-condition-measurement device measures an external resistance to provide: (a) intrinsic leak-detection capability, (b) monitoring of a functional topography of the composite waterproofing membrane, (c) an inference to confirm whether the composite waterproofing membrane contacts the building's surface, and (d) combinations thereof. In addition, the improved waterproofing-panel assembly can further comprise a conductive primer positioned between the proximal surface side and the building's surface, and an electrical conduit that couples the conductive primer to an electrical-condition-measurement device, wherein the electrical-condition-measurement device measures an external resistance to provide: (a) intrinsic leak-detection capability, (b) monitoring of a functional topography of the composite waterproofing membrane, (c) an inference to confirm whether the composite waterproofing membrane contacts the building's surface, and (d) combinations thereof.

In various applications, the electrical-condition-measurement device is selected from the group consisting of a hand-held ohmmeter, a capacitance measurement using an LCR meter, and a permanently wired voltage and leakage-current device. In an embodiment, the improved waterproofing-panel assembly appends, attaches, adheres, secures, or connects to the building's surface without penetrating the composite waterproofing membrane. The improved waterproofing-panel assembly is adapted to contact soil, sand, rocks, gravel, clay, water, or combinations thereof, wherein the building's surface is selected from the group consisting of a basement floor, a slab, a subterranean basement vertical wall, a partially subterranean basement vertical wall, a basement vertical wall, and a slab's side surface. Further, in variations, the improved waterproofing-panel assembly can also comprise an anti-abrasion layer over the filter fabric.

The method of installing the improved waterproofing-panel assembly comprises appending, attaching, adhering, securing, or connecting an improved waterproofing-panel assembly to a building's surface without penetrating the composite waterproofing membrane and applying pressure to the improved waterproofing-panel assembly. In some embodiments, the method also entails connecting the electrical conduit that couples the electrically-conductive membrane layer or metal strips to the electrical-condition-measurement device or applying the conductive primer positioned under the interior-surface side, and connecting the electrical conduit that couples the electrically-conductive membrane layer or metal strips to the electrical-condition-measurement device or connecting the second electrical conduit to the electrically-conductive membrane layer or metal strips to the electrical-condition-measurement device.

Ideally, using Building Information Modelling (BIM) techniques, the improved waterproofing-panel assemblies are pre-fabricated under factory-controlled conditions that eliminates most of the construction-site flaws, variations, and inconsistencies that cause bad installations. These factory-pre-fabricated improved waterproofing-panel assemblies can be precisely joined in the field to create a final below-grade waterproofing structure, though as for any in-field installation specific installation detailing, including the proper sealing at interface joints between sections being installed, will still have to be performed.

The foregoing Brief Summary is intended to merely provide a short, general overview of the inventive disclosure described throughout this patent application, and therefore, is not intended to limit the scope of the inventive disclosure contained throughout the balance of this patent application, including any appended claims and drawings.

BRIEF DESCRIPTION OF THE APPENDICES AND DRAWINGS

The following is a brief description of the Appendices and Drawings provided to support the inventive disclosures herein, and it must be noted that these illustrations are not to scale and are simply intended to convey the basic mechanical structures of the apparatus depicted:

Appendix A Provides a formal process Failure Modes and Effects Analysis (FMEA) worksheet for the improved commercial building waterproofing system.

FIG. 11A depicts one embodiment of an abstract rendering of the installation verification of an improved waterproofing system using a capacitance measurement when there is a void between the waterproofing membrane and the concrete wall.

FIG. 11B depicts one embodiment of the equivalent capacitors of the configuration depicted in FIG. 11A.

FIG. 11C depicts another embodiment of the equivalent capacitors of the configuration depicted in FIG. 11A.

Figure 16A:
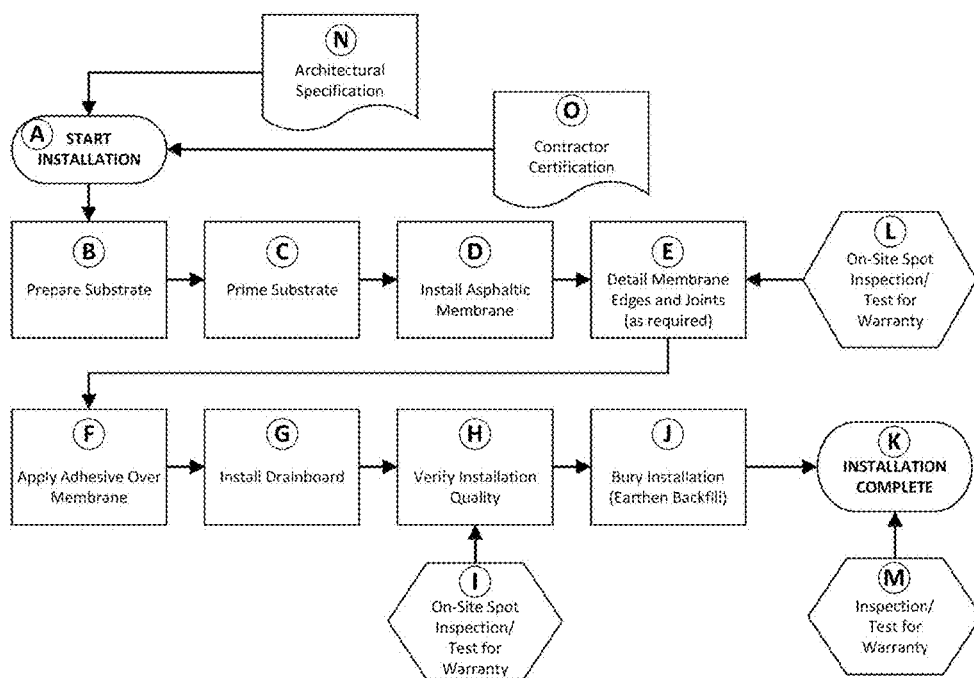
FIG. 16A depicts a typical overall current-art process flow for the installation of a prior-art waterproofing panel system.
Figure 16B:
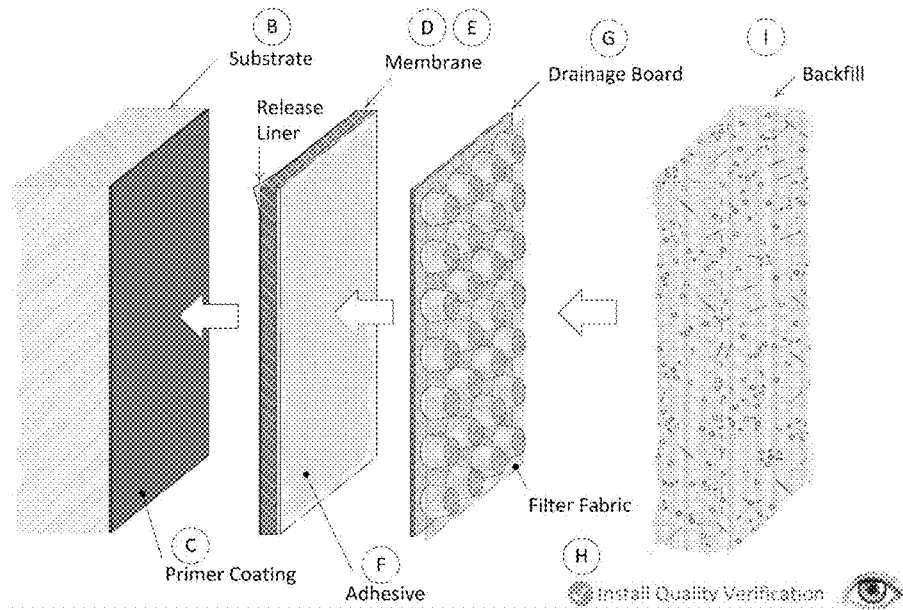

FIG. 16B diagrams the steps in FIG. 16A. (A corner fragment is shown, with the drawing not to scale.)

Figure 17A:
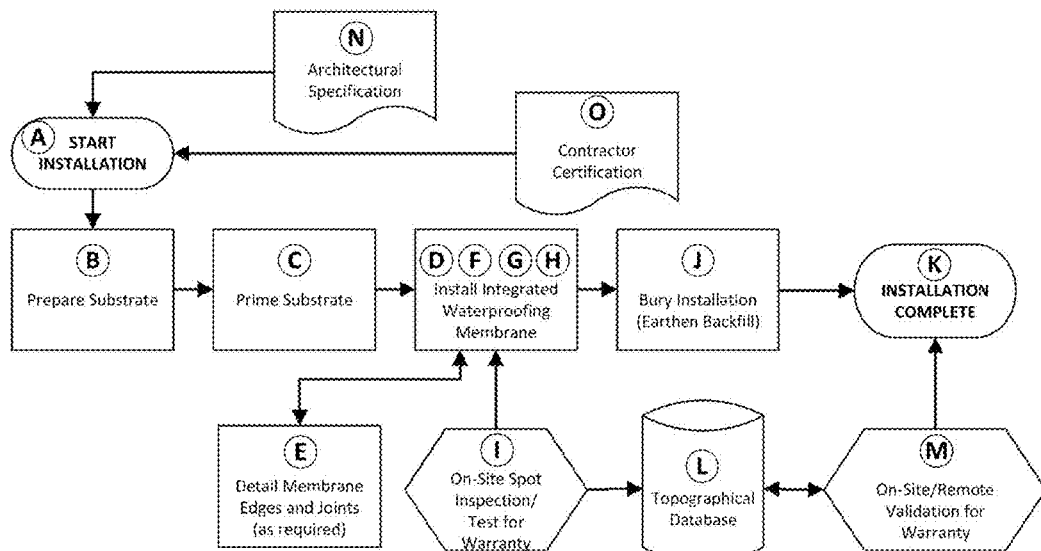

FIG. 17A depicts an embodiment of an improved process flow for the manufacturing and installation of an improved waterproofing panel system.

Figure 17B:
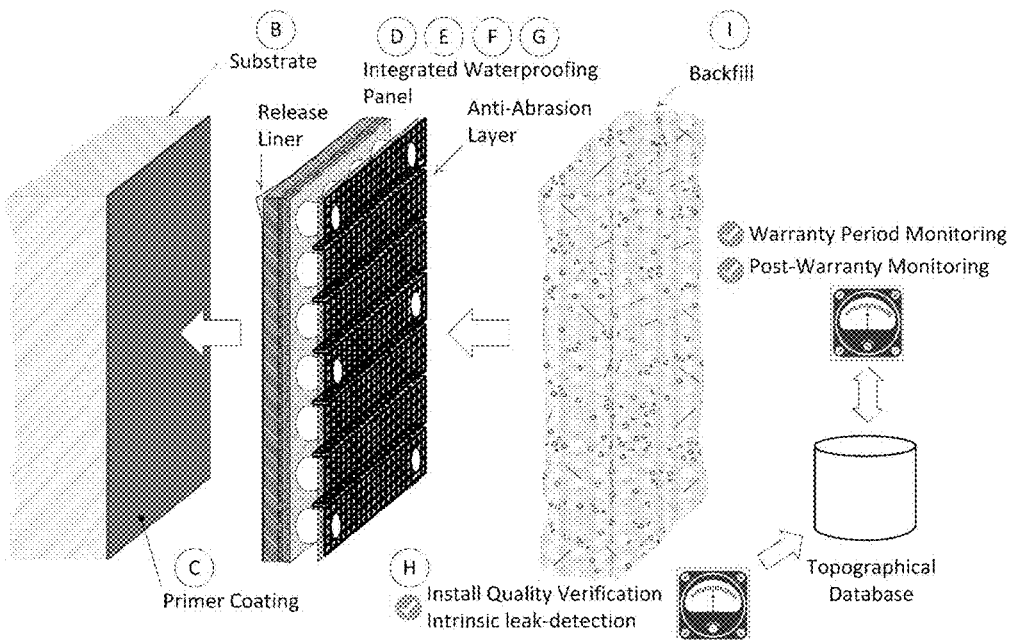

FIG. 17B diagrams the steps in FIG. 17A. (A corner fragment is shown, with the drawing not to scale.)

Figure 18:
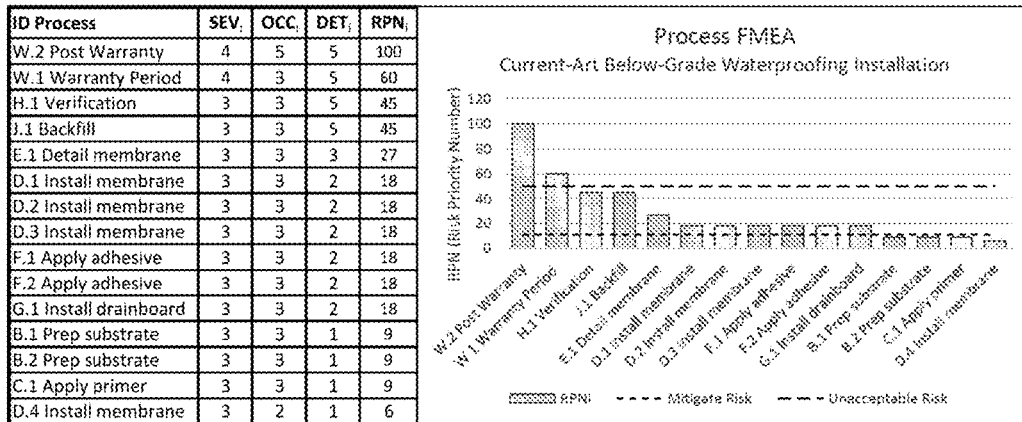

FIG. 18 depicts the current-art initial process risk assessments for each identified potential failure mode, and are graded from highest to lowest.

Figure 19:
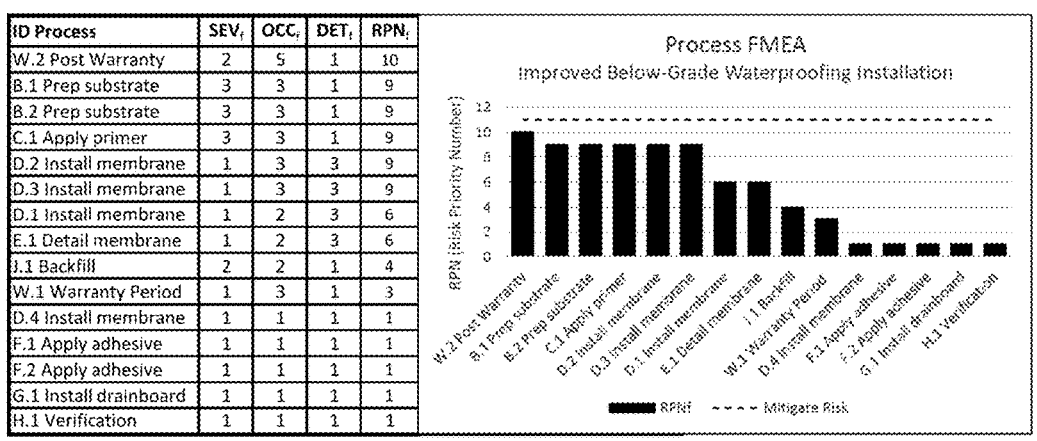

FIG. 19 depicts one embodiment of the initial process risk assessments for each identified potential failure mode for an improved waterproofing system manufacturing and installation process, and are graded from highest to lowest.

DETAILED DESCRIPTION

I. Overview

The inventive disclosures contained herein are designed to address the limitations of the above-identified existing art. To improve and/or eliminate the variation in installation quality from the layered multistep field-installation of commercial waterproofing systems, the job-site assembly technique is replaced with a factory-controlled process that bonds geocomposite drainage panels to waterproofing membranes prior to installation. Additionally, a filter layer of each geocomposite drainage panel is mechanically captured by a factory-applied outer perforated anti-abrasion layer made from the same material as the core of the drainage panel, which acts to protect the filter material from puncturing and tearing. Finally, the waterproofing membrane incorporates an electrically conductive layer that allows the membrane itself to serve as an electronic sensor and provide a means for installation verification through capacitance measurement, characterization of the installation topography by capacitance and resistance measurements, and intrinsic post-installation functional validation (i.e., leakage detection) by resistance measurement. In even more variations, the improved waterproofing-panel assembly also comprises a fluid-applied membrane on the target building's concrete substrate.

In an embodiment, a factory-controlled process is used to bond high-impact polystyrene drainage panel cores to the polyethylene-reinforced side of a rubberized-asphalt waterproofing membrane using an industrial-grade chemically-compatible organic adhesive compound, preferably a low Volatile Organic Compound (VOC) adhesive compound, and on the opposing installation side of the waterproofing membrane, there is a pressure-sensitive adhesive (commonly referred to as a "peel and stick" adhesive) release liner of silicone, or a functionally equivalent non-stick material, for easy application of waterproofing membranes to existing concrete vertical walls, and depending on the application, there are also non-pressure-sensitive adhesive waterproofing membranes using a non-woven geotextile for blind-side vertical wall or under-slab floor installations. The waterproofing membrane can have various thicknesses, and typically ranges between 60 to 100 mils, depending on the application. The outer side of the drainage panel opposite to the waterproofing membrane has multiple layers of non-woven synthetic filter material such as polypropylene to protect the drainage channels from soil infiltration and clogging after installation and earthen back-fill. To trap and protect the filter layer from damage, and maintain the structural integrity of the filtering and drainage system, a perforated anti-abrasion layer made from high-impact polystyrene or any functionally equivalent fungus and rot-resistant material, is attached to the dimple tops of the drainage panel core using a plurality of non-protruding polystyrene fasteners in a leak-proof configuration, as well as an industrial-grade low-VOC adhesive. Because of the additional strength and mechanical stability afforded by the anti-abrasion layer, the waterproofing panel may also have pressure applied by a device such as a roller after installation. The drainage panel will also withstand normal construction traffic without damage during horizontal installations. The anti-abrasion layer also has a bend-relief feature in the form of transverse creases that provide the integrated panel with longitudinal flexibility to facilitate storage and shipment in rolls.

The pressure-sensitive adhesive drainage panel with an integrated filter, offers the advantage of replacing the field-applied wet adhesive with a factory-controlled adhesive layer, thereby negating the need for application of the wet adhesive in the field, and eliminating the variations in curing times and quality of the wet adhesive that typically arise from environmental factors such as ambient temperature, humidity and particulate contamination resulting from wind-borne material such as dust and various types of organic matter. Furthermore, because the waterproofing drainage panel also includes the anti-abrasion protective layer, the added lateral stability during installation effectively eliminates the conditions favoring the creation of wrinkles and fish mouths in the waterproofing membrane. Panel-to-panel vertical seams are sealed with overlapping end laps that create a fully adhered bond between waterproofing membranes, along with an overhanging filter and anti-abrasion layers feature that extends past the dimple top, shingling over the leading edges of adjacent panels, preventing soil infiltration after the system has been installed. Panel-to-panel horizontal seams are made using factory-made polystyrene core field joints that have a self-adhesive peel-and-stick rubberized-asphalt backing and a single or double-sided adhesion flaps that form watertight interfaces to each panel's waterproofing membrane, as well as pressure-sensitive adhesive strips on the upper surface of the joint that act to reinforce the membrane termination. To provide protection after the horizontal joint has been detailed, a polystyrene cap strip is installed afterward, which also serves to prevent soil infiltration into the drainage panel core. Additionally, the system provides factory-made inner and outer corner vertical end-laps with a core structure and termination method identical to the horizontal panel field joint, and these inner and corner end-laps are compliant to variations in the corner angles of the substrate. Furthermore, the inner corner end-lap may also be used horizontally as the termination joint at the wall-to-footer Interface. The field joint, end-lap and footer termination structures are designed to facilitate the application of detailing cant beads at the exposed membrane end-seams. Finally, vertical-panel seams from cuts made in the field are over-lapped with composite strips of anti-abrasion material and filter fabric to seal these irregular joint openings.

A variety of factory-made standardized accessories allows for the accommodation of penetrations and other variables encountered during installation. For single penetrations, standardized half-pieces are used to fit around the penetrating pipe or conduit, and these have panel interfaces that are similar to those used for the vertical and horizontal terminations described above. For multiple or irregular penetrations, a cofferdam may be installed around the penetrations using a selection of various lengths of corner pieces, with panel-sided interface features similar to those described above. A dam feature is incorporated that acts as a form to allow liquid waterproofing material to be poured around the penetrations and to be held in place until the material has cured. When installed on a properly detailed and primed substrate, this waterproofing system is designed to eliminate the typical quality problems arising from the human-factor and environmental variation during field installation. The factory-controlled process that integrates the waterproofing membrane and drainage panel, facilitates an inherently wrinkle and void-free application of the membrane to the substrate. Furthermore, only one process step—the pressure-sensitive adhesive operation—is required during the installation, thereby saving labor hours and significantly reducing the time required to finish the job. The variety of factory-made field joints allows high-quality terminations and panel unions to be made at the inside and outside corners, footers and between panels, while the integrated drain panel provides built-in UV protection of the waterproofing membrane, which helps to simplify construction logistics since the waterproofing installation need not be buried within the typical 30 to 60 days. Furthermore, the integrated anti-abrasion layer eliminates any concerns of damage to the filter fabric during the earthen back-fill operation; conversely, any damage to a conventional drainage board filter layer that happens during the back-fill operation will not be detected until water stops flowing and hydrostatic pressure increases due to sediment-clogged drainage passages. For these reasons, the term 'Poka-Yoke' (mistake-proofing a process) can be applied to this waterproofing system.

In another embodiment, an electrically-conductive film of conductive-particle infused polyethylene augmented with strips of metallic mesh, is integrated onto the drainage panel side of the water proofing membrane under the protective polypropylene backing film, into which a continuous DC or time-varying AC low-voltage potential is introduced via an electrical interface at the top of the waterproofing panel. This conductive layer is used to provide the means for making the electrical measurements necessary for installation verification and functional validation by leakage detection of the waterproofing system. It should be recognized that a sufficiently fine metallic mesh, foil, or film may also be used to form the conductive layer itself without altering the function of this invention embodiment.

To prepare a concrete wall for the application of an improved waterproofing system, the already leveled and detailed concrete substrate is coated with a primer to seal the substrate. The preferred method for installation on existing vertical walls uses an electrically conductive primer, which is chemically compatible with the rubberized-asphalt waterproofing membrane, and exhibits a surface resistivity after application of between 50,000 and 250,000 ohms-per-square. It must be noted that the electrically conductive primer is necessary for the installation verification measurement, but it would not be required for the leakage detection measurement.

Additionally, for blind-side installations and under-slab applications where the non-woven geotextile is used instead of the pressure-sensitive adhesive release liner, the conductive primer is not required. Rather, in these applications, the concrete wall or floor is poured in place against a pre-installed waterproofing system and for both of these applications without conductive primer, the leak detection measurement will still function.

AC voltage is used to assess the waterproofing membrane's dielectric behavior through the measurement of the capacitance between the electrically conductive layer and the electrically primed substrate, and this provides information about the mechanical integrity of a waterproofing membrane's installation against the concrete substrate. DC voltage is used for the detection of moisture leakage through the waterproofing membrane, via measurement of the electrical resistance between the conductive layer and the protected structure's earth ground. For both measurements, either temporary or permanent electrical connections are made to the conductive waterproofing membrane's conductive layer and the substrate or building earth ground. The capacitance measurement is made using an off-the-shelf instrument such as an LCR meter, and this operation would be performed immediately after an installation, preferably before the back-fill is applied, allowing any detected problems to be quickly addressed. The measurement may also be performed after the back-fill operation as a final check that the dielectric characteristics of the waterproofing system are within specification.

The resistance measurement may be made by a variety of methods such as a hand-held ohmmeter or with longer-term, in-place, more-customized instrumentation. For example, passive Radio Frequency Identification (RFID) based sensors with anti-collision capability, electrically connected to each waterproofing panel, would facilitate a fast survey of the waterproofing installation using a RFID reader. Each installed waterproofing panel would be identified by a unique code embedded on the RFID sensor device connected at or near the top of each water proofing panel, or alternatively, just below ground level in a credit card sized or smaller environmentally-protected enclosure. The waterproofing panels would be interrogated remotely using a hand-held reader device carried by an operator walking along the wall after the waterproofing system has been installed after the wall is buried by earthen backfill as a quality-control verification that the initial waterproofing installation is leak-free. Additionally, the interrogation operation could be repeated by an operator at regular intervals, or continuously using automatic data-logging equipment, in order to allow the integrity of the waterproofing system to be validated over time. All measurements made through remote operator-based interrogation could be stored in a digital memory device in the hand-held reader for later transfer to a computerized database. The initial measurements after installation and subsequent measurements over time would create a measurement topography for each building that would be compared using regression, and/or using log-log regression, or using other commonly applied statistically-based methods for determining trends.

Periodic leak-detection measurements, made possible by the intrinsic leak-detection capability of the improved waterproofing system and performed over the life of the building, could be part of a "smartbuilding" concept facilitated by the "Internet of things", where data is collected by a computer via either a Local Area Network (LAN) and/or over the Internet via a Transmission Control Protocol/Internet Protocol (TCP/IP) connection, and automatically monitored using Statistical Process Control (SPC) as commonly practiced in the manufacturing industry, which would allow anomalies in the data to be identified before a physical leak progresses far enough to actually breach a protected structure's foundation. SPC in conjunction with sophisticated Digital-Signal Processing (DSP) techniques would be used to identify the potential for failures, predict the life of the waterproofing installation, and perform diagnostic self-checks on the intrinsic leak-detection sensors. The level of electronic leak detection, monitoring and remote sensing used for a waterproofing system would provide the empirical data necessary for rigorously establishing the scope and duration for warranty coverage against water leakage and infiltration.

II. Terminology

The terms and phrases as indicated in quotes (" ") in this Section are intended to have the meaning ascribed to them in this Terminology Section applied to them throughout this document, including the claims, unless clearly indicated otherwise in context. Further, as applicable, the stated definitions are to apply, regardless of the word or phrase's case, to the singular and plural variations of the defined word or phrase.

The term "or", as used in this specification, drawings, and any appended claims, is not meant to be exclusive; rather, the term is inclusive, meaning "either or both".

References in the specification to "one embodiment", "an embodiment", "a preferred embodiment", "an alternative embodiment", "a variation", "one variation", and similar phrases mean that a particular feature, structure, or characteristic described in connection with the embodiment is included in at least an embodiment of the invention. The appearances of the phrase "in one embodiment", "in one variation", and/or similar phrases in various places in the specification are not necessarily all meant to refer to the same embodiment.

The term "couple" or "coupled", as used in this specification, drawings, and any appended claims, refers to either an indirect or a direct connection between the identified elements, components, or objects. Often the manner of the coupling will be related specifically to the manner in which the two coupled elements interact.

The term "removable", "removably coupled", "readily removable", "readily detachable", "detachably coupled", and similar terms, as used in this specification, drawings, and any appended claims, refer to structures that can be uncoupled from an adjoining structure with relative ease (i.e., non-destructively and without a complicated or time-consuming process) and that can also be readily reattached or coupled to the previously adjoining structure.

As used in this specification, drawings, and any appended claims, directional and/or relational terms such as, but not limited to, left, right, nadir, apex, top, bottom, vertical, horizontal, back, front, lateral, proximal, and distal are relative to each other, are dependent on the specific orientation of an applicable element or article, are used accordingly to aid in the description of the various embodiments, and are not necessarily intended to be construed as limiting in this specification, drawings, and any appended claims.

As used in this specification, drawings, and any appended claims, the terms "over" and "under", are relative terms. For example, the pressure-sensitive rubberized-asphalt adhesive coating is positioned "under" the proximal surface side because the proximal surface side is designated the composite waterproofing membrane's base. Therefore, when the proximal surface side is, for example, positioned below a basement floor or a slab, the pressure-sensitive rubberized-asphalt adhesive coating is actually over the proximal surface side, yet the pressure-sensitive rubberized-asphalt adhesive coating is still "under" the proximal surface side since the proximal surface side is designated as the composite waterproofing membrane's base.

As used in this specification, drawings, and any appended claims, the terms "posterior" and "anterior", are relative terms. For example, the posterior side of the integrated drain panel with intrinsic leak detection is the surface that is applied to/facing the substrate (e.g., concrete building wall), and the anterior side of the integrated drain panel with intrinsic leak detection is the surface that has the anti-abrasion layer facing the earthen backfill.

As applicable, the terms "about" or "generally", as used herein unless otherwise indicated, means a margin of +−20%. Also, as applicable, the term "substantially" as used herein unless otherwise indicated means a margin of +−10%. It is to be appreciated that not all uses of the above terms are quantifiable such that the referenced ranges can be applied.

As used in this specification, drawings, and any appended claims, the term "below-grade" is a construction-industry term for below-ground or subterranean installations.

Figure 1A:
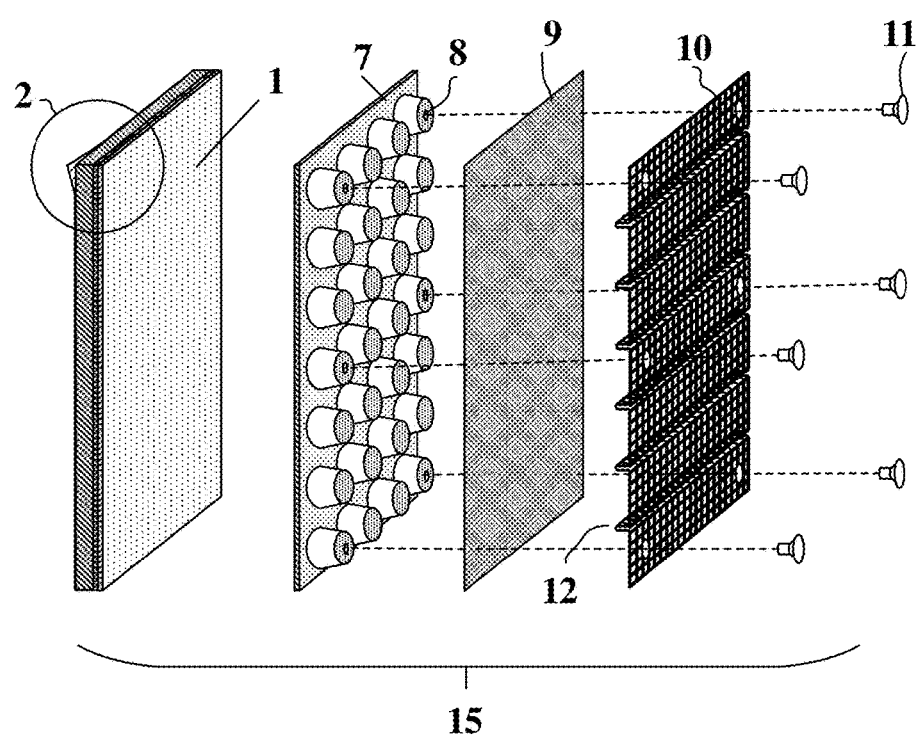
FIG. 1A depicts one embodiment of an exploded view of a corner section the improved waterproofing panel membrane with its various components.

III. An Improved Building Foundation Waterproofing and Drainage System With Intrinsic Leak Detection Capabilities This Section III is directed to an improved waterproofing and drainage system with intrinsic leak detection for use in building structures, such as vertical and horizontal foundational structures that are disposed below ground. Refer to FIGS. 1A though 15C.

In an embodiment, the improved waterproofing-panel assembly 15 has a composite waterproofing membrane 1, a drain-board core 7, a filter fabric 9, an anti-abrasion layer 10; and a plurality of flat-topped high-impact polystyrene rivets 11. The drain board 7 prevents the build-up of hydrostatic pressure against a wall after installation of the improved waterproofing-panel assembly 15, and the filter fabric 9 prevents soil from clogging the drainage channels in the improved waterproofing-panel assembly 15. In variations, the drain-board core 7 can have a plurality of flat-topped dimples 8. In a typical application, the flat-topped dimples are comprised of a high-impact polystyrene with the ability to withstand a compressive loading of at least 18,000 lbf/ft$^2$ and provide a gravity-assisted, water-drainage flow of no less than 20 gallons/minute per foot of cross-sectional width. In many applications, the filter fabric 9 is comprised of a non-woven polypropylene material. Preferably, the filter fabric 9 is comprised of multiple layers of non-woven polypropylene material. In more variations, the anti-abrasion layer 10 is comprised of a perforated high-impact polystyrene sheet, preferably at least 60 mils in thickness. The anti-abrasion layer 10 allows a water flow rate of no less than 100 gallons/minute per ft$^2$ of area, with a plurality of transverse creases 12 to provide longitudinal flexibility.

Figure 1B:
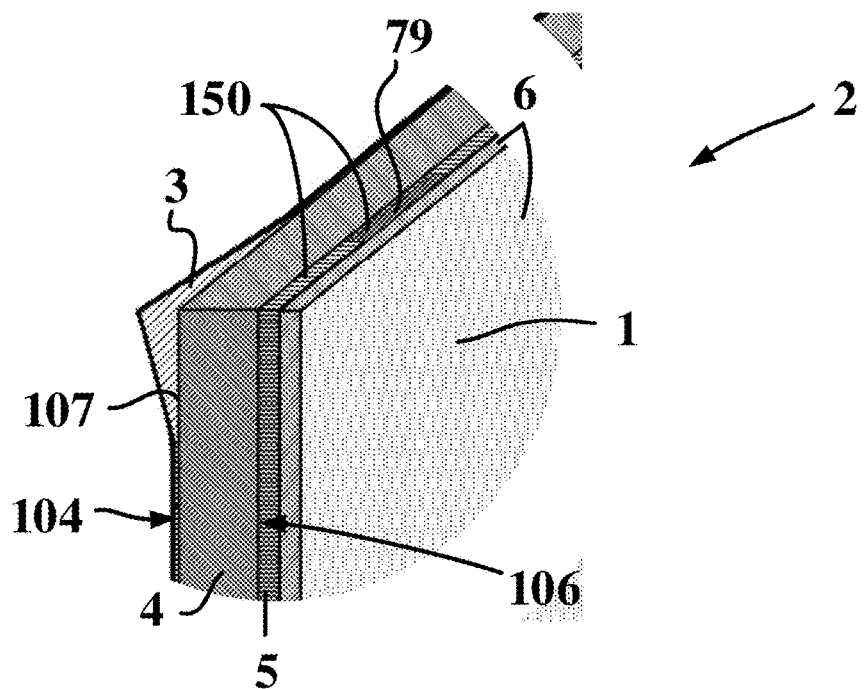
FIG. 1B depicts one embodiment of the details of the improved waterproofing membrane with its various layers.

In other embodiments, the composite waterproofing membrane 1 has a rubberized-asphalt layer 4. The rubberized-asphalt layer 4 has a proximal (that is, interior) surface side 104 positioned to be closer to a building wall, and a distal (aka, exterior) surface side 106 positioned on the opposite side of the interior surface side 104 as illustrated in the close-up view of a corner 2 of the waterproofing membrane 1 in FIG. 1B. The rubberized-asphalt layer 4 is commonly a mixture of rubber and asphalt—also called bitumen—and is reinforced on or over the exterior surface side 106 with a high-density polyethylene (HDPE) cross-laminated film backing 6. Positioned on or under the interior surface side 104 is a pressure-sensitive rubberized-asphalt adhesive coating 107 protected by a release liner 3. In many variations, the release liner 3 is comprised of a non-stick material such as silicon or treated paper. In some alternative variations, and depending on the application, the pressure-sensitive rubberized-asphalt adhesive coating 107 and release liner 3 may be replaced with a non-woven polypropylene fabric material.

In many embodiments, an electrically-conductive membrane layer 5 is laminated between the rubberized-asphalt layer 4 and the outer reinforcing film backing 6. Furthermore, a plurality of conductive metallic strips 79 approximately 0.5 inches in width are laminated between the electrically conductive membrane 5 and the HDPE (high-density polyethylene) cross-laminated film backing 6. The plurality of metallic strips 79 are longitudinally positioned in the waterproofing membrane 1, and are spaced transversely a predetermined distance. That predetermined distance is preferably every 8 inches or thereabouts. In many applications, the overall thickness of the composite waterproofing membrane 1 will range between 60 and 100 mils depending on the application.

Figure 1C:
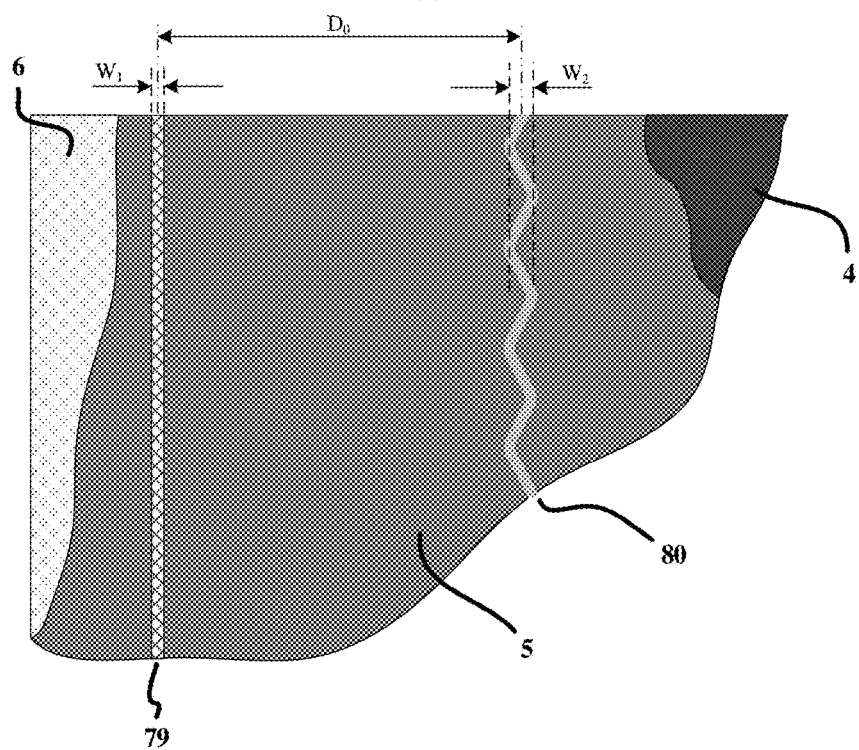
FIG. 1C depicts one embodiment of the structure of the conductive components inside the improved waterproofing membrane.
Figure 2:
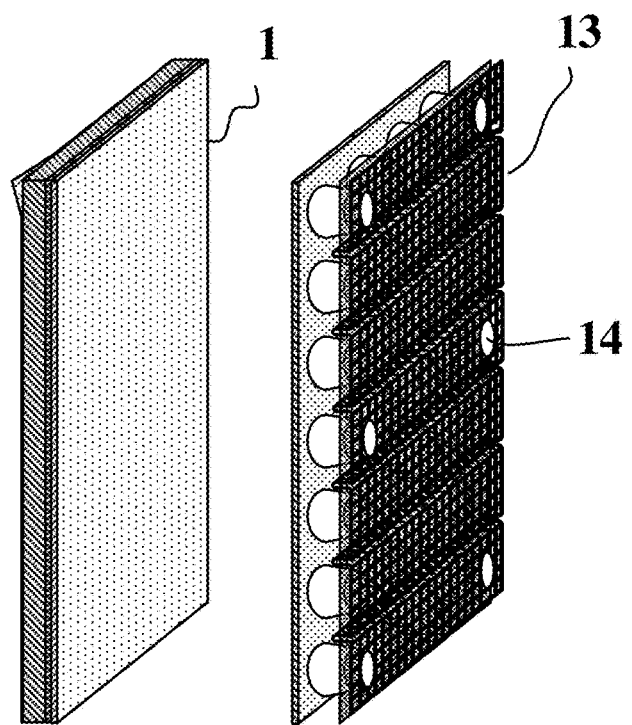
FIG. 2 depicts one embodiment of a view of a partially assembled section of the improved waterproofing membrane and the drain panel assembly.
Figure 3:
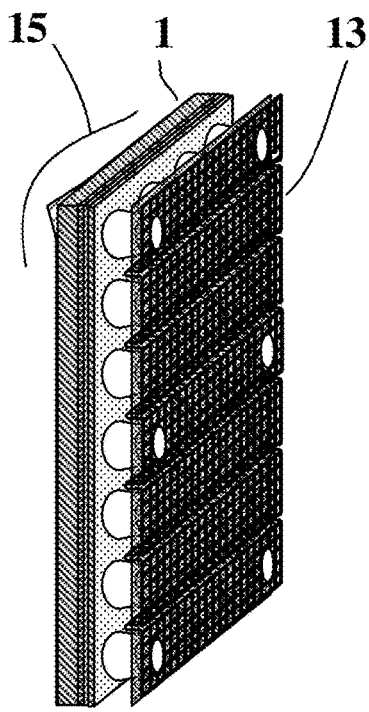
FIG. 3 depicts one embodiment of a view of a fully assembled section of the improved waterproofing membrane and the drain panel assembly.

In still more embodiments, the electrically conductive membrane layer 5 has an additional thin layer of carbon-impregnated HDPE film, typically 2 to 3 mils in thickness, that is chemically compatible with the rubberized-asphalt, with a surface resistivity of approximately 500 ohms per square. In many variations, the metallic strips 79 are composed of Type-316 type stainless steel with a count ranging from 80 to 120 wires per inch, and a wire diameter of less than 5 mils, although metalized plastics such as aluminum-coated polypropylene film or purely metal films such as aluminum foil may also be used to provide the same function. Together, the electrically conductive membrane layer 5 and the woven-metal-mesh strips 79 are bonded to form a sensing element 150 within the composite waterproofing membrane 1, where (a) the electrically conductive membrane layer 5 provides generally conductive layer throughout the waterproofing membrane, while (b) the woven metal mesh strips 79 improve the conductivity along the length of the waterproofing membrane 1 roll and also provide an electrical connection point to the waterproofing membrane 1. The dimensions and spacing of the conductive film 5 and metal mesh strips 79 may be altered without changing or altering the function of these components. Similarly, in a preferred embodiment, different conductive materials such as metalized plastic films and metallic foils may also be substituted for either component without substantially altering the electrical function of the sensing element. FIG. 1C reveals an embodiment of how the metallic strips 79 are arranged within the composite waterproofing membrane 1 and shows a corner fragment of the composite waterproofing membrane 1. The view of this illustration is a view of the exterior side surface of the of the waterproofing layer 1 wherein most of the cross-laminated HDPE backing layer 6 is shown peeled away except for the fragment to the left. The peeled-away backing layer 6 exposes the electrically conductive membrane 5. A small portion of the electrically conductive membrane 5 is also peeled away to expose the rubberized-asphalt waterproofing layer 4 below.

In still more embodiments, and referring still to FIG. 1C, the metal mesh strip 79 with width $W_1$ of the preferred embodiment appears above the electrically conductive membrane 5 because the metal mesh strip 79 is laminated between the electrically conductive membrane 5 and the cross-laminated HDPE backing layer 6 (which peeled away). An optional metalized foil or plastic strip 80 is also shown for reference purposes, and in this view, the metalized of side of the plastic strip is oriented downward to make electrical contact with the electrically conductive membrane 5. Furthermore, the foil or metalized plastic strip 80 is shown with a rounded zigzag pattern to provide longitudinal strain relief within the composite waterproofing membrane 1, and the magnitude of the pitch of this zigzag pattern would be defined by width $W_2$. The distance between the center-lines of the metallic strips is defined by distance $D_0$; in the preferred embodiment, width $W_1$ is 0.5 inches and distance $D_0$ is 8 inches. It should be understood that these dimensions may be altered to optimize the characteristics of the sensing elements within the composite waterproofing membrane 1 for maximum performance of the associated external electronic measurement devices.

In an embodiment of an assembled improved waterproofing membrane 1 and the drain panel 13 assembly, the assembled geocomposite drain panel 13 (which is the drainboard core 7, the filter fabric 9, and the anti-abrasion layer 10) has installed 14 reinforcing rivets 11. In variations, the filter fabric 9 is secured between the drain-board core 7 and the anti-abrasion layer 10 by using an industrial-grade chemically-compatible low volatile organic compound (VOC) adhesive to adhere to the dimple tops 8 of drainboard core 7. Additionally, a plurality of rivets 11 are installed 14 through the anti-abrasion layer 10 into existing holes on a fraction of the plurality of dimple tops 8 of drain core board 7. FIG. 7B illustrates an embodiment of the detail of an installed rivet 14 configuration detail, wherein the rivet 11 has been flared under the dimple of the drain-board core 7 to firmly reinforce the attachment of the anti-abrasion layer 10, and wherein the industrial-grade chemically-compatible low-VOC adhesive 40 has been used to fill the inside end of the dimple tops 8 of drain-board core 7 to provide a leak-proof joint. Additionally, the industrial-grade chemically-compatible low-VOC adhesive 40 is used at all the dimple tops 8 of drain-board core 7 contact points with anti-abrasion layer 10. In variations, the ratio of the plurality of drain-board core 7 dimples 8 to the plurality of rivets 11 and 14 may range between 4:1 and 10:1 depending on the application. The ratios depicted in the Figures indicate a ratio of 4:1. In many embodiments, the mechanical pullstrength strength of the drain-board core 7 and anti-abrasion layer 10 preferably exceeds 400 lbf/ft$^2$.

In embodiments, the improved waterproofing-panel assembly 15 features a geocomposite drain panel 13 that is attached to the cross-laminated film backing 6 (see FIG. 1B) using an industrial-grade chemically-compatible low-VOC adhesive (typically, the bond strength is less than 1,000 lbf/in$^2$, as applicable for non-structural adhesives). In such embodiments, the overall thickness of the improved waterproofing-panel assembly 15 is approximately 0.5 to 0.6 inches (0.062+0.40+0.062, membrane+drain-board core/filter+anti-abrasion layer).

Figure 4A:
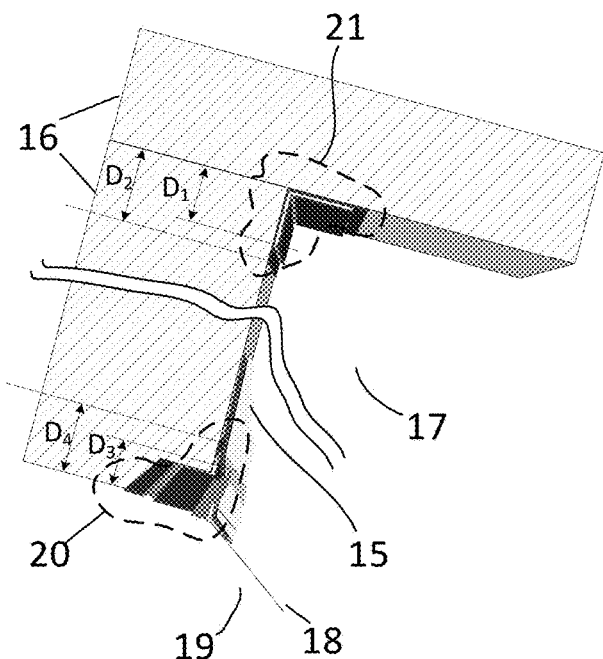
FIG. 4A depicts one embodiment of the installation details of the improved waterproofing system with inside and outside corner assemblies.
Figure 4B:
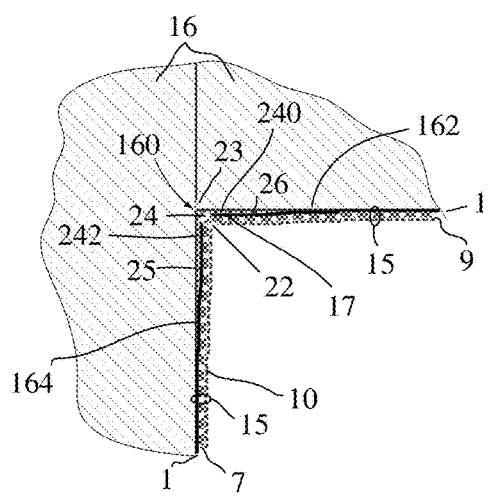
FIG. 4B depicts one embodiment of the cross-sectional details of the inside-corner assembly of an improved waterproofing system from FIG. 4A.
Figure 4C:
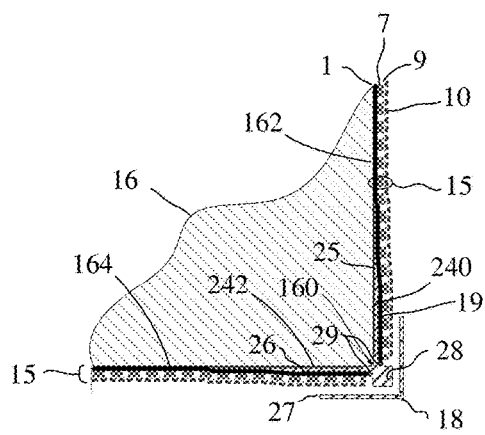
FIG. 4C depicts one embodiment of the cross-sectional details of the outside-corner assembly of an improved waterproofing system from FIG. 4A.

In even more embodiments, the improved waterproofing-panel assembly 15 is installed on concrete or cinder-block wall 16 (see FIG. 4A), while FIGS. 4B and 4C illustrate more information about outside and inside vertical corner details 21 and 20 respectively. A factory-made inside-vertical corner 17 (see FIGS. 4A and 4B) and outside-vertical corner 19 (see FIGS. 4A and 4C) allow the improved waterproofing panels 15 to be joined, preferably vertically joined, at a corner 160 of the wall 16 (see, e.g., FIG. 4C) or plurality of walls 16 (see, e.g., FIG. 4B) to create a watertight seal. In example embodiments as shown at FIGS. 4B and 4C, high-impact polystyrene cores 24 and 29 are positioned at the corner 160 which creates a first wall surface 162 and a second wall surface 164. The first and second wall surfaces 162, 164 can be at 90-degree angles, as illustrated in FIGS. 4A and 4B, or any angle used in a polygonic structure.

In still more applications, each high-impact polystyrene cores 24 and 29 has at least two polymeric (and preferably polystyrene) flaps 240, 242. The flap 240 is designed to be applied to the first wall surface 162; while the flap 242 is designed to be applied to the second wall surface 164. If the first and second wall surfaces 162, 164 are at right angles, then the flaps 240, 242 are opposed at 90 degrees. The polystyrene flaps 240, 242 are compliant and the 90-degree flap angle is easily changed to accommodate variations in the wall angle. Each flap 240, 242 is backed with a release liner 3 that exposes a pressure-sensitive rubberized-asphalt adhesive 25 to attach the vertical corner pieces 17 and 19 to the wall 16. The width of the rubberized-asphalt membrane 25 on the wall 16 side of inside and outside vertical corners 17 and 19 is about 6 inches, and this is indicated by dimensions $D_2$ and $D_4$ in FIG. 4A. There are also pressure-sensitive adhesive rubberized-asphalt strips 26 on the front surfaces of the polystyrene flap surfaces 240, 242 opposite the wall 16, which create a reinforced under-lap bond with the over-lapped rubberized-asphalt membrane 1 of waterproofing panel 15. In many variations, the width of the inside and outside vertical corner polystyrene flaps 240, 242 is about 4 inches as indicated by dimensions $D_1$ and $D_3$ in FIG. 4A, and these dimensions each represents the length of end-lap engagement between the rubberized-asphalt membranes 26 of the inside 17 or outside 19 corners and the rubberized-asphalt membrane 1 of waterproofing panel 15. In typical applications, industrial adhesive and sealant such as mastic is used to detail the ends and edges of the waterproofing membrane 1 by forming vertical canted beads 22, 28, as indicated by FIGS. 4B and 4C, respectively. Prior to the application of the inside vertical corner 17, the seam in wall 16 is sealed using an industrial polyurethane sealant 23 as indicated, e.g., in FIG. 4B. To seal the end of the drain-board core 7, factory-made outside 18 and inside 17 corner caps comprised of anti-abrasion material are placed over the detailed 90-degree joints using a pressure-sensitive adhesive with release liner 3.

Figures 5A, 5B:
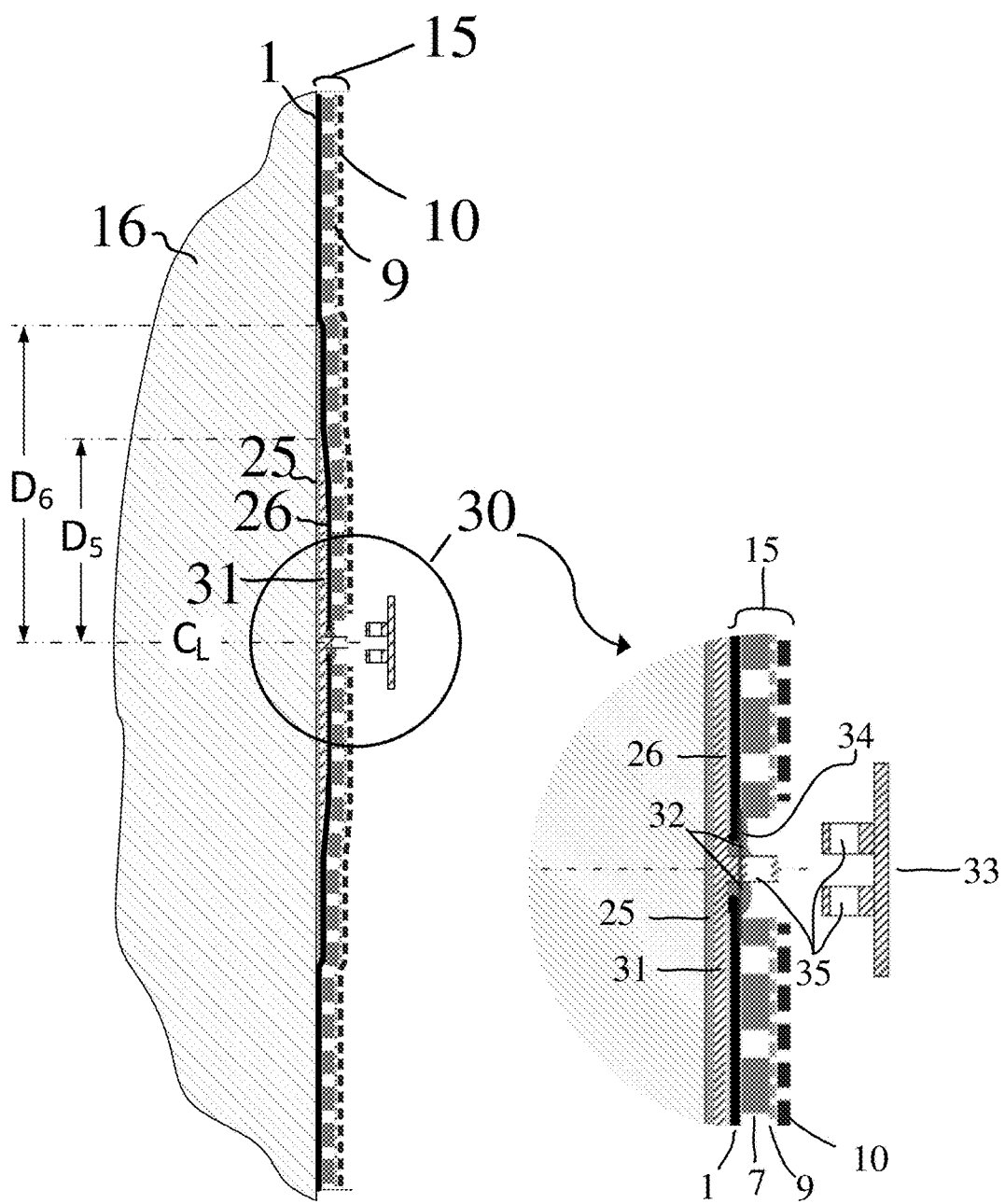
FIG. 5A depicts one embodiment of a cross-sectional view of a horizontal field joint that is used to vertically join drain panel assemblies of an improved waterproofing system end-to-end.
FIG. 5B depicts one embodiment of the detail of the horizontal field joint depicted in FIG. 5A.

In many embodiments, the improved waterproofing panel assemblies 15 are vertically joined using a seam 30 (see FIGS. 5A and 5B) between the adjacently installed waterproofing panels 15. In some variations, groups of improved waterproofing panel assemblies 15 are joined via such seams 30 in a controlled factory setting, while in other variations, adjacent improved waterproofing panel assemblies 15 are joined via such seams 30 in the field during installation at a building site. The seam 30 is closed using a factory-made horizontal field joint using a similar configuration to the inside 17 and outside 19 vertical corners as depicted in FIGS. 4A, 4B, and 4C, except the polystyrene flaps 25 are opposed at 180 degrees from each other with a length of about 6 inches as represented by dimension $D_6$ in FIG. 5A and the polystyrene flaps 25 are attached to the polystyrene core 31, which has a pressure-sensitive adhesive rubberized-asphalt backing 25 and single-sided or double-sided adhesion flaps that form water-tight interfaces to each improved waterproofing-panel assembly's 15 waterproofing membrane 1, as well as pressure-sensitive rubberized-asphalt adhesive strips 26 on the upper surface of the joint that act to reinforce the membrane 1 termination. This under-lap length is about 4 inches and is indicated by dimension $D_5$ in FIG. 5A. This configuration provides an electrical conduit 34, like a wire, to electrically connect the conductive membrane layer 5 of the composite waterproofing membrane 1 across the horizontal joint 30. Horizontal canted beads of adhesive sealant 32 such as mastic seals and protect the horizontal edges of the improved waterproofing-panel assembly's 15 waterproofing membrane 1. In variations, to provide protection after the horizontal joint has been detailed, a polystyrene cap strip 33 is installed to prevent soil infiltration into the drainage panel core, and the polystyrene cap strip 33 also provides flow channels 35 that allow a gravity-assisted water drainage flow of no less than 20 gallons/minute per linear foot across the horizontal field joint 30.

Figure 6A:
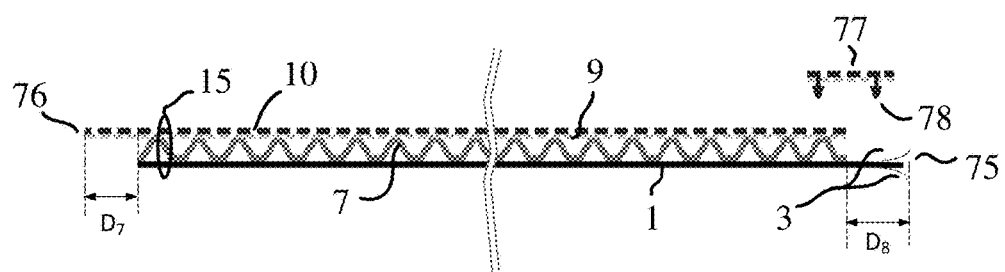
FIG. 6A depicts one embodiment of a top cross-sectional view of an improved waterproofing panel prior to installation.
Figure 6B:
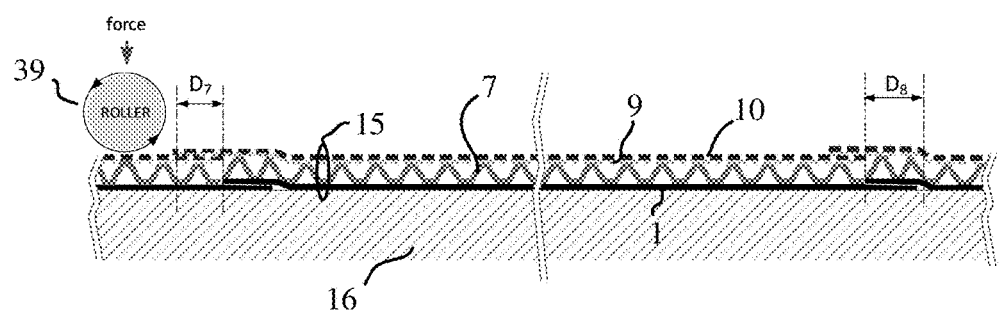
FIG. 6B depicts one embodiment of a top cross-sectional view of an improved waterproofing panel installed on a concrete wall with under and over end-lap details to horizontally adjoining improved waterproofing panel assemblies on each side.

In still more embodiments, the improved waterproofing panel assemblies 15 are horizontally joined using protruding flaps 75, 76 that overlap adjacent panels 15 (see FIGS. 6A and 6B, with FIG. 6A showing a top view of an improved waterproofing-panel assembly 15 in an uninstalled condition, and FIG. 6B showing a top view of adjacent improved waterproofing panel assemblies 15 joined together). In some variations, groups of improved waterproofing panel assemblies 15 are joined via such flaps 75, 76 in a controlled factory setting, while in other variations, adjacent improved waterproofing panel assemblies 15 are joined via such seams 75 in the field during installation at a building site. In variations, the protruding flap 75 on one side of an improved waterproofing-panel assembly 15 extends from the main lateral edge on the panel assembly 15 on one side by about 4 inches, as represented in FIG. 6B by distance $D_8$, with the pressure-sensitive rubberized-asphalt adhesive coating release liners 3 below and above the flap 75. On the other side, in variations, another flap 76 extends about 3 inches as represented in FIG. 6B by distance $D_8$ distance $D_7$ from the edge of the anti-abrasion layer 10 and filter fabric layer 9, which are attached to drain-board core 7. When the improved waterproofing panel assemblies 15 are installed on the wall 16 as illustrated in FIG. 6B, the composite waterproofing membrane 1 is under-lapped for distance $D_8$ below the adjacent panel's 15 composite waterproofing membrane 1, and the anti-abrasion layer 10 and filter fabric layer 9 is over-lapped for distance $D_7$ over the opposite adjacent panel's composite waterproofing anti-abrasion layer 10. In a typical installation, the installed waterproofing panels are rolled with roller 10 to apply pressure or other appropriate pressure is applied in order to ensure adhesion on all end-lap joints 75, 76. For covering irregular joints created by the necessity of cuts made in the field, a strip of anti-abrasion and filter fabric material 77 can be provided with a plurality of capture features 78 to engage and lock into the improved waterproofing-panel assembly's 15 anti-abrasion layer 10. Moreover, in variations, the capture feature 78 has a rounded end that will not damage the improved waterproofing-panel assembly 15 filter fabric layer 9.

Figure 7A:
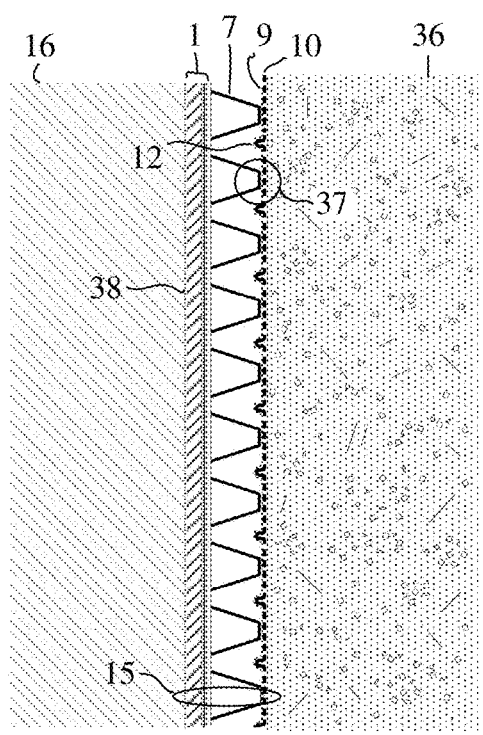
FIG. 7A depicts one embodiment of a vertical installation of the drain panel assembly of an improved waterproofing system on an existing concrete wall.
Figure 7B:
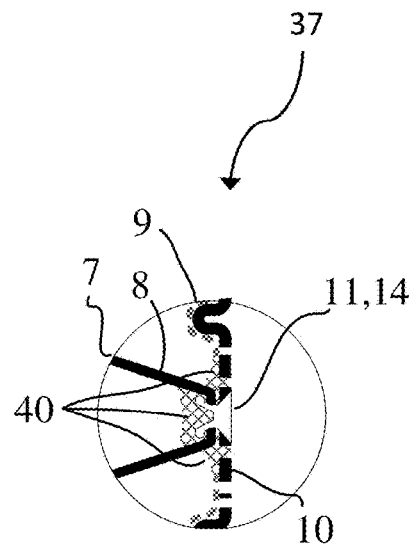
FIG. 7B depicts one embodiment of the details of the waterproof-riveting configuration between the drain panel assembly anti-abrasion layer and the dimple board of an improved waterproofing system.

In an embodiment, the in-field vertical installation of an improved waterproofing-panel assembly is depicted in FIGS. 7A and 7B, in which the concrete wall 16 and improved waterproofing-panel assembly 15 are shown in cross-section view, along with earthen back-fill 36. The cross-sectional views of FIG. 7A also shows the high-impact polystyrene drain-board core 7, the high-impact polystyrene anti-abrasion layer 10, which protects the filter fabric layer 9 during the application of earthen back-fill 36, and the transverse crease 12 feature in the anti-abrasion layer 10. Area 37 is shown in greater detail in FIG. 7B. A plurality of rivets 11 are installed 14 through the anti-abrasion layer 10 into existing holes on a fraction of the plurality of dimple tops 8 of drain core board 7. In a variation, the rivet 11 is flared under the dimple of the drain-board core 7 to firmly reinforce the attachment of the anti-abrasion layer 10, and wherein the industrial-grade chemically-compatible low-VOC adhesive 40 has been used to fill the inside end of the dimple tops 8 of drain-board core 7 to provide a leak-proof joint. Additionally, the industrial-grade chemically-compatible low-VOC adhesive 40 is used at all the dimple tops 8 of drain-board core 7 contact points with anti-abrasion layer 10. In additional variations, the ratio of the plurality of drain-board core 7 dimples 8 to the plurality of rivets 11 and 14 may range between 4:1 and 10:1 depending on the application. The ratios depicted in the Figures indicate a ratio of 4:1. In many embodiments, the mechanical pull-strength strength of the drain-board core 7 and anti-abrasion layer 10 preferably exceeds 400 lbf/ft$^2$. In many applications, the improved waterproofing-panel assembly 15 with composite waterproofing membrane 1 is applied over a conductive primer coating 38 applied to the concrete wall 16 surface. In variations, the conductive primer coating 38 meets the following criteria:

Compressive strength of about 7,800 psi ASTM D-695;
Tensile strength of 2,200-3,200 psi ASTM D-695 or ASTM D-638;
Elongation of about 2%;
Hardness Shore D of about 85 ASTM 2-2240;
Resistivity of 0.5-10.5 Mohms;
Static Charge Decay: 5,000-volt charge disperses to zero in less than 0.10 seconds;
Conductivity complies with DOD-HDBK-263 (Electrostatic Discharge Control Handbook for Protection of Electrical Parts, Assemblies & Equip.); and
Surface Resistance of <250 k ohms NFPA 99.

In some embodiments, the conductive primer coating is selected from the group of products consisting of Corobond™ Conductive Epoxy Primer available from the Sherwin-Williams Company, Stonhard™ Conductive Novolac Primer available from Stonhard, Inc., and Lexite™ Conductive Primer available from Metalcrete Industries.

Figure 8A:
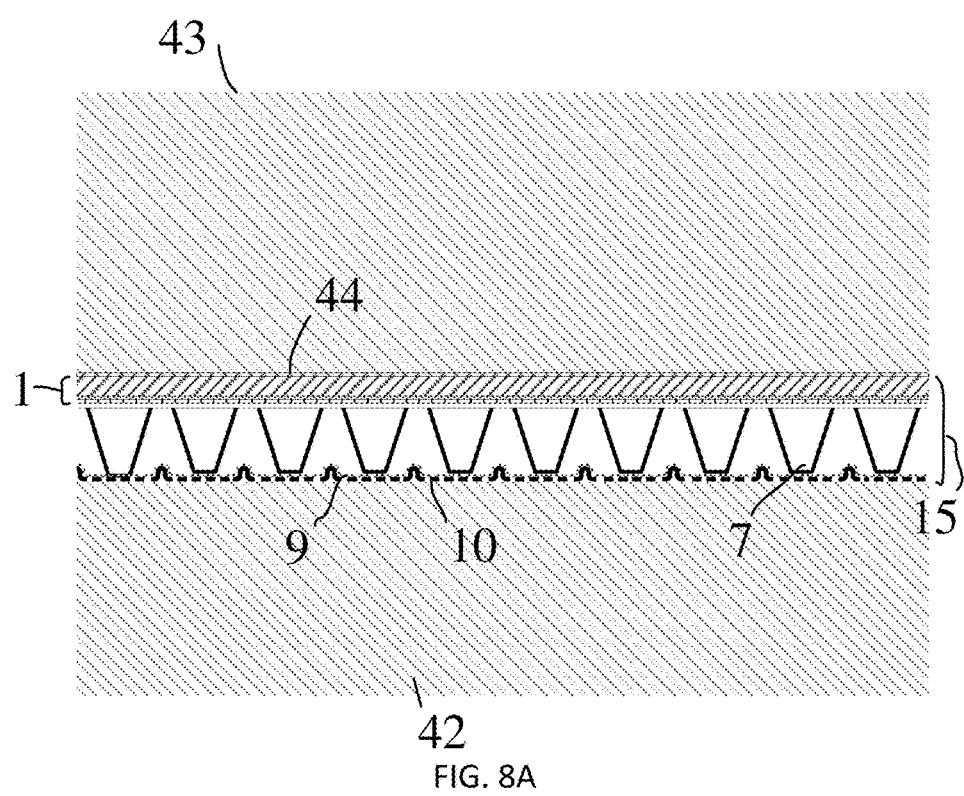
FIG. 8A depicts one embodiment of a cross sectional view of a horizontal under-slab installation of the drain panel assembly of an improved waterproofing system.

In embodiments calling for horizontal under-slab installation of the improved waterproofing panels assemblies 15, as depicted in FIG. 8A, wherein the improved waterproofing-panel assembly 15 is applied prior to the pouring of concrete floor 43 with the anti-abrasion layer 10 disposed downward in contact with the earth 42. The improved waterproofing-panel assembly 15, with composite waterproofing membrane 1 and a non-woven polypropylene fabric layer 44, faces upwards and the floor concrete 43 is poured on top of the horizontal improved waterproofing-panel assembly 15. The cross-sectional view in FIG. 8A also shows the high-impact polystyrene drain-board core 7 and the high-impact polystyrene anti-abrasion layer 10, which protects the filter fabric layer 9 during the under-slab installation.

However, in some cases for under-slab installations, the making of panel-to-panel electrical connections to support intrinsic leak detection is not practical; therefore, a modification is required. The bulk resistance of the waterproofing membrane 1 will change as a function of waterproofing panel 15 surface area (i.e., the area in contact with the substrate 43 [e.g., concrete]). This can be used to help map the topography of an installed waterproofing system, because the bulk resistance and capacitance should correlate with the areas of the panels 15 that were installed. It should be noted that these relationships apply for all installations; that is, both horizontal and vertical installations. Unlike vertical installations on below-grade walls, under-slab installations will generally have a very large area to cover, and unless a roll of waterproofing-panel assemblies 15 is very large to allow it to go between each side of the building (such rolls will usually be too large and heavy to be practical), the under-slab sections must be put down in sections, which in turn necessitates that each waterproofing-panel assembly 15 either be electrically connected to its adjacent waterproofing-panel assembly 15 or that wires from each waterproofing-panel assembly 15 be extended to the perimeter of the structure. It should be noted that employing both of these options is generally impractical. To overcome this limitation, referring to FIG. 8B, the improved waterproofing-panel assembly 15 is further configured with an upper layer of non-woven geotextile material 44 placed against the ground 42, as in FIG. 8A, except that instead of pouring the concrete under-slab 43 directly on top, a layer of wire mesh 39 is first unrolled over an integrated drain panel 13 with waterproofing membrane 1; that is the improved waterproofing-panel assembly 15. In some variations, such a wire mesh 39 can be 40 AWG (American Wire Gauge). The gauge of wire in the mesh 39 needs to be small-enough, and the mesh 39 course enough, to keep the mass of a large roll below 25 lbs. (in some applications, the roll can be 300 ft. in length by 4 ft. in width). The mesh layer 39 is extended to the perimeter of the structure. In embodiments, the fine-wire mesh 39 can be made of any highly conductive metal such as copper or stainless steel. Any electrical connections to the mesh 39 are made by simply overlapping the fine-wire mesh 39 by at least 1 ft. Another asphaltic membrane 41 is applied (that is, unrolled) over/above the fine-wire mesh layer 41. This over-covering asphaltic membrane 41 has an upper layer of non-woven geotextile 44. In many variations, the lower surface of the over-covering asphaltic membrane 41 facing the fine wire mesh layer 39 is comprised of rubberized asphalt. The total thickness 47 of the two layers of rubberized asphalt 4 can vary. The ratio of the two is not critical, as long as the total thickness 47 is at least 60 mils.

Figure 8B:
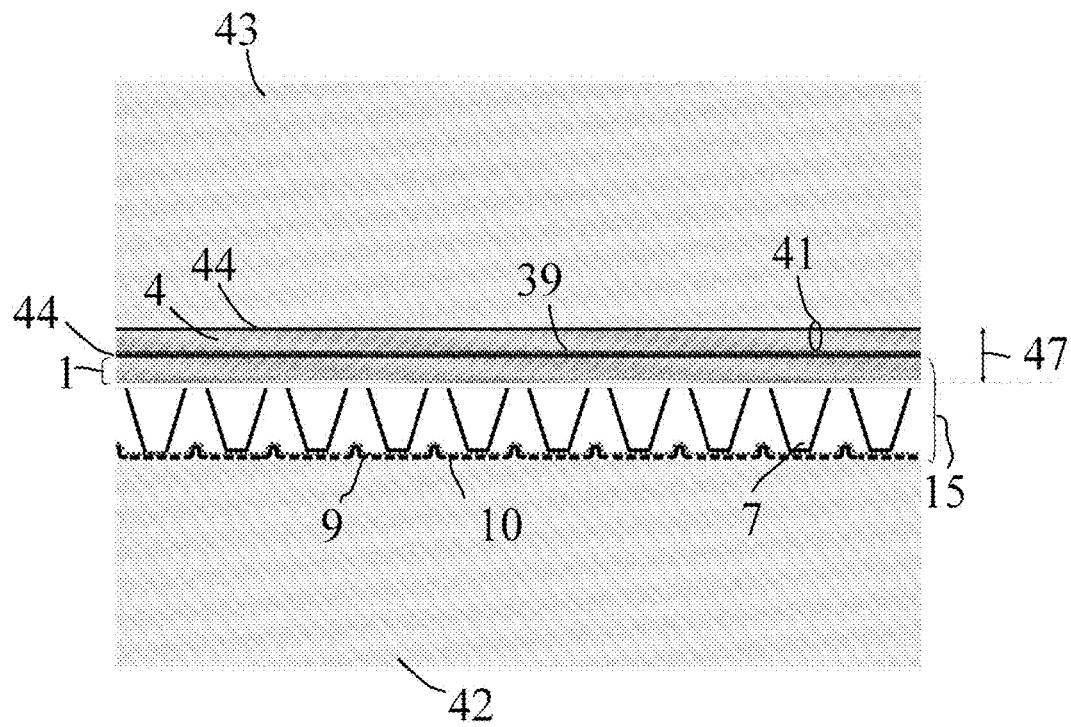
FIG. 8B depicts one alternative embodiment of a cross sectional view of a horizontal under-slab installation of the drain panel assembly of an improved waterproofing system.
Figure 8C:
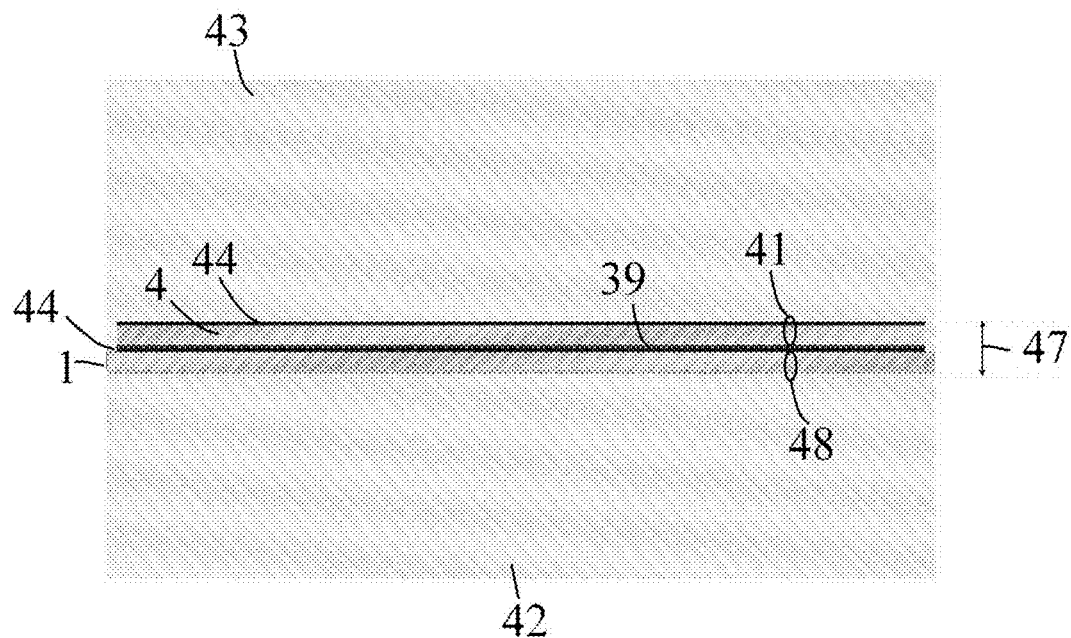
FIG. 8C depicts a variation of the alternative embodiment of a cross sectional view of a horizontal under-slab installation of the drain panel assembly of an improved waterproofing system shown in FIG. 8B.

FIG. 8C shows a variation of the embodiment of FIG. 8B with the lower waterproofing-panel assembly 15 replaced by another asphaltic membrane 48 with an upper layer of non-woven geotextile 44. The fine-wire mesh layer 39 is sandwiched between the asphalt layers 41, 48. This configuration is shown because some under-slab installations without basements (such as plazas) may eliminate the drainage panel 13. from the overall assembly 15.

In addition, the integrated drain panel with water proofing membrane 15 with intrinsic leak detection layer 5 can be used in a stand-alone under-slab application as shown in in FIG. 8B, but each end-to-end panel 15 joint will require an electrical connection to be made between the panel 15 conducting layers 5 in the field.

Figure 8D:
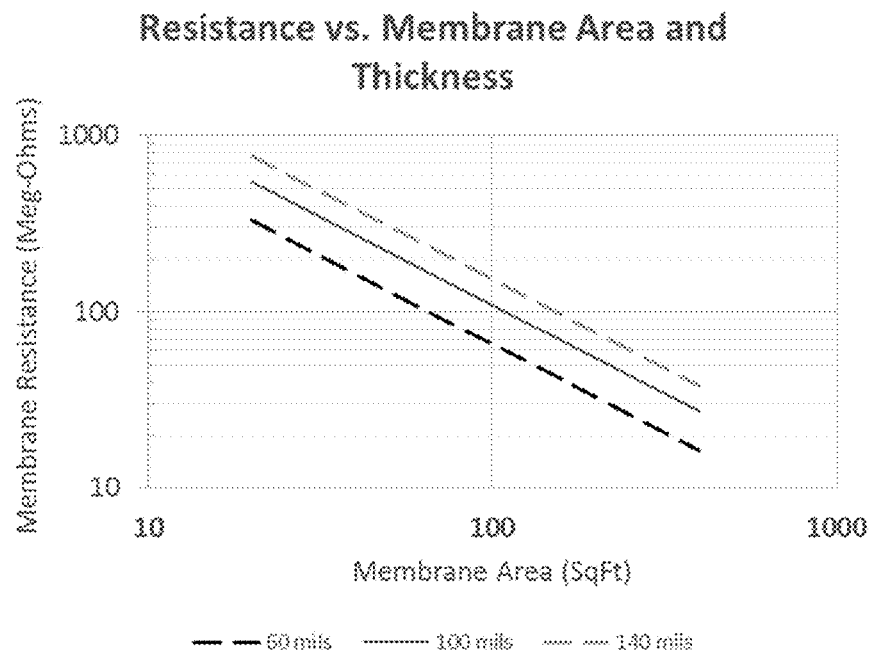
FIG. 8D depicts an embodiment of the rubberized-asphalt membrane (from FIGS. 8B and 8C) resistance characteristics, shown as a log-log relationship, for three different membrane thicknesses. These relationships apply for all installations; that is, both horizontal and vertical installations.
Figure 8E:
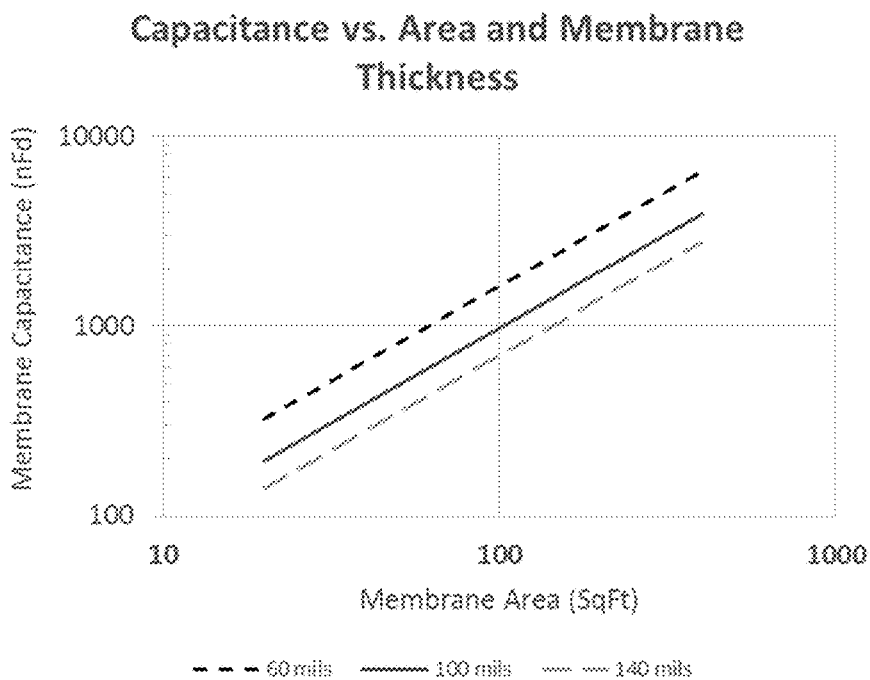
FIG. 8E depicts an embodiment of the rubberized-asphalt membrane (from FIGS. 8B and 8C) capacitance characteristics, shown as a log-log relationship, for three different membrane thicknesses. These relationships apply for all installations; that is, both horizontal and vertical installations.

FIG. 8D depicts an embodiment of the rubberized-asphalt membrane (from FIGS. 8B and 8C) resistance characteristics, shown as a log-log relationship, for three different membrane thicknesses, and FIG. 8E depicts an embodiment of the rubberized-asphalt membrane (from FIGS. 8B and 8C) capacitance characteristics, shown as a log-log relationship, for three different membrane thicknesses. It should be noted that the relationships depicted in FIGS. 8D and 8E apply for all installations; that is, both horizontal and vertical installations.

Figure 9:
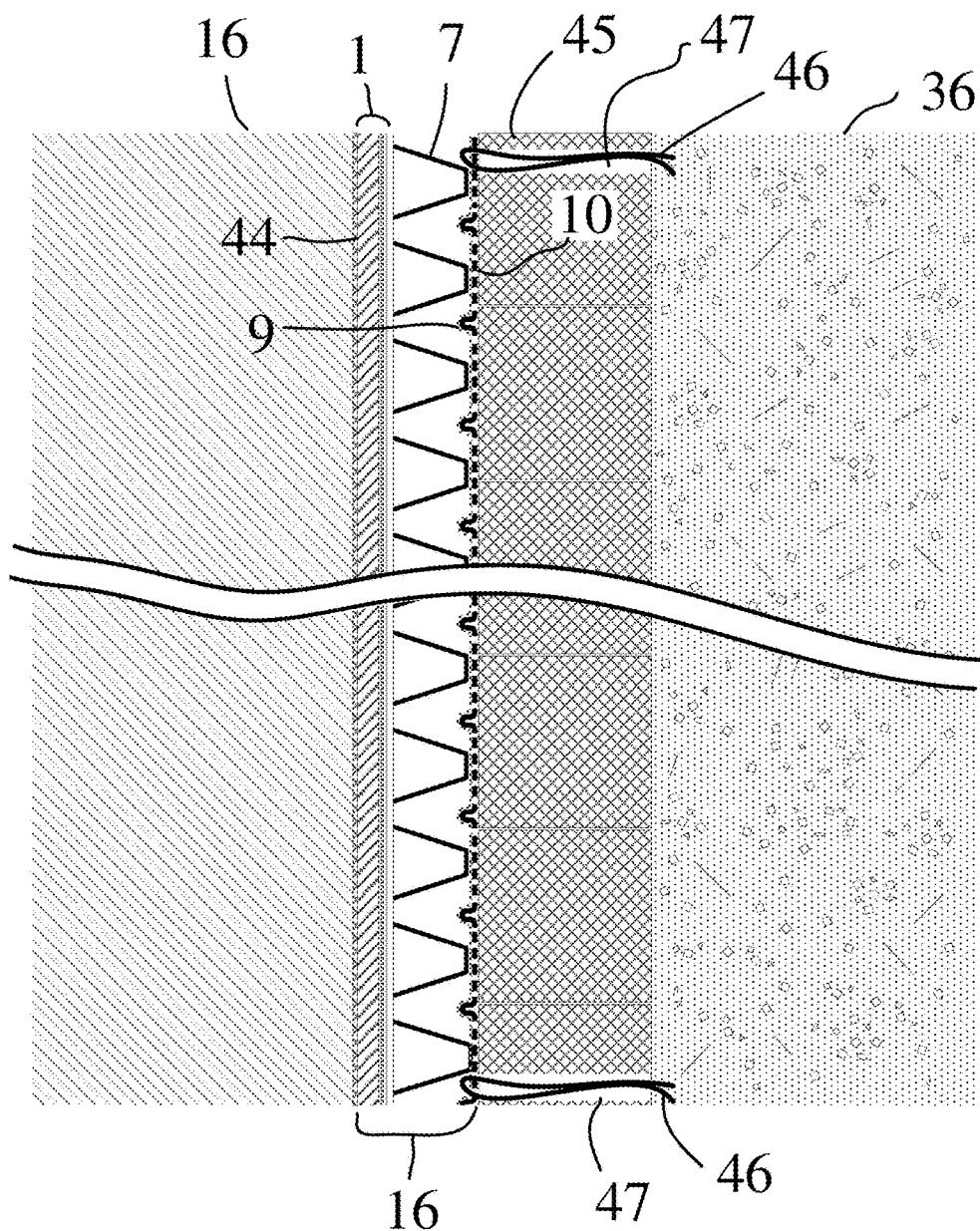
FIG. 9 depicts one embodiment of a cross sectional view of a vertical blindside installation of the drain panel assembly of an improved waterproofing system.

In vertical blindside-installation applications, such as the embodiment depicted in FIG. 9, the improved waterproofing-panel assembly 15 is applied prior to pouring the concrete wall 16 with the anti-abrasion layer 10 facing the blindside scaffolding cross members 45. The plurality of perforations in the anti-abrasion layer allow a plurality of devices 46 such as strings or tie-wraps to be used to secure the improved waterproofing-panel assembly 15 vertically against the scaffolding cross members 45 through a plurality of openings 47 in the scaffolding cross members 45, thereby decreasing (and often eliminating) the need to secure the panel to blindside scaffolding cross members 45 using penetrating fasteners such as nails or screws. The improved waterproofing-panel assembly 15 with composite waterproofing membrane 1 and a non-woven polypropylene fabric layer 44 faces towards the wall concrete 16, which is poured behind the vertically oriented improved waterproofing-panel assembly 15. The cross-sectional view in FIG. 9 also shows the high-impact polystyrene drain-board core 7 and the high-impact polystyrene anti-abrasion layer 10, which also protects the filter fabric layer 9 during the blindside installation.

Figures 10A, 10B:
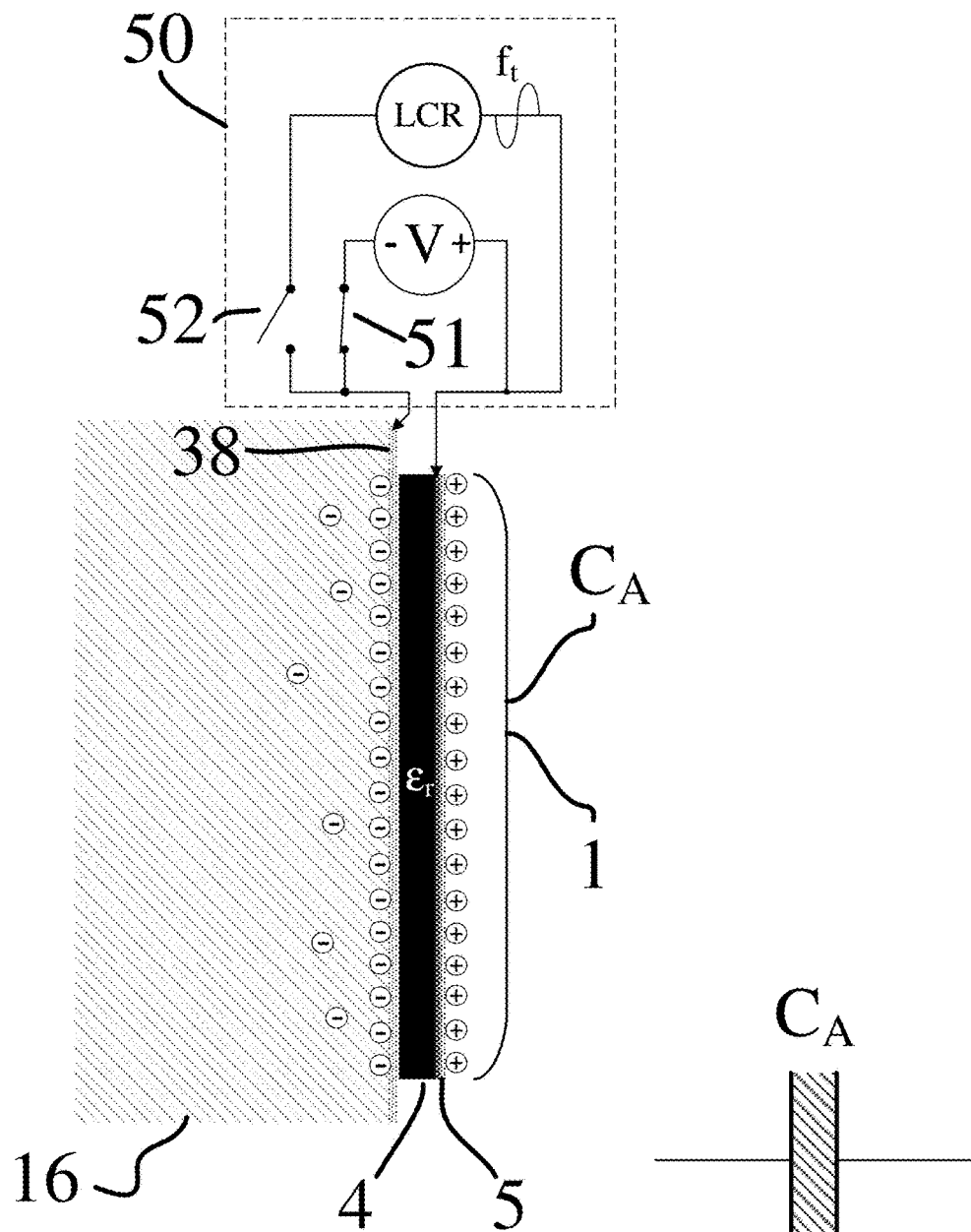
FIG. 10A depicts one embodiment of an abstract rendering of the installation verification of an improved waterproofing membrane using a capacitance measurement.
FIG. 10B depicts one embodiment of the equivalent capacitor of the configuration depicted in FIG. 10A.

In an embodiment, as depicted in FIGS. 10A and 10B, an installation of an improved waterproofing system can be quality-controlled/leak-checked using capacitance measurement on a normal waterproofing membrane 1 and substrate configuration. The composite waterproofing membrane 1 is shown applied to a vertical concrete wall 16 onto which a conductive primer 38 has been applied to the surface of the concrete wall 16. A voltage source V within the test device 50 applies a DC voltage through switch 51 between the positively charged conductive membrane layer 5, and the negatively charged conductive primer 38, effectively creating capacitor $C_A$ with dielectric permittivity $\varepsilon_r$ for the rubberized-asphalt layer 4. The equivalent electrical circuit for capacitor $C_A$ is shown in FIG. 10B.

$$C_A = \varepsilon A/d = \varepsilon_r \varepsilon_0 A/d \qquad \text{(Equation 1)}$$

Where:
$\varepsilon$=dielectric permittivity
A=area of the capacitor plates (in this case the waterproofing membrane area)
d=distance between the capacitor plates (in this case the thickness of the rubberized-asphalt membrane)
$\varepsilon_r$=relative dielectric permittivity of the rubberized-asphalt membrane, approximately 3
$\varepsilon_0$=dielectric permittivity of free space, 8.854 . . . E-12 Farads/meter When switch 51 is opened and switch 52 closed, the LCR meter in test device 50 measures the components of inductance (L), capacitance (C) and resistance (R) of the capacitor $C_A$ formed by the conductive membrane layer 5, the asphalt waterproofing membrane 4, and the substrate conductive primer 38 with applied AC voltage at test frequency $f_r$. Furthermore, it is preferable that the LCR meter have a variable test frequency $f_r$. Additionally, because the physical configuration of the composite waterproofing membrane 1, there will be relatively large values of C and R when compared to L, and the composite waterproofing membrane 1 will behave much like a capacitor with a very high ESR (Equivalent Series Resistance). The values obtained for C and R can be used to characterize the dielectric behavior of the installed composite waterproofing membrane 1. Finally, in practical applications, only the variable frequency LCR meter is necessary to make this measurement on the composite waterproofing membrane 1. The voltage source V is only provided for illustrative purposes in FIGS. 10A and 11A to show how the composite waterproofing membrane 1 forms capacitor $C_A$ by holding electrical charge.

When installation verifications are performed on systems where there are one or more defects/voids, as illustrated in FIGS. 11A through 11C, the installation verification uses a capacitance measurement on an abnormal defective waterproofing membrane 1 and substrate configuration. FIG. 11A is identical to what was described for FIG. 10A except the installation of the composite waterproofing membrane 1 has been compromised by a void area 49 between the rubberized-asphalt waterproofing membrane 4 and the wall 16 substrate conductive primer 38, creating capacitor $C_B$ with dielectric permittivity $\varepsilon_r$ for the rubberized-asphalt layer 4 and dielectric permittivity near that of free space $\varepsilon_0$ for the voided area. The equivalent capacitors for the upper area without a void $C_{B1}$, and the lower area without a void $C_{B3}$, and the center area with the void $C_{B2}$ are shown in FIG. 11B. The equivalent electrical circuit for capacitors $C_{B1}$, $C_{B2}$ and $C_{B3}$ is shown in FIG. 11C.

$$C_B = C_{B1} + C_{B2} + C_{B3} \quad \text{(Equation 2)}$$

Where:
$C_{B2}$ will always be less than the capacitance of the voided area since:

$$1/C_{B2} = 1/C_{B2a} + 1/C_{B2a}$$

or $$CB2 = CB2a\, CB2b/(CB2a + CB2b) \quad \text{(Equation 3)}$$

And:
$C_{B2a}$=the capacitor formed by the void 49 with dielectric permittivity $\varepsilon_0$
$C_{B2b}$=the capacitor formed by the rubberized-asphalt waterproofing membrane 4 with relative dielectric permittivity $\varepsilon_r$ Since the relative dielectric permittivity of rubberized asphalt has a value close to 3, and assuming the distance of the void 49 is the same as the thickness of the rubberized-asphalt waterproofing membrane 4, and assuming that the void is filled with air, then using Equation 3 above, the capacitance of $C_{B2}$ with the void 49 would be 25% of the capacitance of $C_{B2}$ without the void 49.

Factors such the distance and area of void 49 will affect this approximation, but the implication is that a void 49 of sufficient area would be detectable by measurements using an LCR meter as described above. Furthermore, a custom-designed capacitance sensing device would provide detection capability that could be optimized to the characteristics of the composite waterproofing membrane 1.

Figure 11D:
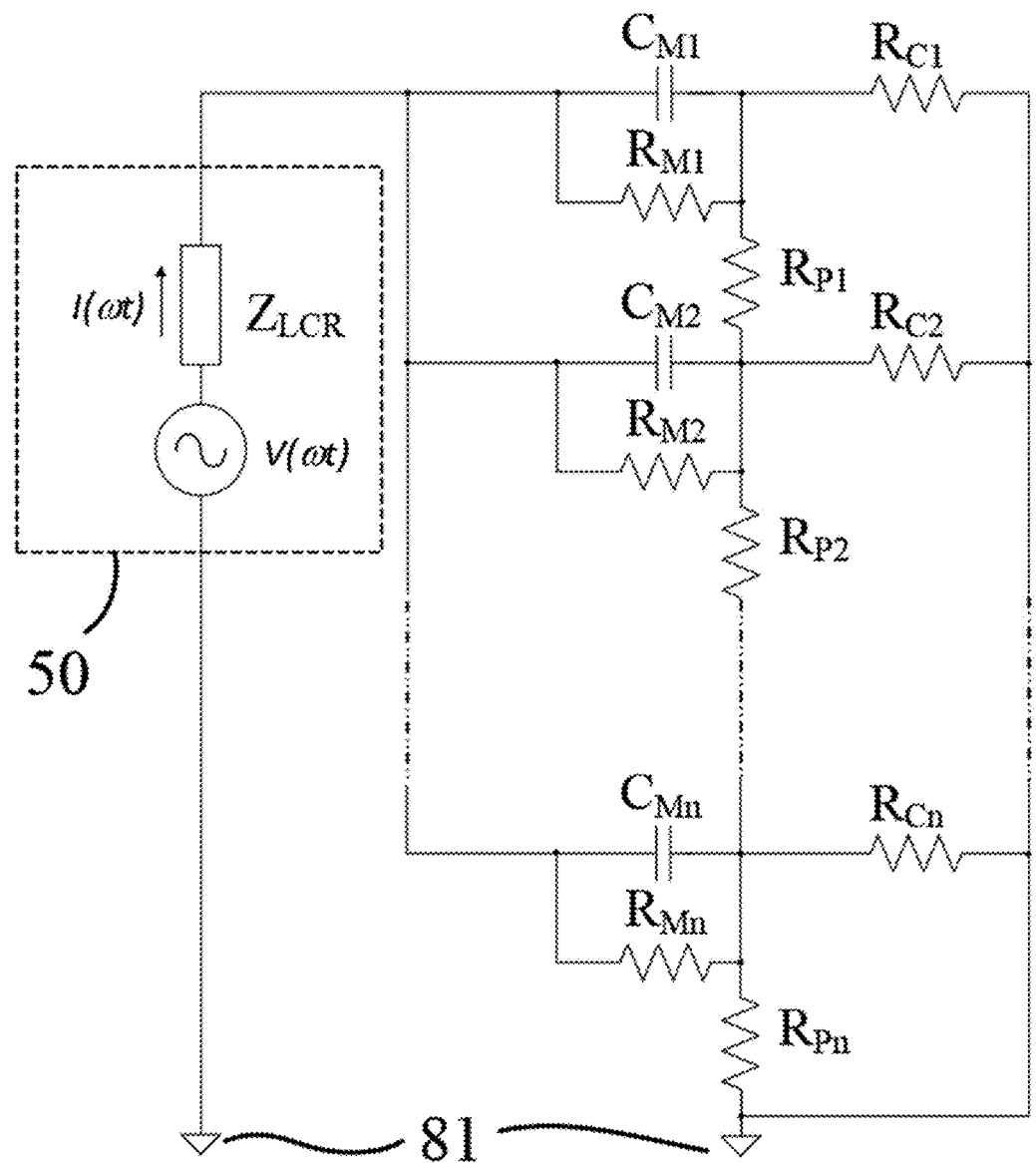
FIG. 11D depicts one embodiment of a schematic of the electrical model for the equivalent electrical circuit depicted in FIG. 11A.

The schematic in FIG. 11D illustrates one approach used to computer-model the method for measuring the electrical effects described in FIG. 11C. The composite waterproofing membrane 1 of FIG. 11A is represented by an n-element series of lumped element resistors $R_{Mn}$ and capacitors $C_{mn}$, where $R_M$ represents the surface resistivity of the electrically conductive layer 5, $C_M$ represents the capacitance of the composite waterproofing membrane 1, and 'n' represents the nth element in the n-element series. $R_P$ and $R_C$ represent the surface resistivity of the electrically conductive primer 38 and volume conductivity of the concrete wall 16, respectively. The LCR device 50 provides a variable frequency AC voltage source with the capability to measure the time-varying current $I(\Omega t)$ through test impedance $Z_{LCR}$, which introduces the test current into the common input node feeding the electrically conductive layer 5 elements $R_{M1}$, $R_{M2}$, $R_{M3}$ ... $R_{mn}$ when LCR device 50 places a test voltage $V(\Omega t)$ between the common input node and the electrical ground 81. It should also be noted that the common input node electrically represents the conductive metallic strip 79 shown in FIG. 1C.

In one embodiment, the lumped-element model was partitioned into 8×8-inch squares for the rubberized asphalt layer 4 of thickness 100 mils, and the lumped membrane capacitance element $C_{Mn}$ was calculated as shown in FIG. 8E. Additionally, the electrically conductive layer 5 is assumed to have a DC resistance at or near zero, and each lumped membrane resistance element $R_{Mn}$ was calculated as shown in FIG. 8D. The electrically conductive primer 38 layer has a surface resistivity of 50,000 ohms per square, so each lumped primer resistance element $R_{Pn}$ was set to 50 kohms, assuming that each 8×8-inch square is continuously connected at the edges. Finally, the lumped concrete resistance element $R_{Cn}$ was set to 1000 ohms based a volume resistivity for the concrete substrate 16 equal to 1000 ohms and assuming continuous planar contact between the electrically conductive primer 38 layer and the concrete substrate 16.

The frequency-response sensitivities of the gain and phase of the LCR device 50 test voltage $V(\Omega t)$ and test current $I(\Omega t)$ were investigated using this lumped-element high ESR capacitance model by changing a series of capacitive elements as described in Equation 3 above to produce changes in lumped capacitance values within the model yielding the results summarized in Table 1 below:

TABLE 1

| | | LCR Device Frequency-Response Sensitivities | | |
|---|---|---|---|---|
| Change in capacitance | Δ Gain (dB) | Δ Gain (1-Ao/Ai) | Δ Phase (degrees) | Effective magnitude of voided area 49 on 4' × 10' waterproofing panel |
| 5% | 0.346 | 1.7% | 0.60 | 2 ft.2 or an area equivalent to 17" × 17" |
| 10% | 0.707 | 3.6% | 1.27 | 4 ft.2 or an area equivalent to 24" × 24" |

A change in gain of nearly 4% with a phase angle difference of 1.27 degrees is detectable with standard LCR instrumentation, and the nearly 2% gain and 0.60-degree phase-angle change could be detectable (based on the measurement uncertainty) with an LCR instrument that provides a variation in test frequency [see datasheet for NI 4072 6 ½-Digit Digital Multimeter, 1.8 MS/s Isolated Digitizer, and LCR Meter]. Difficulties would arise from panel-to-panel installation variation that would potentially reduce the signal-to-noise ratio and, therefore, the uncertainty in the measurement, which in turn would determine the minimum size of a voided area that could be quantitatively detected reliably. However, statistical methods such as, but not limited to, to logarithmic regression (log of resistance and capacitance vs. log of installed membrane area) and residual-error analysis (difference between observation and expectation) would allow a statistically out-of-family (OOF) normalized LCR measurement to be detected, which would effectively improve the detectability of this measurement method.

The installation verification using capacitance measurement is intended to detect areas of the composite waterproofing membrane 1 are not well attached to the concrete wall 16, but not small defects such as 'fish mouths', which is sufficient because the factory integrated nature of the improved waterproofing-panel assembly 15 eliminates the possibility of defects introduced through field installation such as 'fish mouths'.

Figure 12:
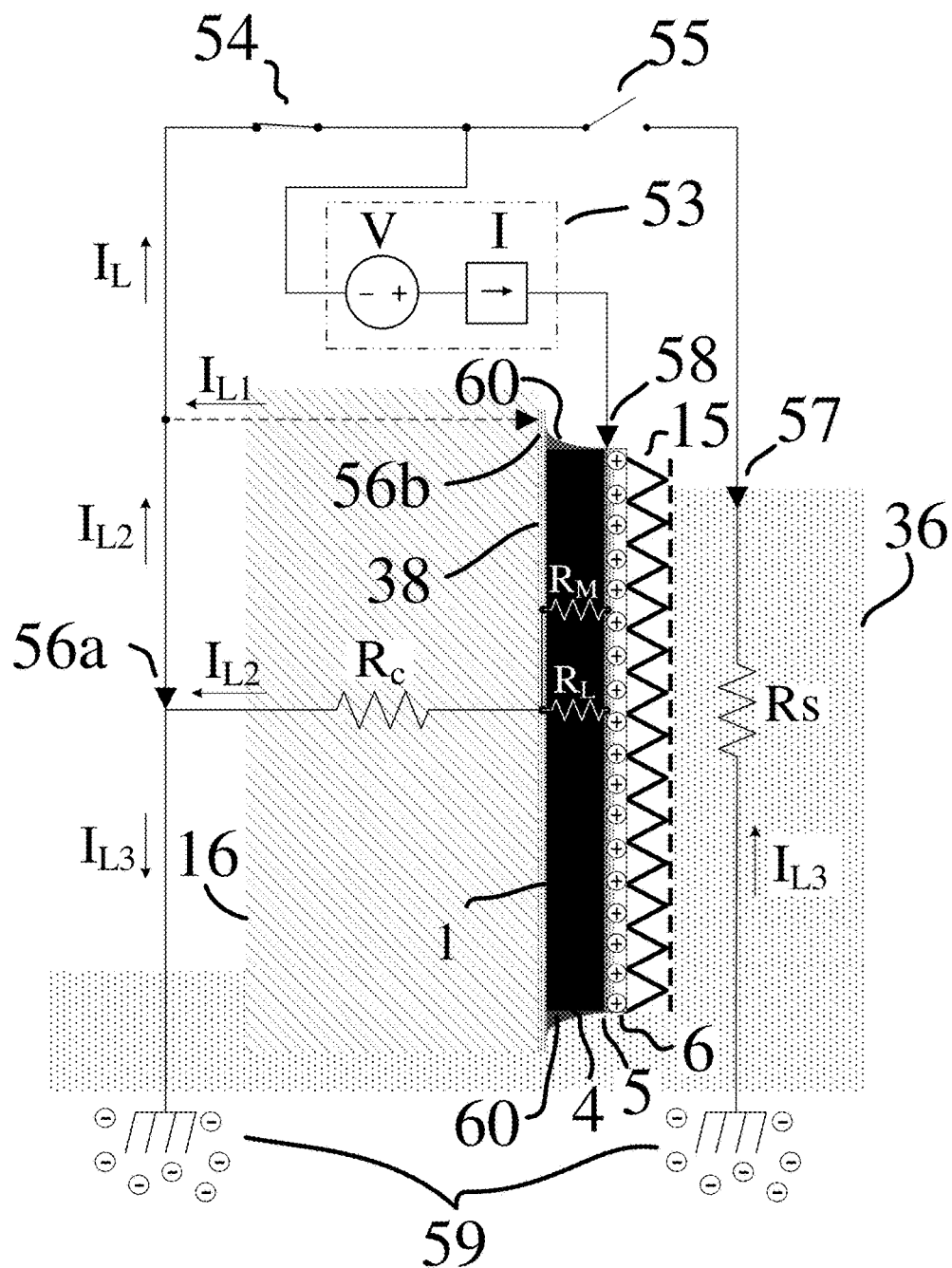
FIG. 12 depicts one embodiment of an abstract rendering of the installation verification of an improved waterproofing membrane using a leak-detection measurement using resistance.

In another embodiment, FIG. 12 provides an abstraction of a leakage-detection-verification method using electrical-resistance measurement on an installed waterproofing membrane 1. The improved waterproofing-panel assembly 15 is shown applied to a vertical concrete wall 16 onto which conductive primer 38 has been applied to the surface of the concrete wall 16. A voltage source V within the sensor device 53 applies a DC voltage through switch 54 between the conductive membrane layer 5 positive connection 58, and the negative connection 56a attached to the electrical earth ground 59 of the building structure. In one preferred embodiment, a current detector I within the sensor device 53 measures the electrical leakage current $I_{L2}$ flowing in series through the resistance $R_M$ of the asphalt waterproofing membrane 5 and then through the resistance Rc of the concrete structure 16. When a water leak compromises the composite waterproofing membrane 1, there will be a much lower water leakage resistance $R_L$ that will appear in parallel with the membrane resistance Rm. The measured leakage current $I_L$ will increase and provide indication that the composite waterproofing membrane 1 is either degrading or has failed. An alternate measurement path would be possible by attaching the negative connection directly to point 56b, which is the conducting primer 38 that is coating concrete wall 16 and measuring electrical leakage current $I_{L2}$. Additionally, by opening switch 54 and closing switch 55, electrical leakage current $I_{L3}$ could be measured, which is the return path through structure ground 59 and earth 36 at connection point 57 instead of directly from the structure's earth ground at 56a. In both cases, the structural concrete 16 provides the conduction path between the waterproofing membrane 1 and the structural earth ground 59. For reference, oven-dried concrete has a very high-volume resistivity, but once concrete has been exposed to earth and moisture, the volume resistivity of concrete drops to between 100 and 1000 ohm-meters (information obtained from U.S. Concrete Association). Soil volume resistivity varies with location, type, and moisture levels, but typically ranges between 100 and 5000 ohm-meters (see, e.g., MIL-HDBK419A: "GROUNDING, BONDING, AND SHIELDING FOR ELECTRONIC EQUIPMENT AND FACILITIES"). In both cases, due to the large contact areas of structures, the net parasitic resistances seen by the detection system are several orders of magnitude below the resistance of rubberized-asphalt membrane material, which is typically between 100 to 200 Mohms (1.+E8 to 2.+E8 ohms) (W.R. GRACE BITUTHENE® 6000 EIM SPEC SHEET).

The embodiment depicted in FIG. 12 also shows a detailing sealant material 60 covering the ends of the composite waterproofing membrane 1 which could be mastic-adhesive sealant or another suitable construction sealant, and this is necessary to prevent moisture from working its way under the edges of the rubberized-asphalt membrane 4 and degrading the bond with the concrete wall 16. Additionally, the detailing material acts as an electrical insulator and prevents stray leakage current paths. Typically, the above-ground end of the waterproofing membrane 5 is covered by a plastic or metal termination bar, which provides mechanical protection for the edge, and also serves as a cofferdam to hold the sealant material 60 when it is first applied. In the case of the electronic leak detection configuration, the termination bar would also provide the electrical connections to the ends of the metallic strips 79 in the electrically-conductive membrane layer 5 of the composite waterproofing membrane 1 for the positive connection point of the sensor device 53 and/or the positive connection lead of the LCR instrument of device 50 in FIGS. 10A and 11A, as well as hold an electrically conductive strip against the conductive primer 38 coating the concrete wall 16, which is where the negative connection of the LCR instrument in device 50 will be made, or serve as an alternate negative connection 56b for the current leakage device 53. Because of lightning strikes to buildings, which cause large amounts of electrical charge to travel to earth ground 59 through the structure's grounding system connections, high voltage surges can be present on the connection point to earth ground 56a; therefore, the current leakage device 53 would require protection from Electrical Fast Transient (EFT) that would arise due to the inductance of the structural grounding conductors.

Figure 13:
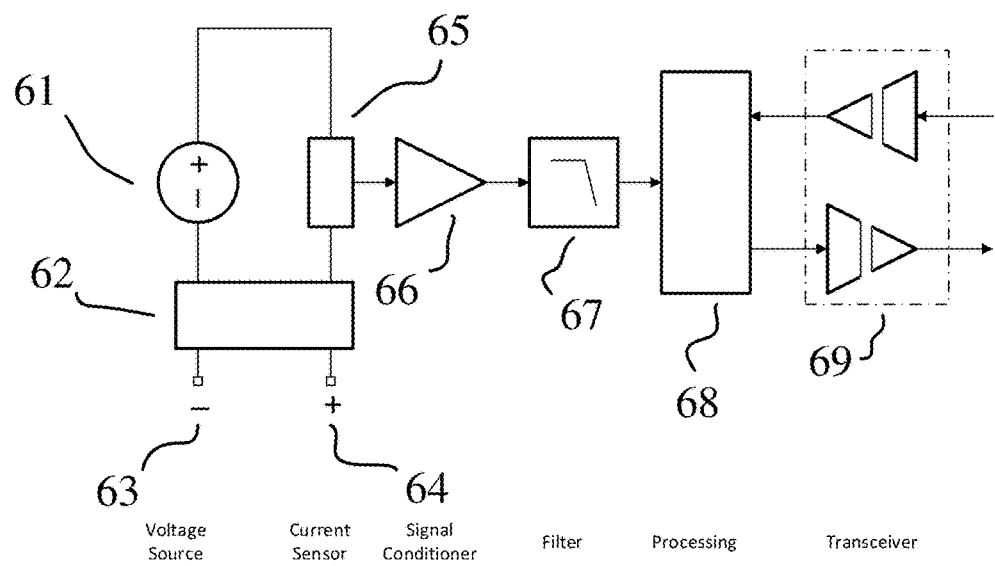
FIG. 13 depicts one embodiment of a block diagram of the electronic leak-detection method.

FIG. 13 shows the block diagram for a generic electronic device that will perform the function of the leakage detector 53 shown in FIG. 12. Voltage source 61 applies a DC potential across the composite waterproofing membrane 1 of FIG. 1B at the negative 63 and positive 64 connection points through protection circuit 62, which blocks excess external voltage that may be induced into the composite waterproofing membrane 1 by an EFT from damaging the electronic detection components. Current sensing circuit 65 measures the current level leaking through the rubberized-asphalt membrane 4 of FIG. 1B, and signal conditioner 66 amplifies and scales the output from the current sensing circuit 65 and passes the signal through a filtering circuit to remove electronic noise before the signal is read by the data processing module 68. A transceiver device 69 allows the processing module 68 to transmit leakage data to a remote receiver and also receive commands from a remote transmitter. The device represented by FIG. 13 may take several different forms including but not limited to: a handheld off-the-self ohmmeter where the operator performs the functions of the remote reader and command unit; a current-leakage detector that transmits data over a dedicated or networked hardwired interface; a remotely linked data logger; a stand-alone battery-powered recorder; a wireless device that transmits and receives information through a radio frequency link; and/or a computerized data acquisition and control system.

Figure 14A:
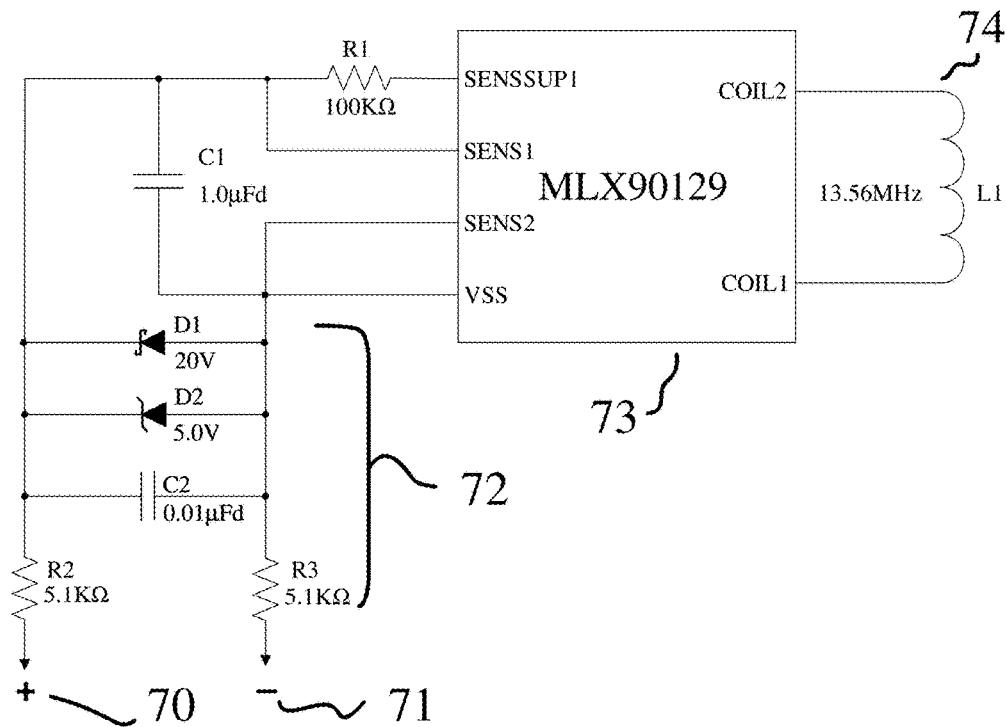
FIG. 14A depicts one embodiment of a simplified electronic schematic using an existing RFID sensor chip for an improved waterproofing system.

FIG. 14A provides the schematic design for a prototype FIG. 13 device. A Melexis Semiconductor MLX90129 13.56 MHz RFID sensor tag integrated circuit 73 operating in passive RFID mode is used to realize the FIG. 13 functional elements 61, 66, 68 and 69, while the rest of the FIG. 13 functions are created using discrete passive electronic components. The device is connected to the waterproofing membrane 1 of FIG. 1B at the negative 71 and positive 70 connection points. The FIG. 13 protection circuit 62 is realized by FIG. 14A, item 72, where Transient Voltage Suppression (TVS) diode D2 provides positive voltage protection by clamping the voltage across the positive 70 and negative 71 connection points at approximately +5 VDC, and the Schottky barrier diode D1 provides reverse polarity voltage protection for positive voltage appearing at the negative 71 connection point by clamping voltage at approximately +0.2V. Resistors R2 and R3 provide current-limiting protection when either D1 or D2 are conducting current when suppressing voltage transients. Together, R2, R3, D1 and D2 will protect the MLX90129 RFID chip 73 against an 1000V surge appearing at either the positive 70 and negative 71 connection points and will offer protection up to 10 KV for very short durations (<100 μsec). Capacitors C1 and C2 with resistors R2 and R3 provide a modest level of higher frequency noise voltage suppression. When self-powered through the L1 antenna coil 74 by an external RFID reader device, the MLX90129 RFID chip 73 provides a regulated voltage from its SENSSUP1 pin of 3.0±0.1 VDC, which appears at the positive 70 connection point when no current is flowing through resistor R1. The MLX90129 RFID chip 73 VSS pin is referenced to the negative 71 connection point. Resistor R1 and the $R_M$ resistance of the rubberized-asphalt waterproofing membrane 4 in FIG. 12 form a voltage divider, which converts the leakage current through the rubberized-asphalt waterproofing membrane 4 to a voltage between differential input pins SENS1 and SENS2 of the MLX90129 RFID chip 73, where an internal signal conditioning circuit provides the voltage to the processing unit of the MLX90129 RFID chip 73.

Figure 14B:
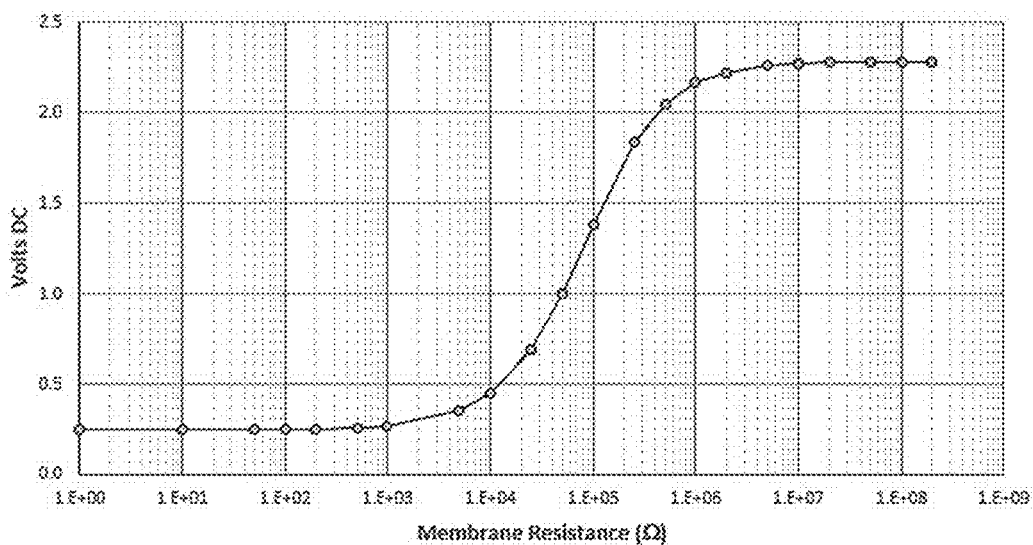
FIG. 14B depicts one embodiment of a graphical representation of the output response for simplified electronic schematic using an existing RFID sensor chip for an improved waterproofing system depicted in FIG. 14A.

FIG. 14B shows the voltage relationship between rubberized-asphalt waterproofing membrane 4 resistance and the Vsense (SENS1-SENSE2) DC voltage. Notice that at 200 Mohms (2.E+08 ohms) the Vsense voltage is approximately 2.28 VDC, and then drops rapidly when the rubberized-asphalt waterproofing membrane 4 resistance changes between 1 Mohm (1.E+06 ohms) and 1 Kohms (1.E+03 ohms) leveling off at approximately 0.25 VDC.

Because this device is intended to detect a leakage of water through the rubberized-asphalt waterproofing membrane 1, this response characteristic provides a satisfactory leak-detection output. The circuit configuration shown in FIG. 14A could be modified to provide more instrumentation-like ohmmeter capability, but at the expense of greater power draw from the L1 antenna coil 74, which would act to reduce the range from which the reader could obtain information. Using back scattering, the voltage value measured by the MLX90129 RFID chip 73 between its SENS1 and SENS2 pins, is clocked back to the external RFID reader device through the RF link as an encoded serial digital signal. The MLX90129 RFID chip 73 will respond to commands transmitted by the external RFID reader device and will transmit its unique ID, the voltage across SENSE1 and SENSE2, or the reading from an internal temperature sensor embedded within the chip. Because the MLX90129 uses anti-collision technology, multiple MLX90129 devices can be simultaneously interrogated by a single external RFID reader device.

When assigned to an improved waterproofing-panel assembly 15, the MLX90129 device associated with that particular panel will be identified by the unique ID code stored in the MLX90129 RFID chip 73 that provides a specific address for each panel 15 in a waterproofing installation, from which data can be acquired and recorded for future reference. In a final product configuration, the RFID sensor tag represented in FIG. 14A will be approximately the size and shape of a credit card, with the antenna 74 taking up most of the area. The MLX90129 RFID chip 73 operates in the 13.56 MHz Industrial Scientific and Medical (ISM) worldwide band and allows a remote reader to obtain data from a distance between 1 and 3 meters. With the configuration shown in FIG. 14A, and with the MLX90129 RFID chip 73 external memory and other non-essential devices either not installed or disabled, the range is closer to 3 meters with the proper antenna orientation. This will enable an operator with a hand-held reader with data-storage capability to walk beside the building foundation and gather waterproofing system verification data keyed by the RFID address which will be tied to waterproofing-panel 15 location. If a RFID leak sensor tag is used that operates in the ISM 902928 MHz frequency range, the range would be extended up to 12 meters, which would enable either a remotely located or several remotely located fixed position readers to be used for continuously gathering verification data from the waterproofing system.

Turning back to leak-detection capabilities for the under-slab installations depicted in FIGS. 8A-8C, which can also be applied to vertical installations as well, FIG. 8D plots the resistance of the rubberized-asphalt membrane 41, 48 as a function of the membrane surface area for three different membrane thicknesses. This relationship is calculated using Pouillet's Law, using values for Grace Bituthene 6000 EIM (W. R. Grace, 110-BIT-3E, Grace Waterproofing Systems: Bituthene® 6000 EIM, Singapore: W. R. Grace (S) Pte Ltd, 2014.), typical performance properties, where volume resistivity=$4\times10^{13}$ ohms-cm:

$$R_{membrane}=(\text{Resistivity}\times\text{thickness (cm)})/A_{membrane} \text{ (cm}^2\text{)} \quad \text{(Equation 3)}$$

Where:
$R_{membrane}$=Resistance of the rubberized-asphalt membrane
$A_{membrane}$=Surface area of the rubberized-asphalt membrane FIG. 8D depicts an embodiment of the rubberized-asphalt membrane (from FIGS. 8B and 8C) resistance characteristics, shown as a log-log relationship, for three different membrane thicknesses, and FIG. 8E depicts an embodiment of the rubberized-asphalt membrane (from FIGS. 8B and 8C) capacitance characteristics, also shown as a log-log relationship, for three different membrane thicknesses. It should be noted that the relationships depicted in FIGS. 8D and 8E apply for all installations; that is, both horizontal and vertical installations.

Stand-Alone Drain Panel with Intrinsic Leak Detection

In addition to membrane-applied or sheet-applied waterproofing barriers, there are also fluid-applied barriers used in the building-construction industry. Below-grade, fluid-applied (that is, pre-applied to the structural substrate, such as a concrete) waterproofing membranes make up a substantial portion of the commercial-construction market, especially in the case of residential structures. Examples would include, but are not limited to, the following:

Barricoat-R, manufactured by Carlisle Coatings & Waterproofing. This product is a roller-applied, water-based, asphalt emulsion modified with a blend of synthetic rubbers and special additives;

CCW-525 and CCW-525R, manufactured by Carlisle Coatings & Waterproofing. These products are liquid-applied, single-component, moisture-cured, elastomeric modified polyurethane that cures to form a flexible, monolithic, waterproof membrane on vertical or horizontal surfaces below grade;

CCW-703, manufactured by Carlisle Coatings & Waterproofing. This product is a liquid-applied membrane is a two-component polyurethane waterproofing system;

Procor®, manufactured by GCP Applied Technologies, Inc. This product is a two component, synthetic-rubber, cold-vulcanized, fluid-applied waterproofing membrane. It cures to form a resilient, monolithic, fully bonded elastomeric sheet; and TREMproof 201/60, manufactured by Tremco Inc. This product is a high-solids, VOC compliant, modified polyurethane waterproofing membrane.

To add a leak-detection capability to fluid-applied-type of below-grade waterproofing installation requires that the leak-detection mechanism be moved from the waterproofing membrane 1 to the drain panel 7.

Figure 15A:
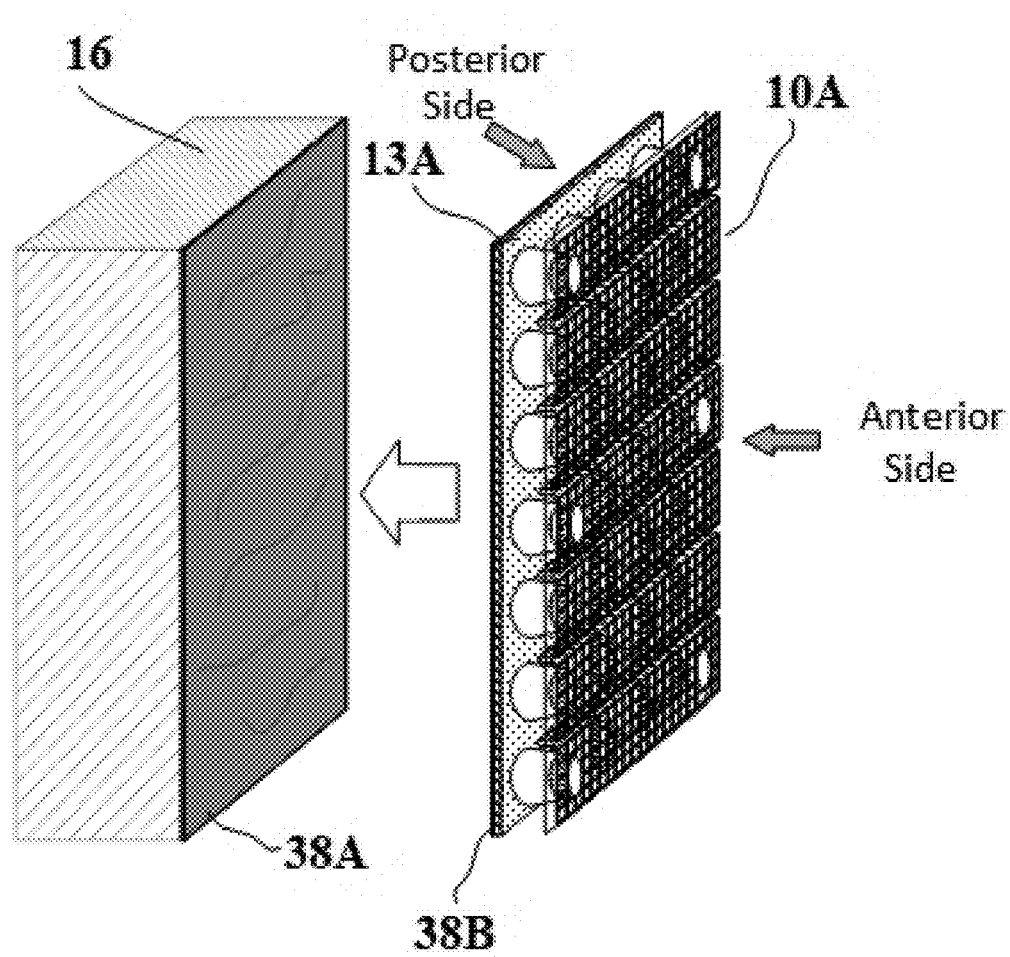
FIG. 15A depicts one alternative embodiment of an exploded view of a corner section the improved waterproofing panel membrane with its various components, wherein this particular embodiment also features a fluid-applied membrane.
Figure 15B:
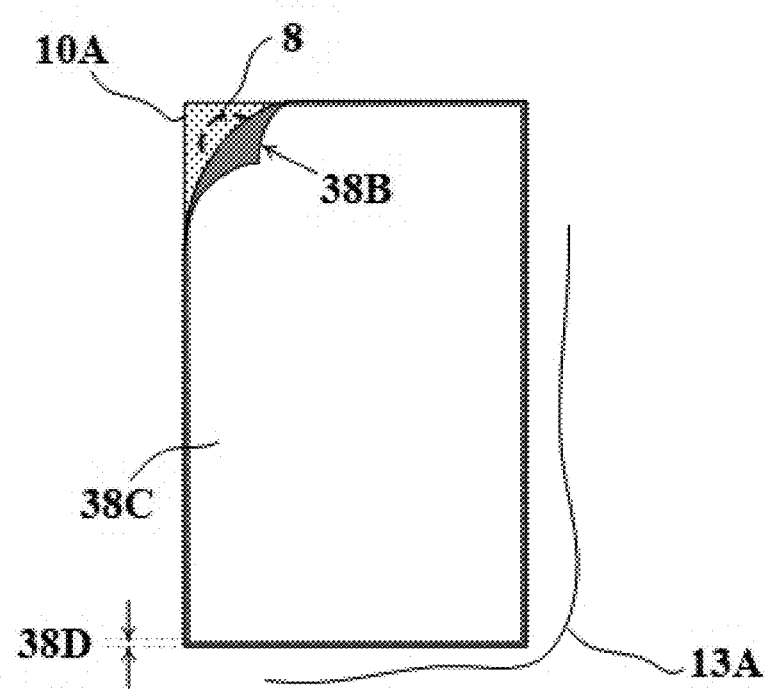
FIG. 15B depicts a posterior view of FIG. 15A's alternative embodiment of an exploded view of a corner section the improved waterproofing panel membrane with its various components, wherein this particular embodiment also features a fluid-applied membrane.
Figure 15C:
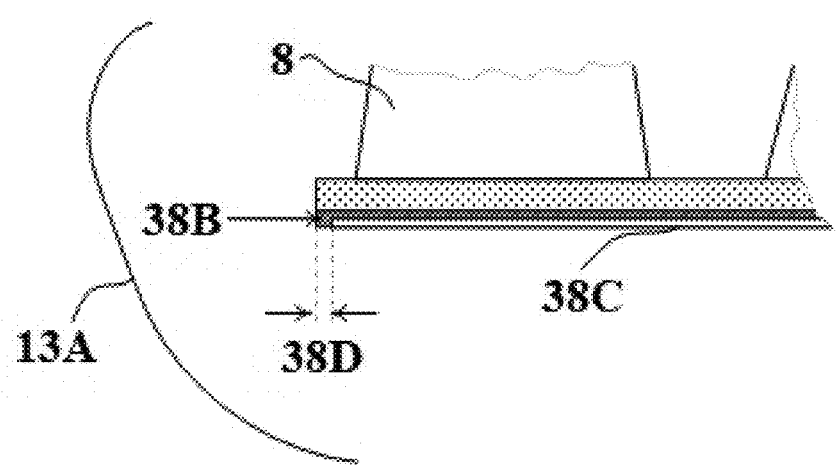
FIG. 15C depicts a side cross-sectional view of FIG. 15A's alternative embodiment of an exploded view of a corner section the improved waterproofing panel membrane with its various components, wherein this particular embodiment also features a fluid-applied membrane.

Refer to FIGS. 15A-15C. In this particular embodiment, the improved waterproofing-panel assembly features a variation of the drain panel 13A that includes a filter fabric and anti-abrasion layer 10A and an added electrically conducting layer 38B that provides the leak-detection capability. For purposes of this discussion, the posterior side of the integrated drain panel with intrinsic leak detection 13A is the surface that is applied to the substrate 16, and the anterior side of the integrated drain panel with intrinsic leak detection 13A is the surface that has the anti-abrasion layer 10A facing the earthen backfill. The structure substrate 16 is shown with a fluid-applied membrane 38A using a product selected from one of the examples listed above, or a similar commercially available product. The integrated drain panel with intrinsic leak detection 13A is applied to the fluid-applied membrane 38A using an appropriate adhesive (already discussed, supra) or as recommended by the fluid-applied membrane manufacturer.

FIG. 15B depicts an embodiment of a posterior-view section of the integrated drain panel with intrinsic leak detection 13A with the added electrically conducting layer 38B partially peeled away revealing the drain panel subassembly 13A. In variations, the electrically conducting layer 38B is made from a high-density polyethylene (HDPE), cross-laminated film backing with an electrically-conductive metal film or foil or wire mesh 38C bonded to the posterior side, henceforth referred to as the electrically-conductive metal element 38C. The electrically-conductive metal element 38C is intended to not extend all the way to the edge of the drain panel 13A; rather, the electrically-conductive metal element 38C is recessed back approximately 0.125 inches 38D. This feature serves to preserve electrical insulation at the edges of the integrated drain panel with intrinsic leak detection 13A. In variations, the HDPE cross-laminated film backing is bonded to the drain panel subassembly 13A with an industrial-grade chemically-compatible low-VOC adhesive 40. Similarly, in some applications, the electrically-conductive metal element 38C is bonded to the HDPE cross-laminated film backing with an industrial-grade chemically-compatible low VOC adhesive 40. It should be noted that if an integrated drain panel with intrinsic leak detection 13A is cut for fit in the field, then the cut edge must be detailed (covered) with a detailing sealant material 60 prior to assembly.

FIG. 15C depicts an embodiment of a cross-section-view of the integrated drain panel with intrinsic leak detection 13A with the added electrically conducting layer 38B containing an electrically-conductive metal element 38C. For reference, the drain panel subassembly 13A is shown with dimples 8 partially cut-away in this view. In variations, the core of the electrically conducting layer 38B is made from the HDPE cross-laminated film backing containing an electrically-conductive metal element 38C bonded to the posterior side. In some applications, the electrically-conductive metal element 38E is not intended to extend all the way to the edge of the drainage panel 13A; rather, the electrically-conductive metal element 38C is recessed back approximately 0.125 inches 38D. This feature serves to preserve electrical insulation at the edges of the integrated drain panel with intrinsic leak detection 13A. In more applications, the HDPE cross-laminated film backing core of the electrically conducting layer 38B is approximately 5 mils thick. Typically, the electrically-conductive metal element 38C is either a metallic film approximately 2 to 3 mils thick, or a 40 AWG metal wire mesh that is approximately 25% filled.

In embodiments, the electrical layer in the integrated drain panel with intrinsic leak detection 13A is electrically terminated in a similar manner to the termination of the waterproofing-panel assembly 15 in other embodiments, described supra, where it can be measured by external instruments such as an LCR meter and ohmmeter/multimeter. The electrical-leakage current, whether AC or DC, between the electrically conducting added layer 38B and the substrate 16 may be measured as an indicator of moisture infiltration through the waterproofing membrane 1. In variations, an installed specially-designed RFID tag (encapsulating the function of the instrumentation mentioned above) at the electrical termination, along with an RFID reader, may be used to allow remote sensing of the condition of the waterproofing installation to take place as described for the waterproofing-panel assembly 15 in other embodiments, supra. The side-to-side and end-to-end joining of the integrated drain panels with intrinsic leak detection 13A is identical to that described for the waterproofing-panel assembly 15 already described, supra.

It should be recognized that those skilled in the art of electronic design will be able to create many different leakage detection circuit sensor configurations with a variety of remote readers that will provide the functionality of the device shown in FIG. 13. Furthermore, it would also be possible to combine the functions of the frequency optimized LCR device described in FIG. 11A with the leak detection device of FIG. 13.

IV. A Method for Manufacturing and Installing an Improved Building Foundation Waterproofing and Drainage System With Intrinsic Leak Detection Capabilities This Section IV is directed to an improved process for manufacturing and installing an improved waterproofing and drainage system with intrinsic leak detection for use in building structures, such as vertical and horizontal foundational structures that are disposed below ground, the improved system depicted in FIGS. 1A though 15C and further described in Section III, supra, the current state of the art process being depicted in FIGS. 16A-16B, and the improved process being depicted in FIGS. 17A-17B.

Below-grade commercial waterproofing systems, as represented by the current-art installations currently available in the market, are engineered to protect below-ground structures and their contents from the infiltration of ground water. These prior-art waterproofing systems, however, contain potential failure modes that arise through the system manufacturing and configuration, as well as through the installation process. These failure modes can be identified and the associated effects quantified using a process Failure Modes and Effects Analysis (FMEA).

Typical Prior-Art Fabrication-and-Installation Process

The typical example of the current state of the art for the installation of existing below-ground waterproofing systems for buildings is depicted in FIGS. 16A-16B, which is followed for most current-art systems. The overall current-art process is outlined in a flow diagram in FIG. 16A, while the key process steps in FIG. 16A are diagramed in FIG. 16B (a corner fragment is shown, with the drawing not to scale). Installation of waterproofing on an existing-vertical-foundation-wall case applies for this example (i.e., not blindside or under-slab installation cases). Table 2, below, describes the process steps in a typical current-art configuration and installation:

TABLE 2

Current-Art Process-Step Description (See FIGS. 15A-15B)

| ID | Process Step | Description |
|---|---|---|
| A | Start Installation | The Architectural Specification N (unique for each construction project) defines the waterproofing materials and general installation requirements. Contractors for installation are chosen based on the contractor's certifications O and experience. |
| B | Prepare Substrate in Field | Level installation surfaces, remove rough spots that could damage the membrane. |
| C | Prime Substrate in Field | Apply primer coating (surface is enhanced for optimal membrane adhesion). |
| D | Install Membrane in Field | Remove membrane release liner and apply membrane to the substrate. |
| E | Detail Membrane as required | Edges, joints, and seams are filled using sealant. |
| L | Inspection On-Site | Waterproofing system manufacturer's on-site representative ensures: The recommended installation process has been followed by the contractor (warranty certification requirement). The membrane installation meets quality requirements. A sample test (e.g. pull test) may be required (as defined by the specification). |
| F | Apply Adhesive | Adhesive is applied to the membrane. |
| G | Install Drainage Board | The drainage board is affixed to the membrane with the adhesive. |
| H | Verify Installation | Verification (prior to backfilling): The manufacturer's representative verifies that the recommended drainage board installation process has been followed by the contractor (warranty certification requirement) and the system installation meets quality requirements (good drainage board adhesion, proper overlaps, no tears in filter fabric, etc.) using visual methods and audit of construction records. The contractor attempts to verify that the system installation will not leak; options for testing the leak-proof integrity are limited due to the configuration of the system (e.g. vertical installation instead of horizontal). Often, the quality can only be assessed qualitatively, primarily through visual inspection and with onsite audits during the installation phase. |
| I | On-Site Inspection | On-site inspection; test for warranty. |
| J | Bury Installation | Earthen backfill is used to bury the installation below ground. |
| K | Installation Complete | The waterproofing system manufacturer's warranty period begins. |
| M | On-Site Inspection | On-site inspection; test for warranty. |

Besides being inefficient, the above current-art fabrication-and-installation process discussed in Table 2 involves many in-filed steps that further introduce opportunities for the introduction of installation errors/defects that may not be detected, if at all, until much time, materials, and efforts have been expended. In the event of the detection of such errors/defects, additional time-consuming and expensive in-field remediation must then be initiated.

Improved Fabrication-and-Installation Process Using FMEA Principles

A Failure Mode and Effects Analysis (FMEA) is a systematic group of activities intended to:
  Identify and evaluate the potential modes of failure of a product and/or process, and the associated effects which result from these failures;
  Provide an estimation for the probability of the failure occurrence and the severity of the failure effect;
  Identify actions that could eliminate or reduce the occurrence of the failure modes and/or mitigate the failure effects; and
  Document the design and/or process and how the product or process can be improved.

FMEA is a standard tool used by engineers during design analysis and manufacturing process development; the FMEA discipline was an innovation of the aerospace industry in the mid-1960s.

Appendix A provides a formal process FMEA worksheet, which is separated into two tables, each associated with the same general process steps. The potential failure modes of the process described above in FIGS. 16A-16B, and Table 2, are listed on each line of the FMEA worksheet; the FMEA steps are contained in the columns from left to right (in their order of progression). The key for each category (Severity $S_o$, Occurrence $P_o$ and Detectability $Pd_o$) appear below the FMEA tables shown in Appendix A. The reduced number of category levels (five instead of 10) follow the approach typically used for medical-devices and are favored for a more qualitative FMEA (i.e., when actual process information, such as hard failure rates for each operation, are not available).

A brief description of the FMEA is provided in the bulleted list below. The information from the first entry line of the FMEA (i.e., Potential Failure Mode B.1) is provided after each FMEA step description as an example.
  ID/Process Step: Each failure mode is assigned an identification (e.g. "B.1"=Failure Mode 1, of Process Step B), and that process step is listed (e.g., "Prep Substrate").
  Potential Failure Mode: The potential failure mode appears (e.g., "Void"=a depression in the surface of the substrate).
  Potential Failure Effect: The potential effect caused by the failure mode is given (e.g., "Membrane Non-Adhesion"=because of the depression in the substrate, the membrane adhesive will not function as intended).
  Severity $S_i$ (SEV): The initial assessment for the severity of the potential failure effect (e.g., "3"=is a marginal severity category, where the failure could result in damage to structural contents, compromise structural usage, and cause immitigable environmental damage (e.g., internal wetness, high humidity, etc.). MIL-STD-882D has been adapted to prescribe five escalating categories of Severity: 1. Nuisance (The failure does not affect product quality, but is inconvenient to the user/customer, causing things such as increased costs due to rework, construction delays, and post-installation repairs); 2. Negligible (The failure could result in minimal compromise of structural usage, such as minor building environmental damage [e.g., dampness]); 3. Marginal (The failure could result in damage to structural contents, compromise structural usage, and/or mitigatable environmental damage [e.g., internal wetness and/or high humidity]; 4. Critical (The failure could result in potentially permanent damage to structural contents, structural non-usage, and/or reversible environmental damage [e.g., standing water and/or toxic mold formation]; and 5. Catastrophic (The failure causes permanent damage to structural contents, structural damage or failure, and/or severe or irreversible environmental damage [e.g., toxic mold spread/contamination]).

Potential Cause(s) of Failure: The possible failure causes are provided (e.g., "Improper/poor method by contractor" implies that this would only happen if the contracting personnel make a mistake).

Occurrence $P_i$ (OCC)*: The initial assessment for the likelihood for the occurrence of the potential failure effect (e.g., "3"=is a medium occurrence frequency, where this type of failure would be expected to happen 1 out of 80 times). The categories are: 1 for "Very Low", 2 for "Low", 3 for "Medium", 4 for "High", and 5 for "Very High". It should be noted that a building's below-ground waterproofing system may have hundreds of waterproofing panels installed, so for the purposes of this process FMEA, the occurrence likelihood applies to the entire installation at process Operation H (Verification) and afterwards, and to each individual panel for the process operations prior to H. This may be overly conservative because there will be potentially thousands of chances for a defect to occur within a single waterproofing system (and perhaps tens-of-thousands of chances for very large below-grade installations), which implies that the probability of occurrence must be low (<1 in 1,000) if each defect is considered as an individual occurrence in order to give the overall installation-level defect occurrence likelihood values of 1 in 20 or better.

Current Controls: These list the method used by the process to prevent this type of error from perpetuating through all the process steps to the end; e.g., "Inspection" states that the substrate finish would be inspected visually by lead contracting personnel or by a supervisor to ensure this type of defect is not present.

Detect $Pd_i$ (DET): The initial assessment for the ease that the process control will catch this failure mode before the process completion (e.g., "1"=indicates that the controls. In such a case, "visual inspection by a supervisor" would almost always detect the existence of a surface void and correct it before the primer is applied). The categories are: 1 for "Very High", 2 for "High", 3 for "Moderate", 4 for "Low", and 5 for "Very Low".

$RPN_i$: The initial Risk Priority Number, for the failure mode, is the product of the severity, occurrence and detection assessments ($RPN_i=S_i\times P_i\times Pd_i$) and can range from 1 to 125; RPN provides a value that represents the risk associated with the potential failure mode. The risks associated from a failure mode with a marginal severity and a medium likelihood of occurrence would be moderated if the failure could always be detected before the process is completed (e.g., 3×3×1="9", which represents an acceptable level of risk).

Risk Mitigation: What actions and/or changes can be made to the process to mitigation the risk from the potential failure mode (e.g. a blank space indicates no action is required since the assessed risk for a void in the substrate failure mode, is acceptable since RPN=9).

Action Results: Shows the mitigated risk ($RPN_f$) from the moderated severity, occurrence and detection assessments ($S_f$, $P_f$ and $Pd_f$), which result from the action or actions taken for risk mitigation.

FIG. 18 depicts the current-art initial process risk assessments for each identified potential failure mode, and are graded from highest to lowest. It is evident that most of the $RPN_i$ values are above the 'Mitigate Risk' threshold (lower dashed line), while two exceed the 'Unacceptable Risk' threshold (upper dashed line). The two risks deemed as unacceptable (RPN>50) are associated with failure modes W.2 and W.1; it should be noted that these are post-process failure modes (the structure has been turned over to the customer and in use):

Failure mode W.2 is leakage resulting from undetected defects in the waterproofing system that causes water to appear within the structure after the warranty period has passed (normally after one year, for the life of the structure); RPN=100.

Failure mode W.1 is leakage resulting from a latent undetected defect in the waterproofing system that causes water to appear within the structure during the warranty period (normally one year); RPN=60.

The key point here is that leaks from latent defects occurring after the structure has already been turned over to the customer using the current-art systems and processes will only be detected after water had entered the structure (even if water is observed inside a building, there is no guarantee the location of the water correlates with that of the waterproofing defect, and often water can run behind a compromised waterproofing system for many dozens of feet before entering the structure; this is also why the detectability is set to very low [=5]), and these leaks will have a good chance of damaging items within the structure. If a building contains critical items such as computers, laboratories, and paper documents/records, the potential for loss (and therefore the severity) is greatly elevated.

There are nine risks that must be mitigated (RPN 11 to 50), which are associated with failure modes J.1, H.1, E.1, D.1, D.2, D.3, F.1, F.2, and G.1—note that these are in-process failure modes (before the structure has been turned over to the customer):

Failure mode J.1 is leakage resulting from defects in the waterproofing system that were not identified during the verification inspection before backfill was applied; these defects soon cause leakage into the structure during the first heavy rains or snow melting events; this applies up to the point the structure is turned over to the customer (without these weather events, the defects may carry over into the warranty period, at which point they become W.1 post-process failures); RPN=45.

Failure mode H.1 is leakage resulting from a build-up of hydrostatic pressure on the waterproofing system because of clogged drainage channels from soil infiltration caused by punctured or ripped filter fabric; the pressure build-up may cause weak areas of the membrane to fail causing leakage into the structure (when a leakage failure occurs, the defect becomes an H.1 in-process failure); RPN=45.

Failure mode E.1 is leakage resulting from detailing errors on the membrane joints, edges and overlaps, which remain undetected during the inspection phase before the drainage board is applied; RPN=27.

Failure mode D.1 is leakage resulting from a defectively-installed membrane, causing wrinkles and fish-mouths, which remain undetected during the inspection phase before the drainage board is applied; RPN=18.

Failure mode D.2 is leakage resulting from a defectively-installed membrane, caused by material contamination of the membrane adhesive (e.g., windblown debris or other), which remains undetected during the inspection phase before the drainage board is applied; RPN=18.

Failure mode D.3 is leakage resulting from a defectively-installed membrane, caused by large-area but shallow unevenness in the substrate, which remains undetected during the inspection phase before the drainage board is applied; RPN=18.

Failure mode F.1 is leakage resulting from a defectively-installed drain board (water is not prevented from building up at the membrane), caused by chemical contamination (e.g., oils or greases) of the membrane surface where the drainage board adhesive is applied, which remains undetected during the inspection phase before the drainage board is applied; RPN=18.

Failure mode F.2 is leakage resulting from a defectively-installed drain board (water is not prevented from building up at the membrane), caused by material contamination of the drainage board adhesive (e.g., windblown debris or other contaminants), which remains undetected during the inspection phase before the drainage board is applied; RPN=18.

Failure mode G.1 is leakage resulting from a defectively-installed drain board (water is not prevented from building up at the membrane), caused by poor adhesion to the drainage board adhesive caused by allowing the adhesive to partially cure (e.g., the contractor waited too long between adhesive application and drainage board installation, which remains undetected during the inspection phase before the drainage board is applied); RPN=18.

There are four risks that do not need mitigation (RPN<10) and are associated with failure modes B.1, B.2, C.1, and D.4.

Failure mode B.1 is leakage resulting from a small-area void in the substrate, which causes the membrane to not adhere properly to this point, and remains undetected during the inspection phase before the primer and membrane are applied; RPN=9.

Failure mode B.2 is leakage resulting from a small-area elevation in the substrate, which causes the membrane to not adhere properly around this point, and remains undetected during the inspection phase before the primer and membrane are applied; RPN=9.

Failure mode C.1 is leakage resulting from a defectively-applied primer, resulting in poor membrane adhesion caused by chemical contamination (e.g., oils or greases) of the substrate where the primer is applied, which remains undetected during the inspection phase before the membrane is applied; RPN=9.

Failure mode D.4 is leakage resulting from a materially-compromised membrane, resulting from excessive exposure of the membrane to the sun's ultraviolet (UV) rays (e.g., drainage board was not installed after membrane application for a period exceeding the manufacturer's maximum specified time), which remains undetected during the inspection phase before the membrane is applied; RPN=6.

This current-art process contains high-levels of risk that needs mitigation to reduce the probability of a leakage failure in this below-grade waterproofing system during installation.

TABLE 3

Current-Art Process Summary Metrics

| Process Summary Metric | Value |
| --- | --- |
| Sum of the RPN for the 15 identified potential failure modes | 418 |
| Mean of the RPN for the 15 identified potential failure modes | 27.9 |
| Median of the RPN for the 15 identified potential failure modes | 18 |

Process-Risk Mitigation

Most of the risks associated with the identified potential failure modes can be grouped into two primary categories and one minor category:

1. Major: There are many manual process operations that are subject to variation from field installation by contractors.

2. Major: There is no way to properly verify the installation through inspection, especially after the system has been assembled and any missed defects have been covered.

3. Minor: Filter-fabric damage during backfill may result in a latent waterproofing defect.

The process steps in FIG. 16A that can be mitigated by addressing the above concerns are D, E, F, G, H, I, and L.

Improved Installation Process Overview

Referring to FIGS. 17A-17B, the improved waterproofing system has been designed to mitigate the risks associated with the potential failure modes identified in the FMEA:

1. The process of attaching the drainage board 7 to the membrane 1 has been changed from a manual operation that takes place in the field to a controlled operation that takes place in a factory (consolidation of Process Operations D, F, and G and mitigation of the associated risks). It should be noted that Operation E becomes a sub-process in the field using factory-produced field joints and corners (see FIGS. 4A-4C, 5A-5B, 6A-6B, and 7A-7B) to minimize the occurrence of associated defects.

2. An intrinsic electronic leak-detection capability, suitable for below-grade applications, has been added to the waterproofing membrane 1. Additionally, a membrane-adhesion verification capability is also possible with this feature (mitigation of risks associated with Process Operation H, and mitigation of the risks associated with post-process inspection during the warranty and post-warranty periods [Operations I, L, and M]).

3. An anti-abrasion layer, placed over the filter fabric as a factory operation, addresses the damage potential to the filter-fabric during backfill (mitigates risk associated with Process Operation J).

4. The FMEA-improved waterproofing system installation process is shown in FIG. 17A and is described in Table 4. The process steps are illustrated in FIG. 17B (corner fragment show, drawing not to scale). The existing vertical foundation wall installation case applies for this example (i.e., not blindside or under-slab installations).

The process steps in FIG. 17A that can be mitigated by addressing the above concerns are D, E, F, G, H, I, L, and M. The process modifications are identified as "Action Results" in the detailed FMEA worksheet shown in the Appendix A. FIG. 17A process flowchart shows how the installation process flow has been modified (the original process operations B through J are retained to indicate where these operations reside in the updated process).

TABLE 4

Improved Process Step Descriptions

| ID | Process Step | Description |
| --- | --- | --- |
| A | Start Installation | The Architectural Specification (unique for each construction project) defines the waterproofing materials and general installation requirements<br>Contractors for installation are chosen based on the contractor's certifications and experience |
| B | Prepare Substrate | Level installation surfaces, remove rough spots that could damage the membrane |
| C | Prime Substrate | Apply primer coating (surface is enhanced for optimal membrane adhesion)<br>Conductive primer [4] may be used to allow capacitive verification testing to be performed |
| D, F, G, H | Install Waterproofing Panel | Remove membrane release liner and apply integrated waterproofing panel (membrane, leak-detection, drainage board, anti-abrasion layer) to the substrate<br>D: Detail panel A/R (Sub-process): edges, joints and seams are filled using sealant |
| I | Verify Installation | Verification (prior to backfilling):<br>The manufacturer's representative verifies that the recommended drainage board installation process has been followed by the contractor (warranty certification requirement) and the system installation meets quality requirements (good drainage board adhesion, proper overlaps, etc.) using visual methods and audit of construction records<br>Verify panel adhesion to substrate using capacitance test<br>Verify leak-proof integrity using intrinsic electrical-leak test (vertical installations can be sprayed with water during this test phase)<br>Data is entered into topographical database |
| J | Bury Installation | Earthen backfill is used to bury the installation below ground |
| K | Installation Complete | Post-backfill check:<br>Verify leak-proof integrity using intrinsic electrical-leak test<br>Data is entered into topographical database as the baseline for trend analysis |
| L, M | On-Site/Remote Validation for Warranty | Warranty period:<br>Continuously monitor the installation using intrinsic leak-detection<br>Data is entered into topographical database and tracked<br>Statistical Process Control is used to identify out-of-family trends<br>Any anomalies must be proactively investigated/repaired<br>Repairs inside the warranty period require root-cause investigation and corrective action |

FMEA Final Risk Assessment

FIG. 19 depicts the improved process risk assessments for each identified potential failure mode, and are graded from highest to lowest. As opposed to the prior-art process risk assessments shown in FIG. 18, all $RPN_f$ values now fall below the "Mitigate Risk" threshold (lower dashed line). The highest relative risk shown in FIG. 19 remains failure mode W.2, but now the potential risk has been reduced to one-tenth of its original value for the prior-art process risk assessment (as shown in FIG. 18); that is, the RPN went from 100 to 10. Failure mode W.2 corresponds to leakage resulting from defects that arise in the waterproofing system that may cause water to appear within the structure after the warranty period has passed (typically, in the industry, this is after one year, for the life of the structure). Three risks, B.1, B.2 and C.1, are associated with process operations that occur prior to installation of the integrated waterproofing panels. These remain unchanged from the risk assessment for the prior-art process shown in FIG. 18. Note that severity is retained at level 3 since water infiltration below the membrane will not be detected by the intrinsic system until water has progressed to a seam between panels, and then wicks up to make contact with the conducting element within the membrane.

The next two highest relative $RPN_f$ values shown in FIG. 19 come from two membrane-adhesion related failure modes, D.2 and D.3, the in-process detection is degraded because the bare membrane will no longer be visible during the inspection, but this disadvantage is offset by reduction in the severity due to the added integrated verification capabilities. Failure mode D.2 is leakage resulting from a defectively-installed membrane, caused by material contamination of the membrane adhesive (e.g., windblown debris or other contaminants), which remains undetected during the inspection phase before the backfill operation. Using the improved fabrication and installation process, the RPN of D.2 of the prior-art process is improved by cutting the risk in half; that is, RPN now equals 9. Failure mode D.3 is leakage resulting from a defectively-installed membrane, caused by large-area but shallow unevenness in the substrate, which remains undetected during the inspection phase before the drainage board is applied. Once again, using the improved fabrication and installation process, the RPN of D.3 of the prior-art process is improved by cutting the risk in half; that is, RPN now equals 9.

The next two highest relative $RPN_f$ values come from a membrane-defect associated failure modes D.1, and a sub-process failure mode E.1, which are not fully within the control of the factory process (in embodiments, the improved configuration attempts to mitigate this with factory-produced accessories for making better-controlled joints and corners in the field). Failure mode D.1 is leakage resulting from a defectively-installed membrane, causing wrinkles and fish-mouths, which remain undetected during the inspection phase before the drainage board is applied. Using the improved fabrication and installation process, the RPN of D.1 of the prior-art process is improved by cutting the risk down to a third of the prior-art value; that is, RPN now equals 6. Failure mode E.1 is leakage resulting from detailing errors on the membrane joints, edges and overlaps, which remain undetected during the inspection phase, and before the backfill operation. Using the improved fabrication and installation process, the RPN of E.1 of the prior-art process is improved by cutting the risk down by nearly 80% of the prior-art value; that is, RPN now equals 6 as opposed to 27.

The next highest relative $RPN_f$ value comes from the backfill associated failure mode J.1 (the improved configuration mitigates this with the anti-abrasion layer over the filter fabric).

Failure mode J.1 is leakage resulting from a build-up of hydrostatic pressure on the waterproofing system because of clogged drainage channels from soil infiltration caused by punctured or ripped filter fabric; the pressure build-up may cause weak areas of the membrane to fail causing leakage into the structure (when a leakage failure occurs, the defect becomes an H.1 in-process failure). Using the improved fabrication and installation process, the RPN of J.1 of the prior-art process is improved by cutting the risk down by over 90% of the prior-art value; that is, RPN now equals 4 as opposed to 45.

The next highest relative $RPN_f$ value comes from the post-process warranty period associated failure mode W.1, which is leakage resulting from a latent undetected defect in the waterproofing system, which causes water to appear within the structure during the warranty period (normally 1 year). Using the improved fabrication and installation process, the RPN of W.1 of the prior-art process is improved by cutting the risk down by a factor of 20 of the prior-art value; that is, RPN now equals 3 as opposed to 60.

Failure modes D.4, F.1, F.2, and G.1 are associated with process operations, which will occur in the factory during assembly of the improved integrated waterproofing panels 15 (membrane 1 bonded to drainage panels 7). Because of the reduction in variability from the replacement of the manual field process steps with factory-controlled operations, the severity, occurrence, and detectability category levels all become are reduced to a value of 1; that is, RPN=1, which, with the exception of D.4, represents a 50% decrease in risk from the prior-art process.

Failure mode H.1 associated with verification. Because the improved integrated waterproofing panels 15 will contain integrated verification and intrinsic leak-detection capabilities, the severity, occurrence, and detectability risk-category levels all have a value of 1; that is, RPN=1, which is an 80% reduction in risk from the prior-art process.

Overall, the improved process is able to mitigate the risks associated with the probability of a leakage failure in the original current-art below-grade waterproofing system both during the installation process and during the post-process warranty-verification period after the structure has been delivered to the customer. Table 5 below provides a summary of the improvement in the risk-assessment metrics between typical current-art systems and processes and the present improved systems and processes.

TABLE 5

Comparison of Relative Risk Assessment for the 15 Identified Potential Failure Modes Between Current-Art Processes and the Improved Process

| Process Summary Metric | Current-Art Process Value | Improved Process Value |
| --- | --- | --- |
| Sum of Failure-Mode RPNs | 418 | 79 |
| Mean of Failure-Mode RPNs | 27.87 | 5.27 |
| Median of Failure-Mode RPNs | 18 | 6 |

The summary metrics in Table 5 indicate a significant reduction in the relative risk when the improved waterproofing-panel system 15 and installation processes is compared to current-art below-grade waterproofing systems that are available in the market. A process FMEA performed on a typical current-art below-grade waterproofing system installation has revealed an intolerably high level of risk associated with the aforementioned 15 identified potential failure modes. The risk entails the infiltration of ground water into the customer's building through a defective waterproofing system that results in a moisture-degraded environment within the structure, and also results in damage to critical items residing within the building from moisture and ground water. The process FMEA was used to show how the present improved waterproofing system and installation process can be employed to mitigate this high level of risk to an acceptable level. Finally, it follows that the present improved waterproofing system also reduces total costs (to the customers, to the customer's employees/clients, to the general contractor and to the subcontractors); that is:

Costs associated with direct labor costs are reduced because the installation process has been simplified, because the RPN for the major process operations conducted on the construction site will be significantly reduced;

The construction site logistical footprint for the waterproofing system will be reduced due to less items in the bill-of-material and the simpler process;

The incidences of rework and construction delays will be reduced due to a more fail-safe installation process;

The costs associated with finding latent defects in the waterproofing system—only by evidence of water in the building after the customer begins to use the building—will be eliminated by the integrated verification and intrinsic leak-detection capabilities;

The warranty costs will be reduced;

The loss due to water-damage to critical items within the structure will be reduced (and potentially eliminated altogether); and The losses due to illness from toxic mold contamination will be reduced (and potentially eliminated altogether).

V. Alternative Embodiments and Other Variations

The various embodiments and variations thereof described herein, including the descriptions in any appended claims and/or illustrated in the accompanying Figures, are merely exemplary and are not meant to limit the scope of the inventive disclosure. It should be appreciated that numerous variations of the invention have been contemplated as would be obvious to one of ordinary skill in the art with the benefit of this disclosure.

Hence, those ordinarily skilled in the art will have no difficulty devising myriad obvious variations and improvements to the invention, all of which are intended to be encompassed within the scope of the Description, Figures, and Claims herein.

What is claimed is:

1. A waterproofing-panel assembly, comprising:
   a composite waterproofing membrane, the composite waterproofing membrane having:
      a rubberized asphalt layer, the rubberized asphalt layer has a proximal surface side and a distal surface side, wherein the proximal side surface is positioned, relative to the distal surface side, closest to a building's surface, a pressure sensitive rubberized asphalt adhesive coating under, relative to the proximal surface side being designated the composite waterproofing membrane's base, the proximal surface side,
a film backing positioned over the distal surface side, and
an electrically-conductive membrane layer with metal strips is between the rubberized asphalt layer and the film backing, wherein all of said metal strips are in electrical communication to represent a single electrical node;
a drain board core over the film backing;
a filter fabric over the drain board; and
an anti-abrasion layer over the filter fabric.

2. The waterproofing-panel assembly of claim 1, further comprising:
an electrical conduit that couples the electrically-conductive membrane layer or metal strips to an electrical-condition-measurement device, the electrical-condition-measurement device capable of measuring the capacitance between said electrically-conductive membrane and a substrate configuration to provide:
intrinsic leak-detection capability by measuring dielectric permittivity of the layers of said waterproofing-panel assembly,
monitoring a functional topography of the composite waterproofing membrane,
an inference to confirm whether the composite waterproofing membrane contacts the building's surface, and
combinations thereof.

3. The waterproofing-panel assembly of claim 1, further comprising:
a conductive primer positioned between the proximal surface side and the building's surface; and
an electrical conduit that couples the conductive primer to an electrical-conditions-measurement device, the electrical-condition-measurement device capable of measuring the capacitance between said electrically-conductive membrane and an electrically primed substrate to provide:
intrinsic leak-detection capability by measuring dielectric permittivity of the layers of said waterproofing-panel assembly,
monitoring a functional topography of the composite waterproofing membrane,
an inference to confirm whether the composite waterproofing membrane contacts the building's surface, and
combinations thereof.

4. The waterproofing-panel assembly of claim 2, wherein the electrical-condition-measurement device is an LCR meter.

5. The waterproofing-panel assembly of claim 3, wherein the electrical-condition-measurement device is an LCR meter.

6. The waterproofing-panel assembly of claim 1, wherein the waterproofing-panel assembly appends to the building's surface without penetrating the composite waterproofing membrane.

7. The waterproofing-panel assembly of claim 6, wherein:
the waterproofing-panel assembly contacts soil, sand, rocks, gravel, clay, water, or combinations thereof; and
the building's surface is selected from the group consisting of a basement floor, a slab, a subterranean basement vertical wall, a partially subterranean basement vertical wall, a basement vertical wall, and a slab's side surface.

8. The waterproofing-panel assembly of claim 1, wherein said anti-abrasion layer is perforated and made from a material selected from the group comprising high-impact polystyrene and any functionally equivalent fungus-resistant and rot-resistant material.

9. The waterproofing-panel assembly of claim 6, wherein the waterproofing assembly attaches through strings or tie-wraps positioned in a scaffolding cross member's opening.

10. The waterproofing-panel assembly of claim 8, wherein said anti-abrasion layer includes a bend-relief feature in the form of a plurality of traverse creases that provide said waterproofing panel with longitudinal flexibility to facilitate storage and shipment in rolls.

11. The waterproofing-panel assembly of claim 1, further comprising a fluid-applied membrane that is disposed on a building's surface and adhesively coupled to said waterproofing-panel assembly.

12. The waterproofing-panel assembly of claim 11, further comprising an electrically-conductive membrane layer fixedly bonded to the posterior side of said waterproofing-panel assembly, wherein:
said electrically-conductive membrane layer is comprised of HDPE cross-laminated film backing with an electrically-conductive metal element, and is bonded to said posterior side of said waterproofing-panel assembly.

13. The waterproofing-panel assembly of claim 12, wherein said electrically-conductive membrane layer does not extend all the way to the edge of said drain board and is recessed back from said drain-board edge by approximately 0.125 inches.

14. The waterproofing-panel assembly of claim 12, wherein said electrically-conductive metal element is of a type selected from the group consisting of metal film, metal foil, and metal-wire mesh.

15. The waterproofing-panel assembly of claim 12, wherein said electrically-conductive metal element is a metallic film that is 2-3 mills thick.

16. The waterproofing-panel assembly of claim 12, wherein said electrically-conductive metal element is a 40 AWG metal-wire mesh that is approximately 25% filled.

17. The waterproofing-panel assembly of claim 12, wherein said HDPE cross-laminated film backing is bonded to said electrically-conductive metal element using an industrial-grade low-VOC adhesive.

18. The waterproofing-panel assembly of claim 12, wherein said bonding to said waterproofing-panel assembly is accomplished by using an industrial-grade low-VOC adhesive.

19. The waterproofing-panel assembly of claim 12, wherein said HDPE cross-laminated film backing is approximately 5 mils thick.

20. A plurality of waterproofing-panel assemblies in a controlled factory setting, for later installation on a building-construction project, wherein each waterproofing-panel assembly comprises:
a composite waterproofing membrane, the composite waterproofing membrane having:
a rubberized asphalt layer, the rubberized asphalt layer has a proximal surface side and a distal surface side, wherein the proximal side surface is positioned, relative to the distal surface side, closest to a building's surface,
a pressure sensitive rubberized asphalt adhesive coating under, relative to the proximal surface side being designated the composite waterproofing membrane's base, the proximal surface side, a film backing positioned over the distal surface side, and an electrically-conductive membrane layer with metal strips is between the rubberized asphalt layer and the film backing, wherein all of said metal strips are in electrical communication to represent a single electrical node;

a drain board core over the film backing;
a filter fabric over the drain board; and
an anti-abrasion layer over the filter fabric; and
whereby the sum of Risk-Priority Numbers (RPNs) for said plurality of waterproofing panels, once installed, is less than or equal to 79, said RPNs covering the installation and post-installation task areas of substrate preparation, primer application, membrane installation, membrane detailing, adhesive applications, drain-panel installation, in-field verification, warranty-period inspections, and post-warranty-period inspections.

* * * * *

UNITED STATES PATENT AND TRADEMARK OFFICE
CERTIFICATE OF CORRECTION

| | | |
|---|---|---|
| PATENT NO. | : 10,344,470 B2 | |
| APPLICATION NO. | : 15/709980 | |
| DATED | : July 9, 2019 | |
| INVENTOR(S) | : Golding, Jr. et al. | |

It is certified that error appears in the above-identified patent and that said Letters Patent is hereby corrected as shown below:

Please delete Pat. No. 10,344,470 B2 in its entirety and insert Pat. No. 10,344,470 B2 in its entirety as shown on the attached pages.

Signed and Sealed this
Eleventh Day of August, 2020

Andrei Iancu
*Director of the United States Patent and Trademark Office*

US 10,344,470 B2
Page 2

Related U.S. Application Data

(60) Provisional application No. 62/148,312, filed on Apr. 16, 2015.

(51) Int. Cl.

| | |
|---|---|
| *G01M 3/16* | (2006.01) |
| *E02D 31/02* | (2006.01) |
| *B32B 5/02* | (2006.01) |
| *B32B 7/12* | (2006.01) |
| *E04C 2/52* | (2006.01) |
| *G01N 27/22* | (2006.01) |
| *G01N 27/24* | (2006.01) |
| *B32B 5/26* | (2006.01) |
| *B32B 7/06* | (2019.01) |
| *B32B 7/08* | (2019.01) |
| *B32B 7/14* | (2006.01) |
| *B32B 11/06* | (2006.01) |
| *B32B 11/08* | (2006.01) |
| *B32B 11/10* | (2006.01) |
| *B32B 15/02* | (2006.01) |
| *B32B 15/085* | (2006.01) |
| *B32B 15/18* | (2006.01) |
| *B32B 15/20* | (2006.01) |
| *B32B 27/12* | (2006.01) |
| *B32B 27/30* | (2006.01) |
| *B32B 27/32* | (2006.01) |
| *B32B 3/02* | (2006.01) |
| *B32B 3/18* | (2006.01) |
| *B32B 3/26* | (2006.01) |
| *B32B 3/30* | (2006.01) |
| *G01N 27/04* | (2006.01) |
| *G01N 27/20* | (2006.01) |

(52) U.S. Cl.
CPC .............. *B32B 11/10* (2013.01); *B32B 15/02* (2013.01); *B32B 15/085* (2013.01); *B32B 15/18* (2013.01); *B32B 15/20* (2013.01); *B32B 27/12* (2013.01); *B32B 27/302* (2013.01); *B32B 27/32* (2013.01); *E02D 31/025* (2013.01); *E04C 2/528* (2013.01); *G01M 3/045* (2013.01); *G01M 3/16* (2013.01); *G01N 27/223* (2013.01); *G01N 27/24* (2013.01); *B32B 2260/02* (2013.01); *B32B 2260/046* (2013.01); *B32B 2262/0253* (2013.01); *B32B 2307/202* (2013.01); *B32B 2307/50* (2013.01); *B32B 2307/554* (2013.01); *B32B 2307/7145* (2013.01); *B32B 2307/73* (2013.01); *B32B 2307/732* (2013.01); *B32B 2307/748* (2013.01); *B32B 2395/00* (2013.01); *B32B 2419/00* (2013.01); *B32B 2607/00* (2013.01); *E02D 2600/10* (2013.01); *G01N 27/048* (2013.01); *G01N 27/20* (2013.01)

(56) References Cited

U.S. PATENT DOCUMENTS

| | | | |
|---|---|---|---|
| 3,654,765 | A | 4/1972 | Healy et al. |
| 3,888,087 | A | 6/1975 | Bergland |
| 4,404,516 | A | 9/1983 | Johnson |
| 4,467,015 | A | 8/1984 | Clem |
| 4,490,072 | A | 12/1984 | Glasser |
| 4,574,541 | A | 3/1986 | Raidt et al. |
| 4,704,048 | A | 11/1987 | Ahlgrimm |
| 4,720,669 | A | 1/1988 | Owen |
| 4,725,785 | A | 2/1988 | Converse et al. |
| 4,730,953 | A | 3/1988 | Tarko |
| 4,740,757 | A | 4/1988 | Converse et al. |
| 4,751,467 | A | 6/1988 | Cooper |
| 4,840,515 | A | 6/1989 | Freese |
| 4,897,313 | A | 1/1990 | Wiercinski |
| 4,943,185 | A | 7/1990 | McGuckin et al. |
| 5,081,422 | A | 1/1992 | Shih |
| 5,184,083 | A | 2/1993 | Groover |
| 5,263,792 | A | 11/1993 | Davis et al. |
| 5,288,168 | A | 2/1994 | Spencer |
| 5,463,377 | A | 10/1995 | Kronberg |
| 5,540,085 | A | 7/1996 | Sakata et al. |
| 5,763,036 | A | 6/1998 | Terry et al. |
| 5,850,144 | A | 12/1998 | Howells et al. |
| 6,331,778 | B1 | 12/2001 | Daily et al. |
| 7,292,155 | B2 | 11/2007 | Vokey et al. |
| 7,488,523 | B1 | 2/2009 | Muncaster et al. |
| 7,686,903 | B2 | 3/2010 | Muncaster et al. |
| 7,872,479 | B2 | 1/2011 | Lorenz et al. |
| 8,039,081 | B2 | 10/2011 | Ianniello et al. |
| 8,291,668 | B2 * | 10/2012 | Iske |
| 8,319,508 | B2 | 11/2012 | Vokey |
| 8,566,051 | B2 | 10/2013 | Gunness |
| 9,157,828 | B2 | 10/2015 | Jaman et al. |
| 9,244,030 | B2 | 1/2016 | Vokey et al. |
| 9,341,540 | B2 * | 5/2016 | Gunness |
| 2009/0044595 | A1 | 2/2009 | Vokey |
| 2010/0141281 | A1 * | 6/2010 | Johnsen |
| 2012/0074967 | A1 | 3/2012 | Vokey et al. |
| 2014/0049247 | A1 | 2/2014 | Gunness |
| 2014/0361796 | A1 | 12/2014 | Vokey et al. |

OTHER PUBLICATIONS

Caplinq's Technical Data Sheet for LINQSTAT XVCF-Series, published Jul. 2014; four pages.
National Instruments' data sheet for 6-½-Digit Digital Multimeter, 1.8 MS/s Isolated Digitizer, and LCR Meter, published in 2007; five pages.
The Concrete Society—electrical conductivity webpage; published prior to Apr. 15, 2015; one page.
Military Handbook: Grounding, Bonding, and Shielding for Electronic Equipments and Facilities vols. 1 and 2 of Two Volumes, basic theory, Dec. 1987; 812 pages.
Grace Waterproofing System's data sheet for Bituthene 6000 EIM, published 2014; two pages.
Melexis Microelectroni Integrated Systems data sheet for MLX90129, published 2012; 60 pages.

* cited by examiner

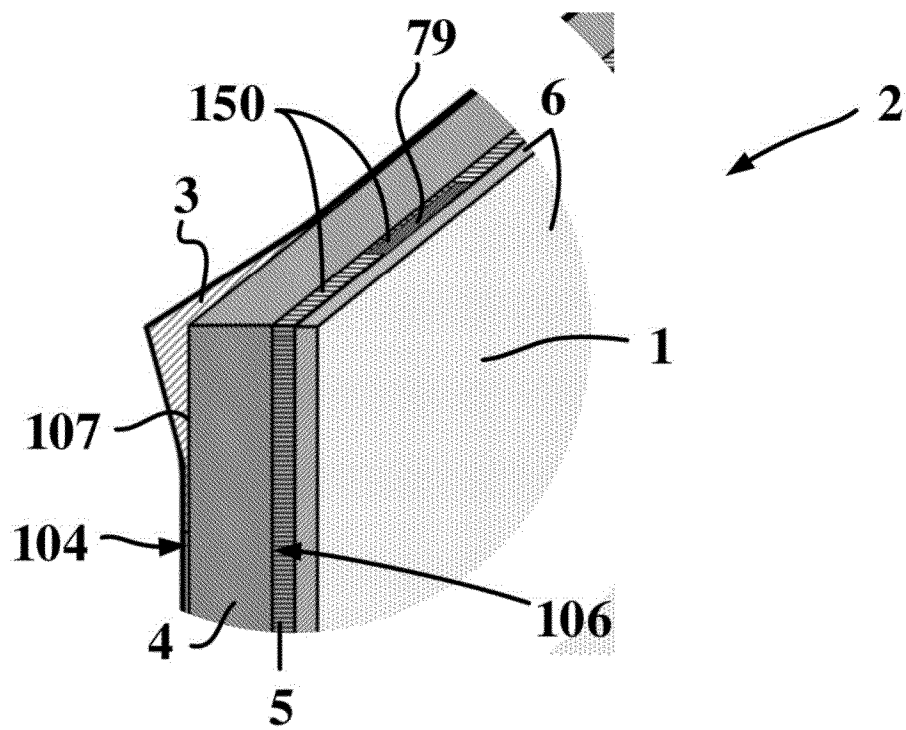
FIG. 1B
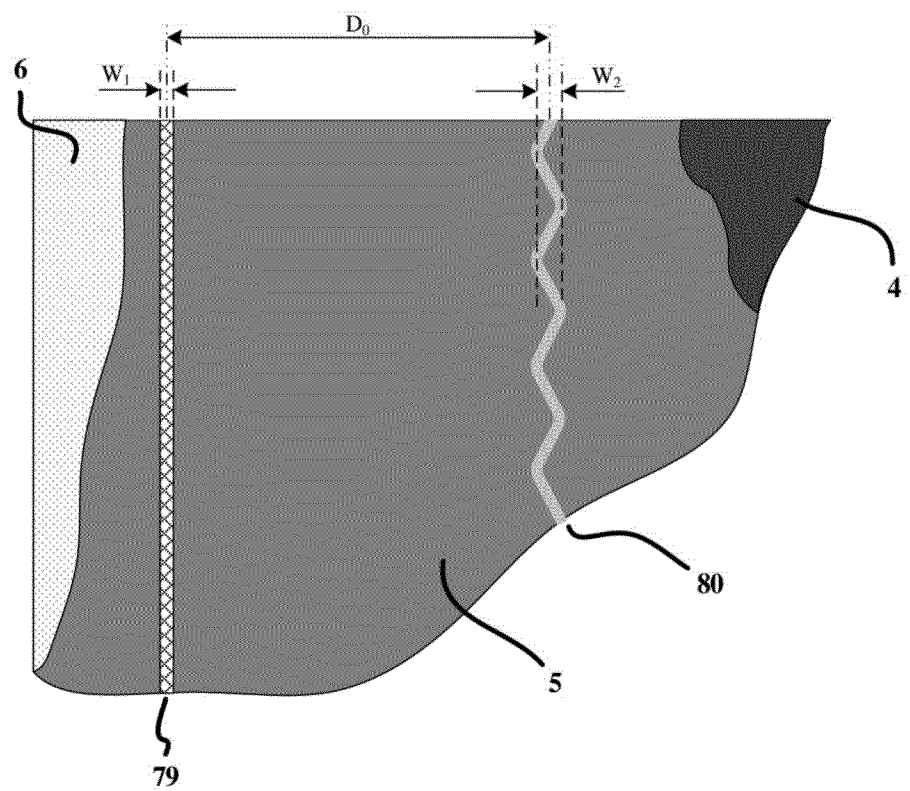
FIG. 1C

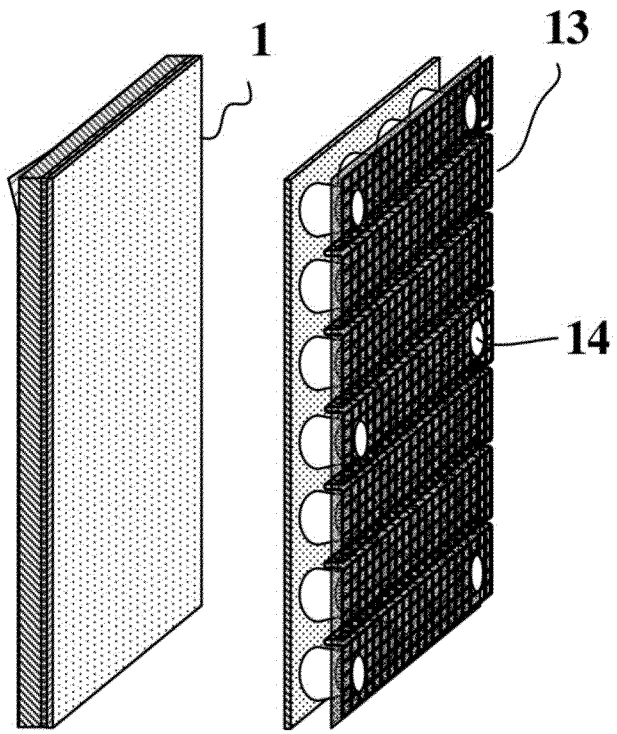
FIG. 2
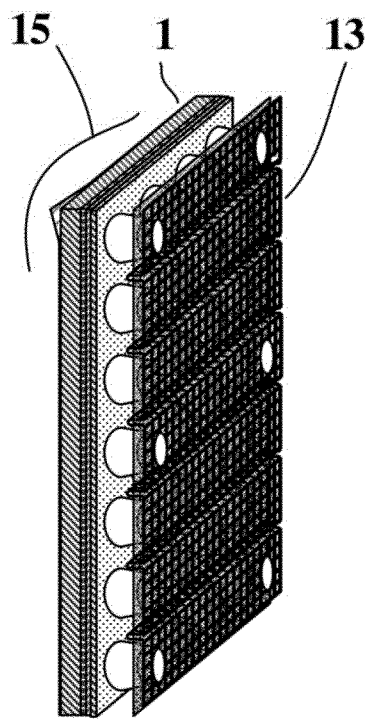
FIG. 3

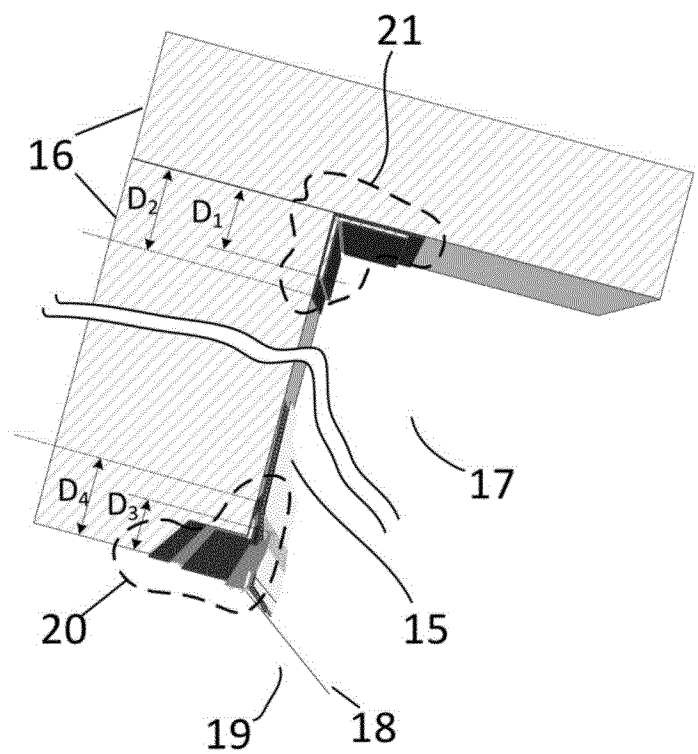
FIG. 4A
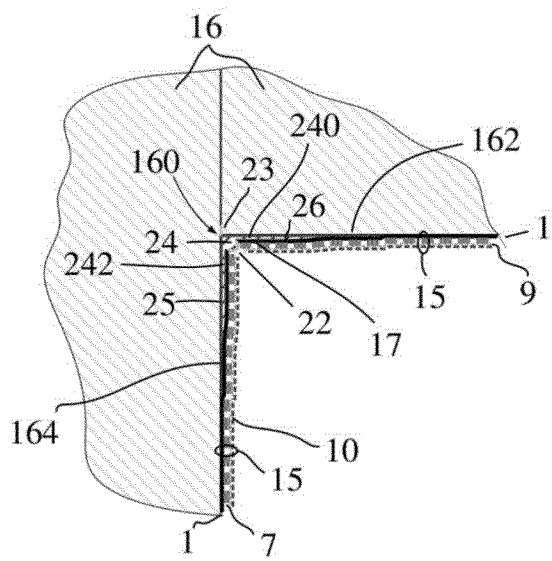
FIG. 4B
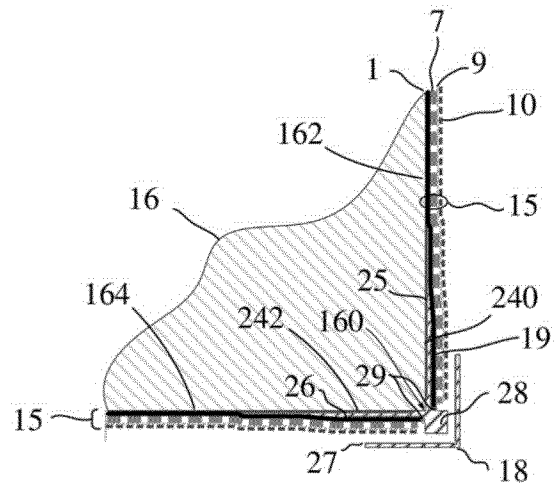
FIG. 4C

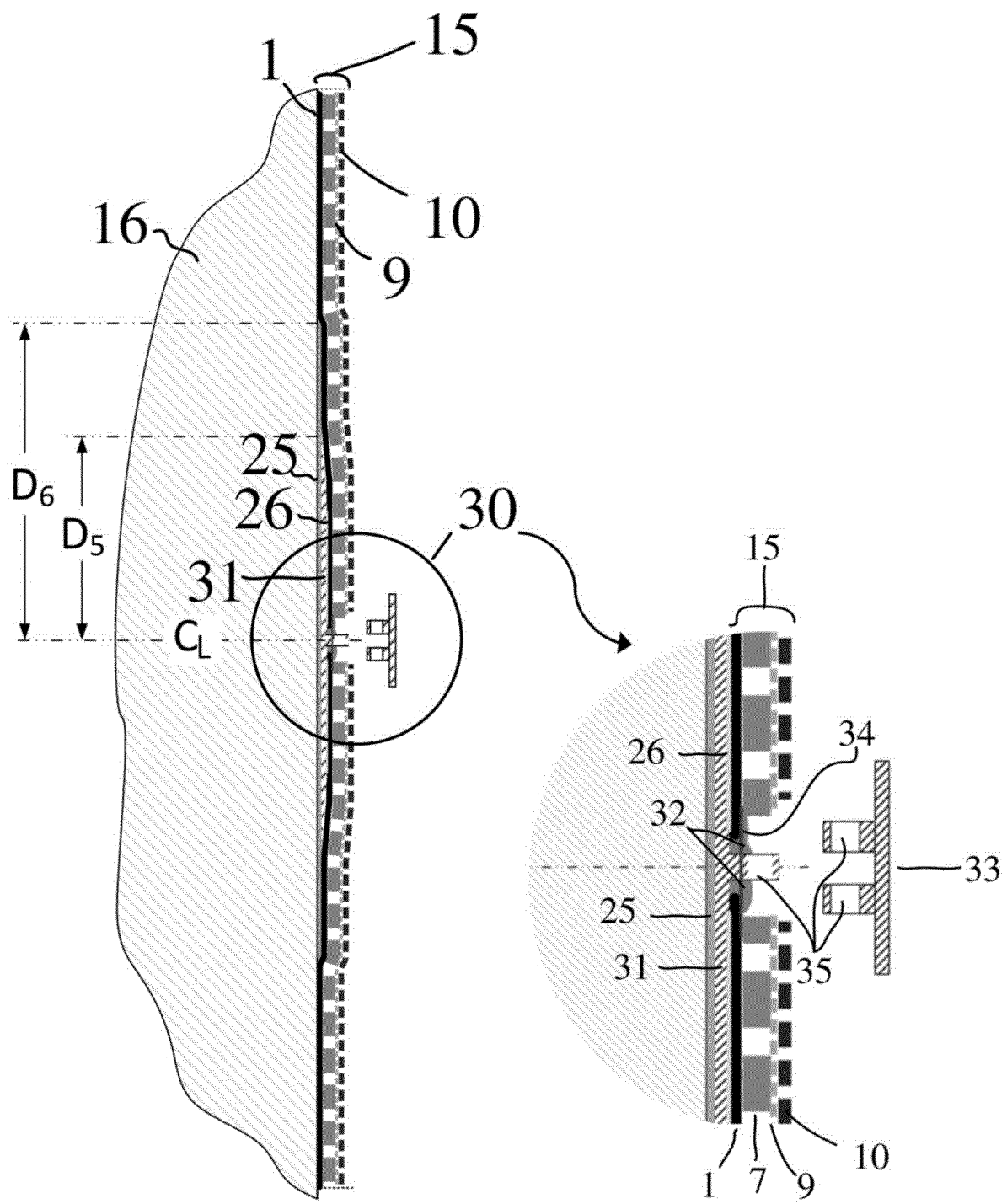
FIG. 5A  FIG. 5B

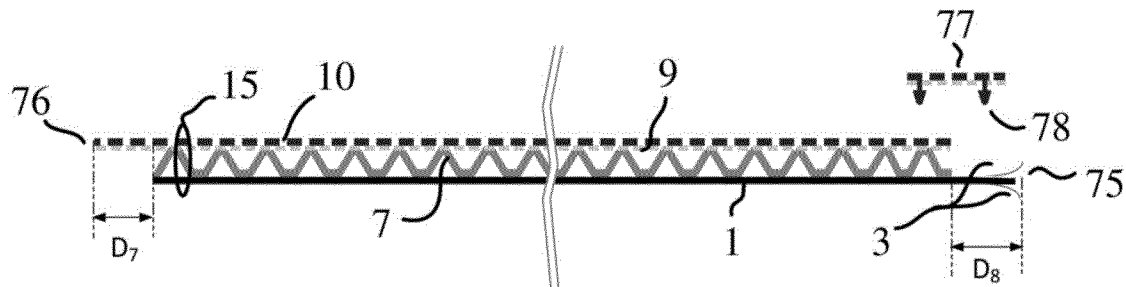
FIG. 6A
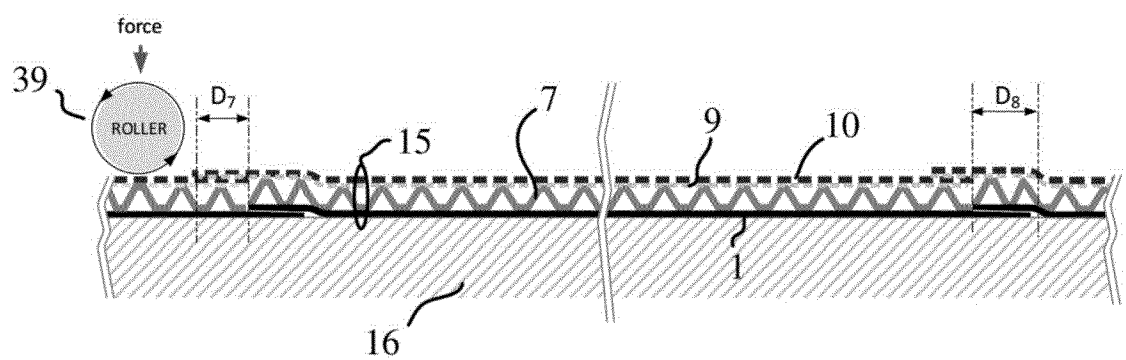
FIG. 6B

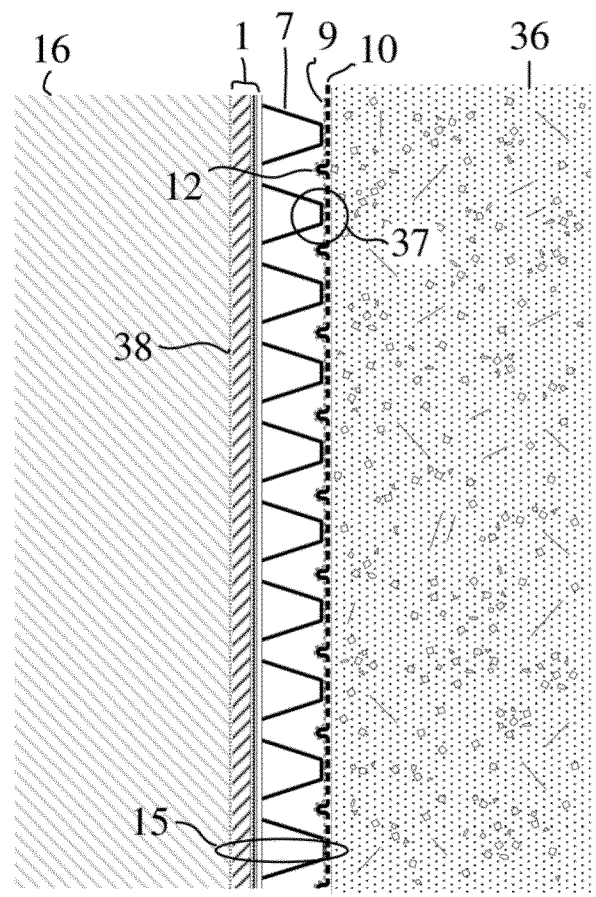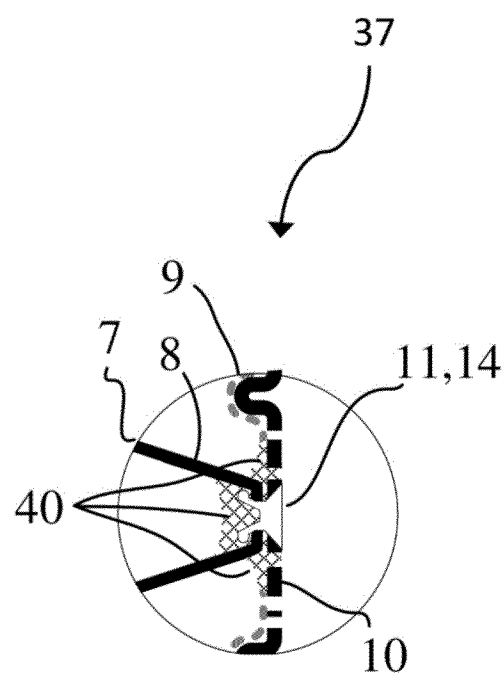
FIG. 7A
FIG. 7B

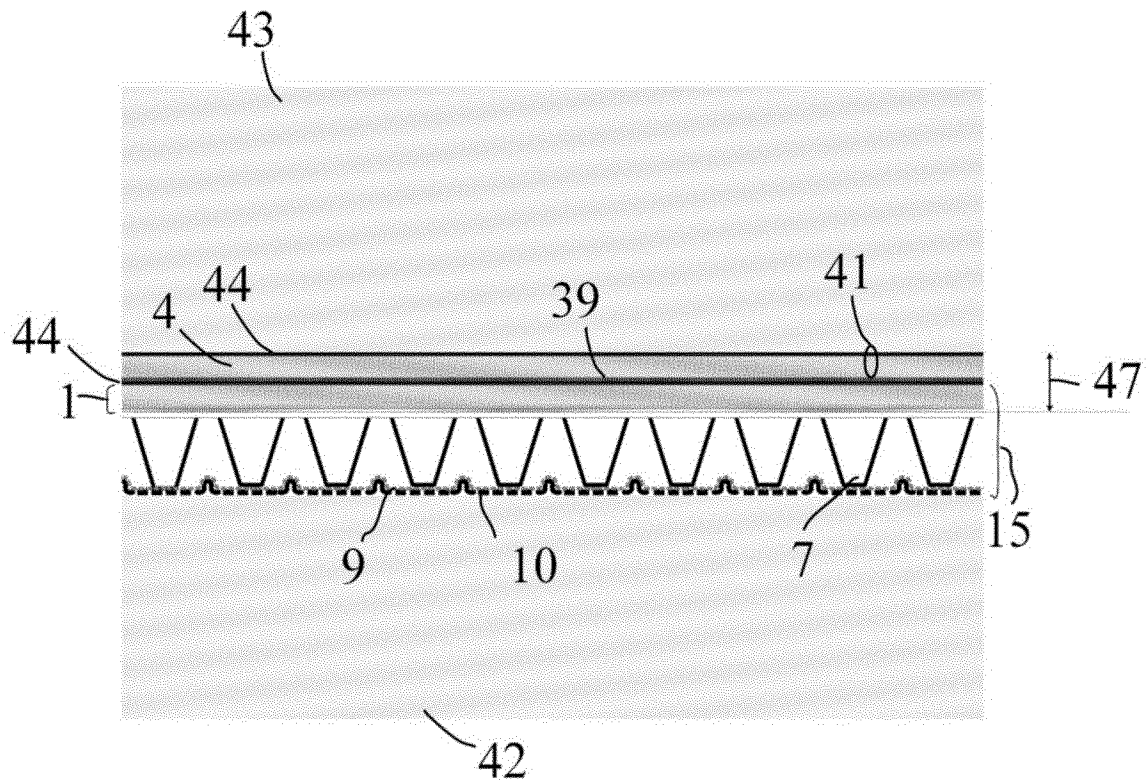
FIG. 8B
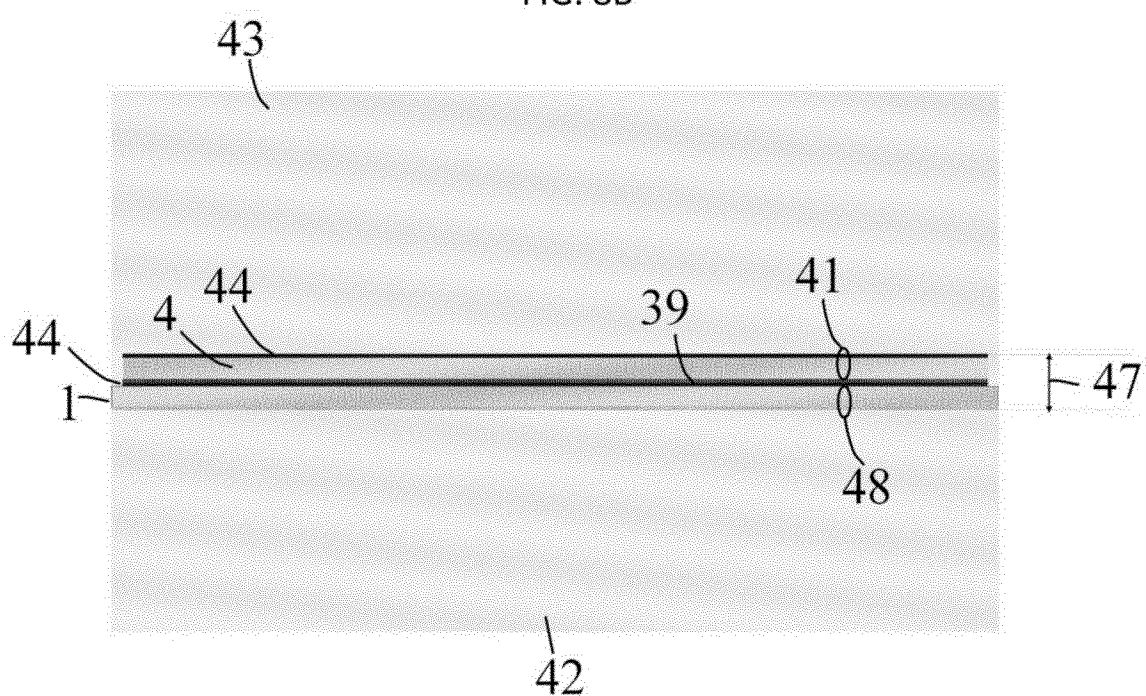
FIG. 8C

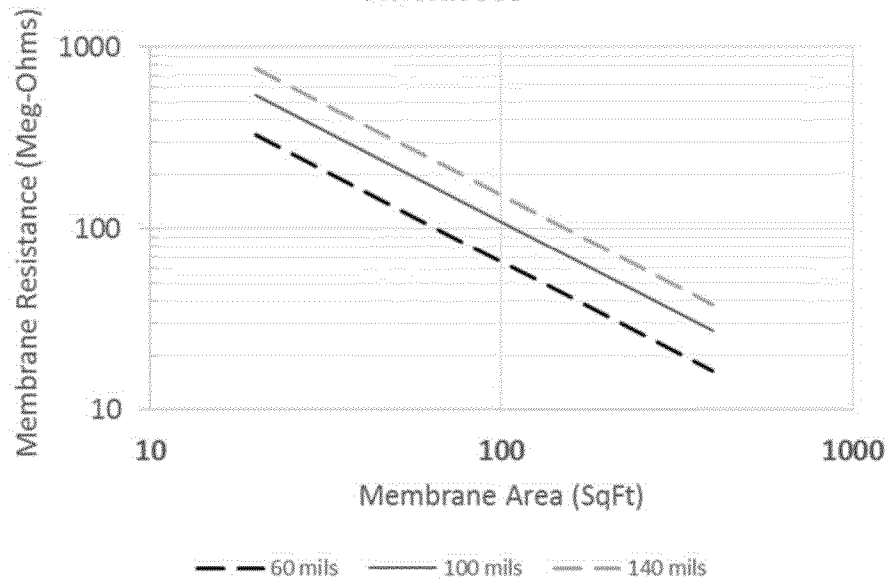
FIG. 8D
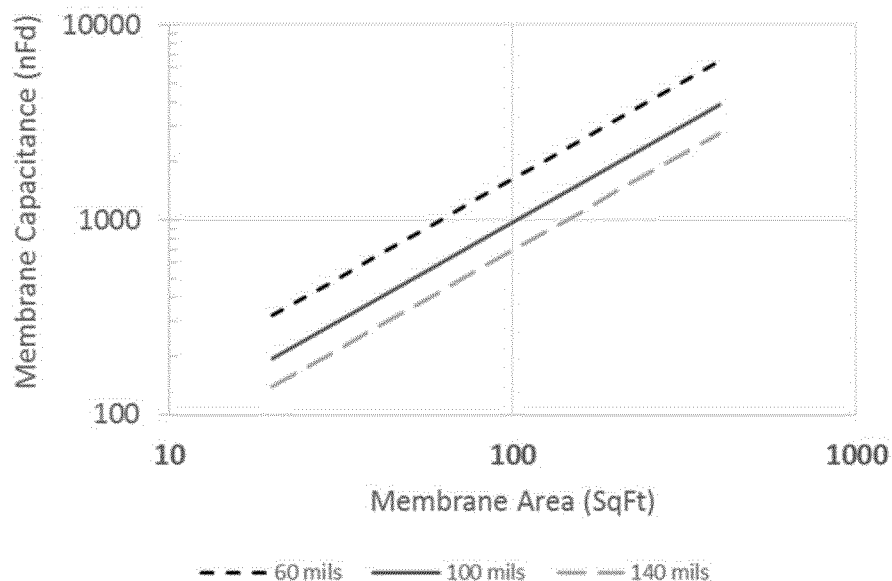
FIG. 8E

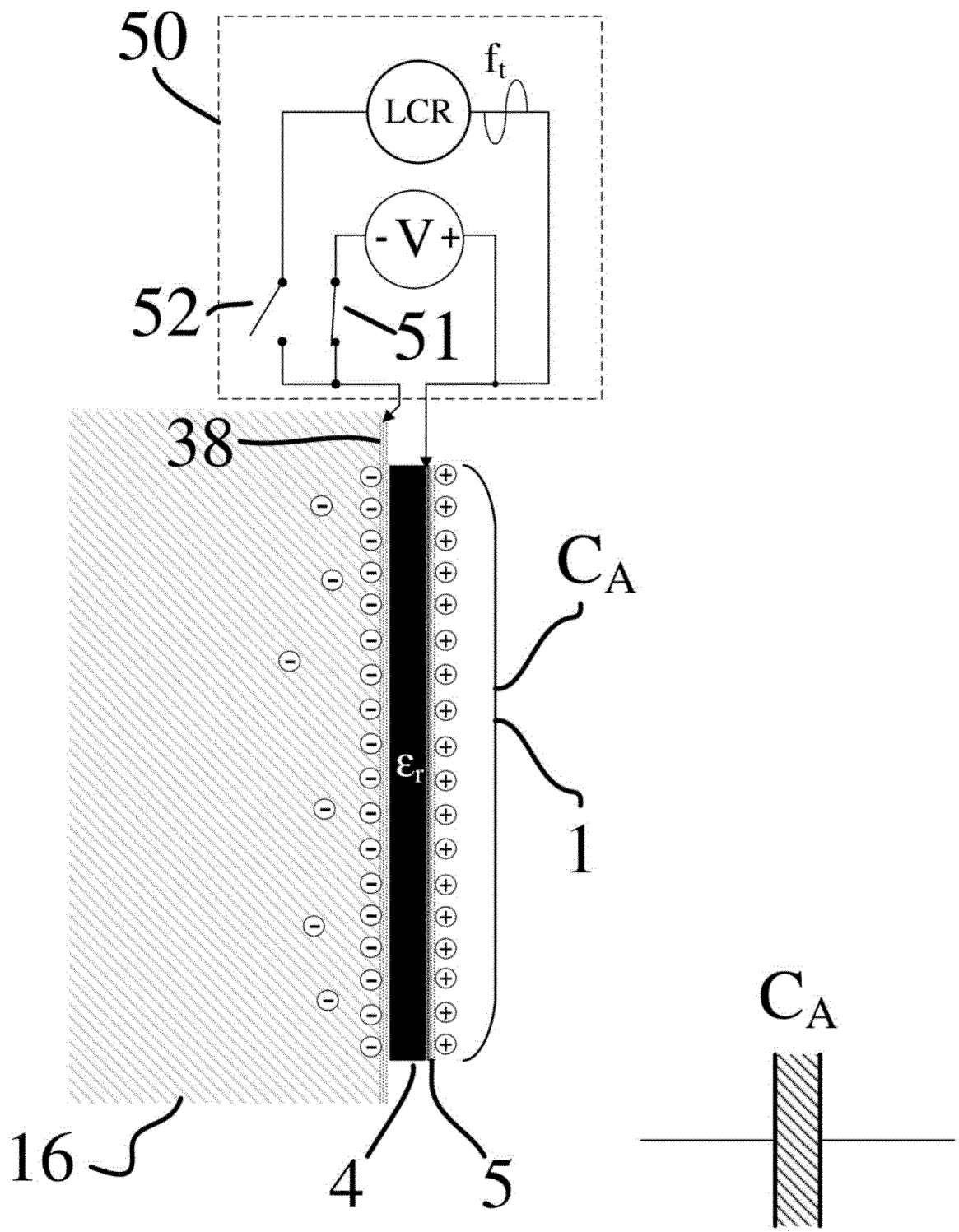
FIG. 10A FIG. 10B

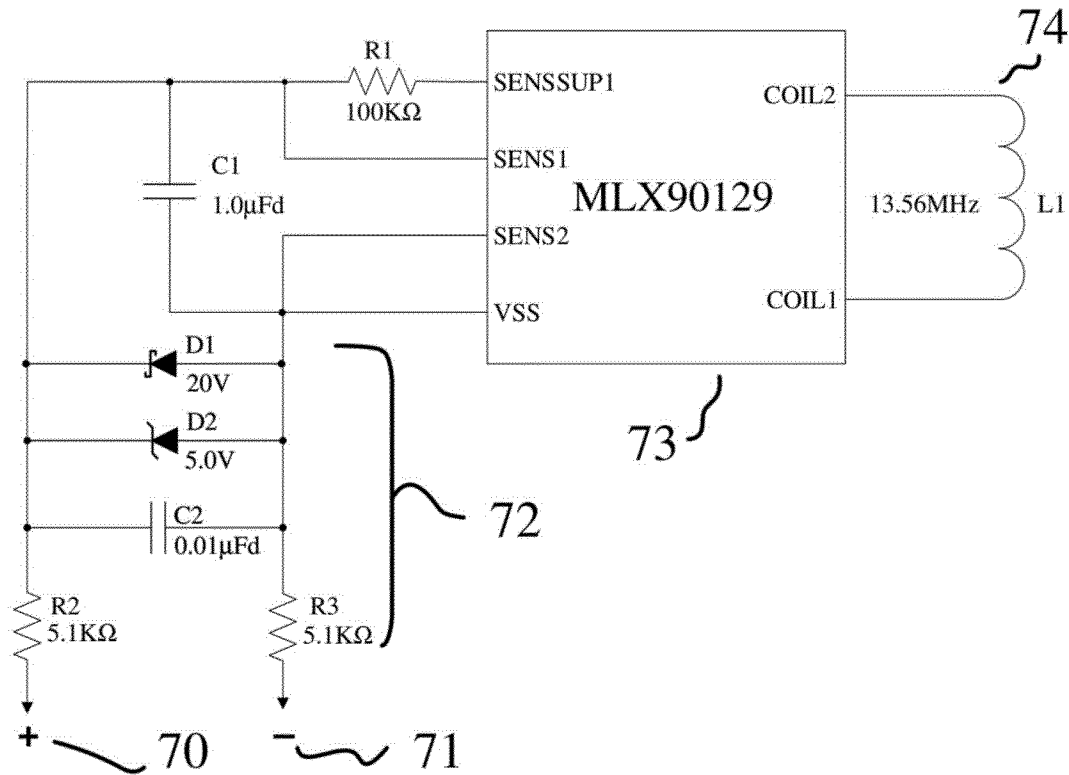
FIG. 14A
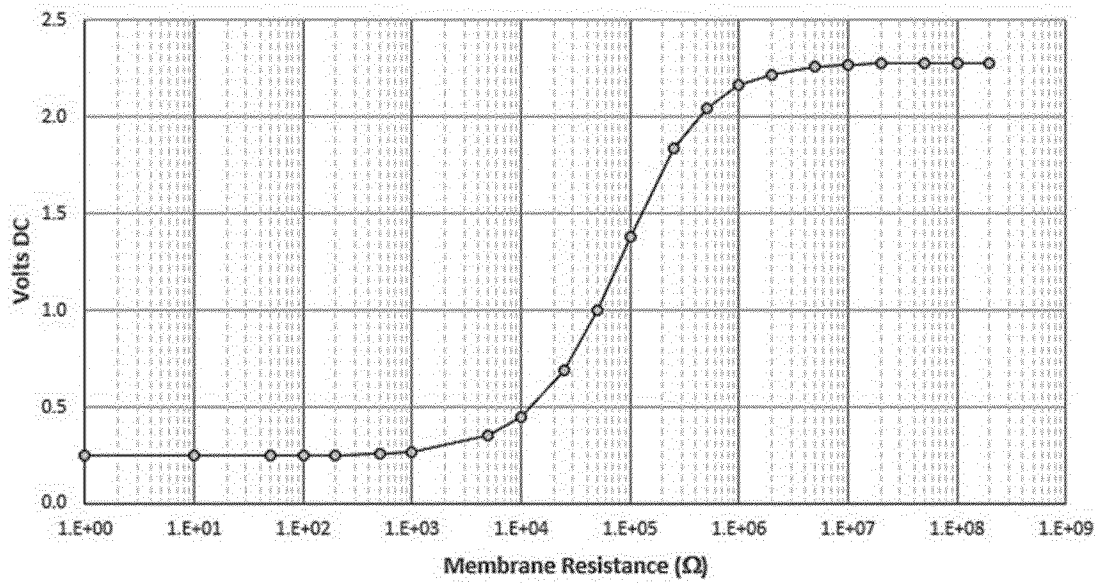
FIG. 14B

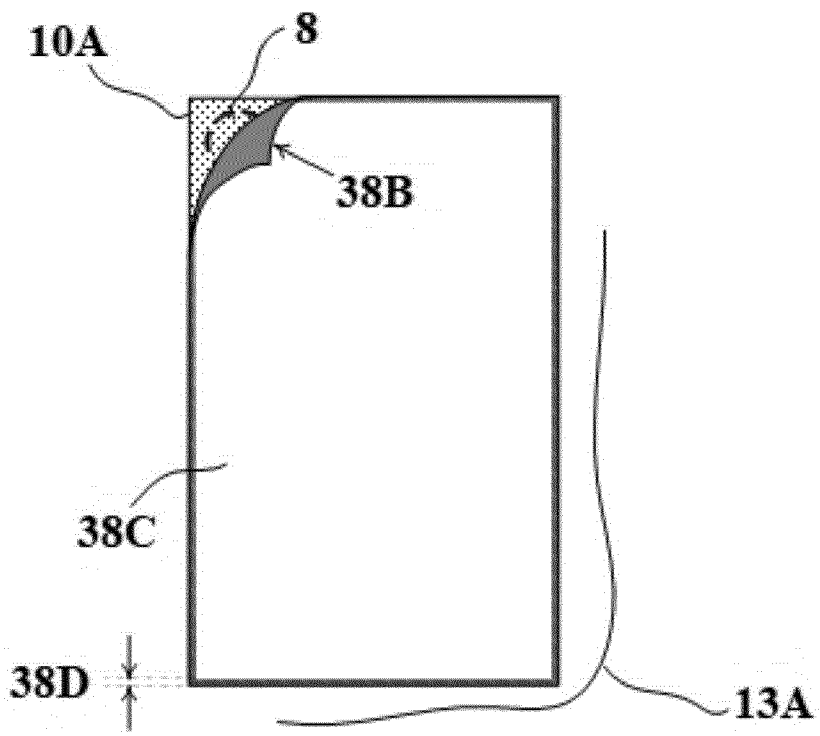
FIG. 15B
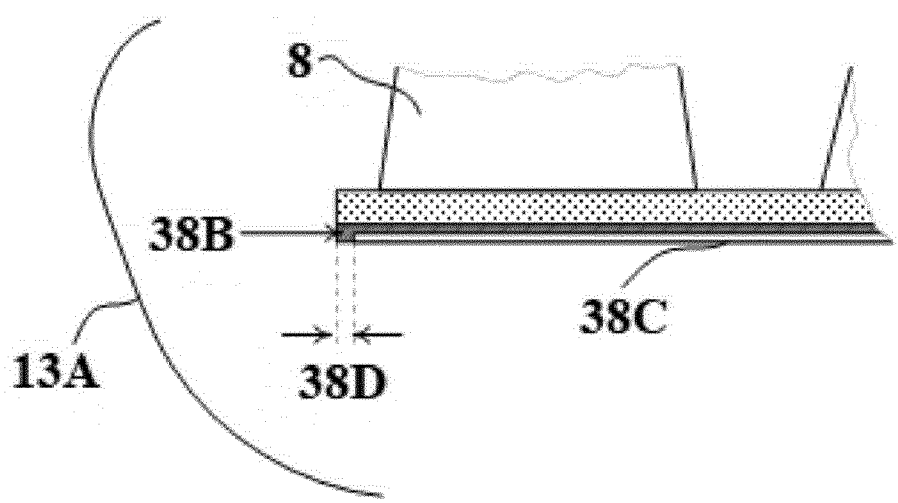
FIG. 15C

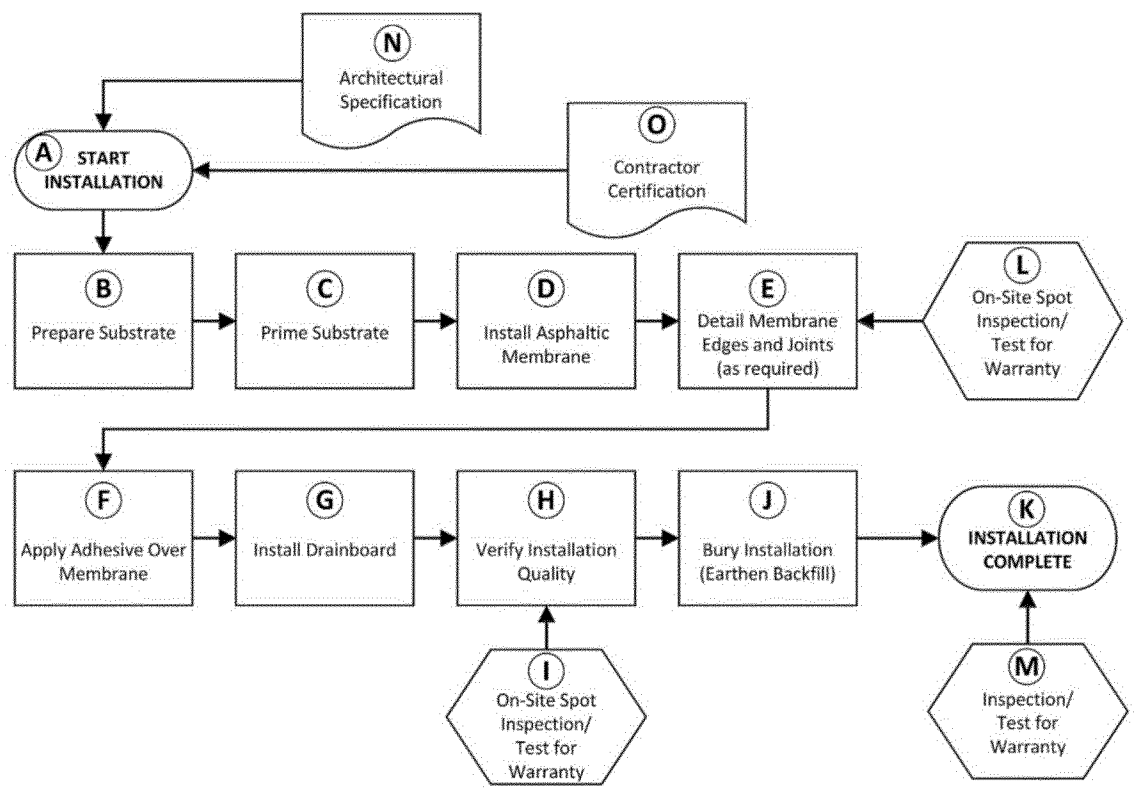
FIG. 16A
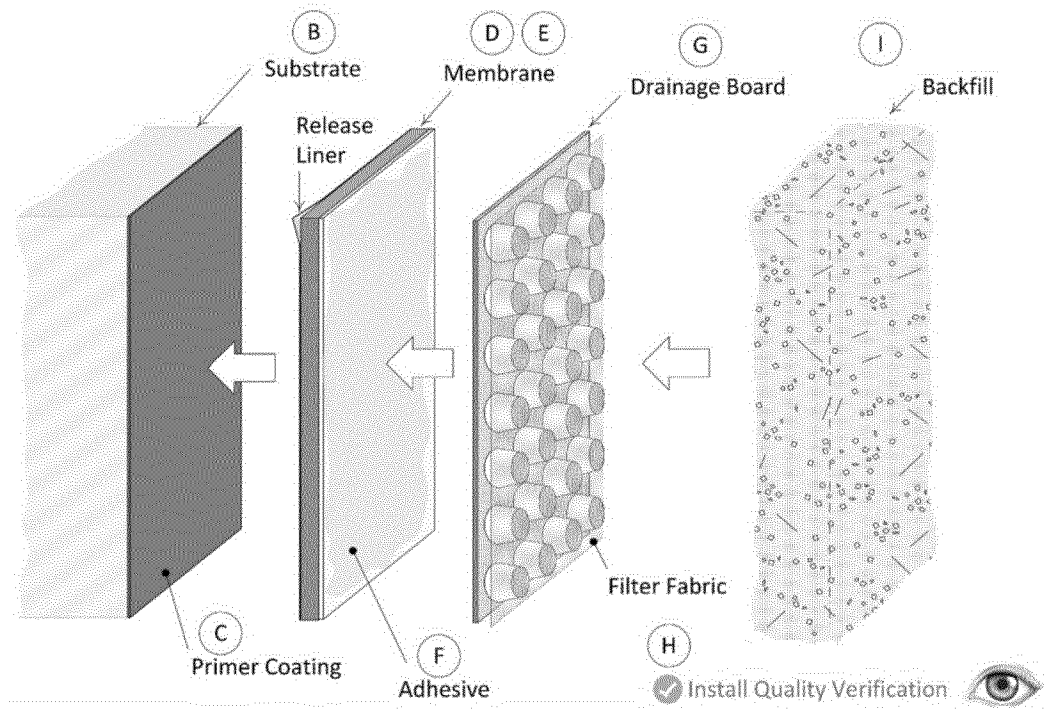
FIG. 16B

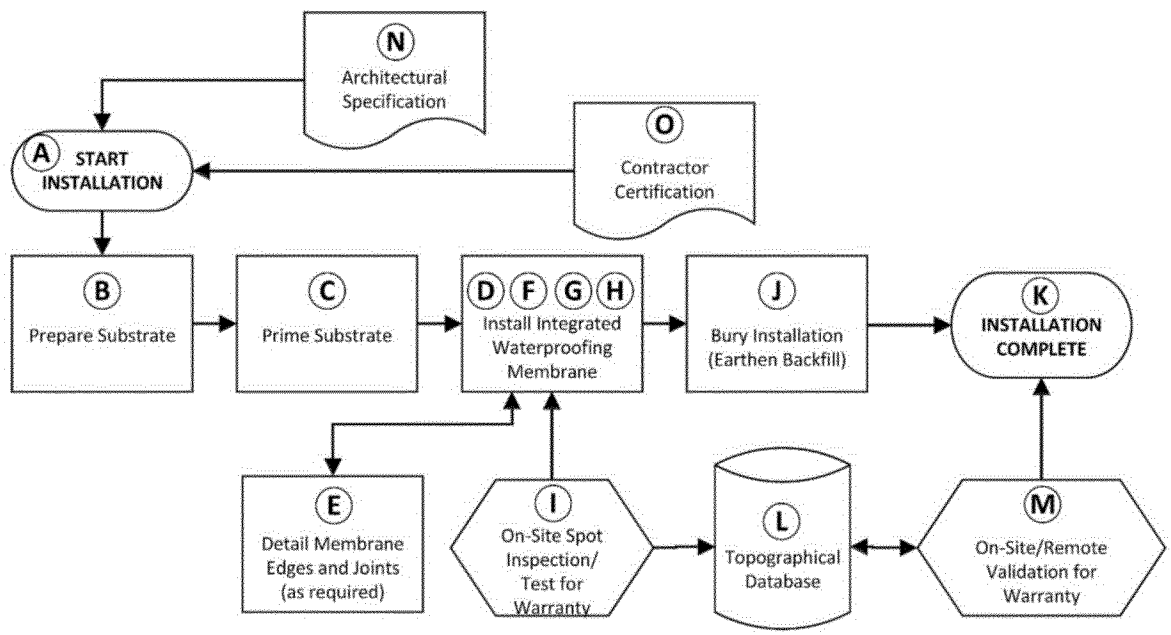
FIG. 17A
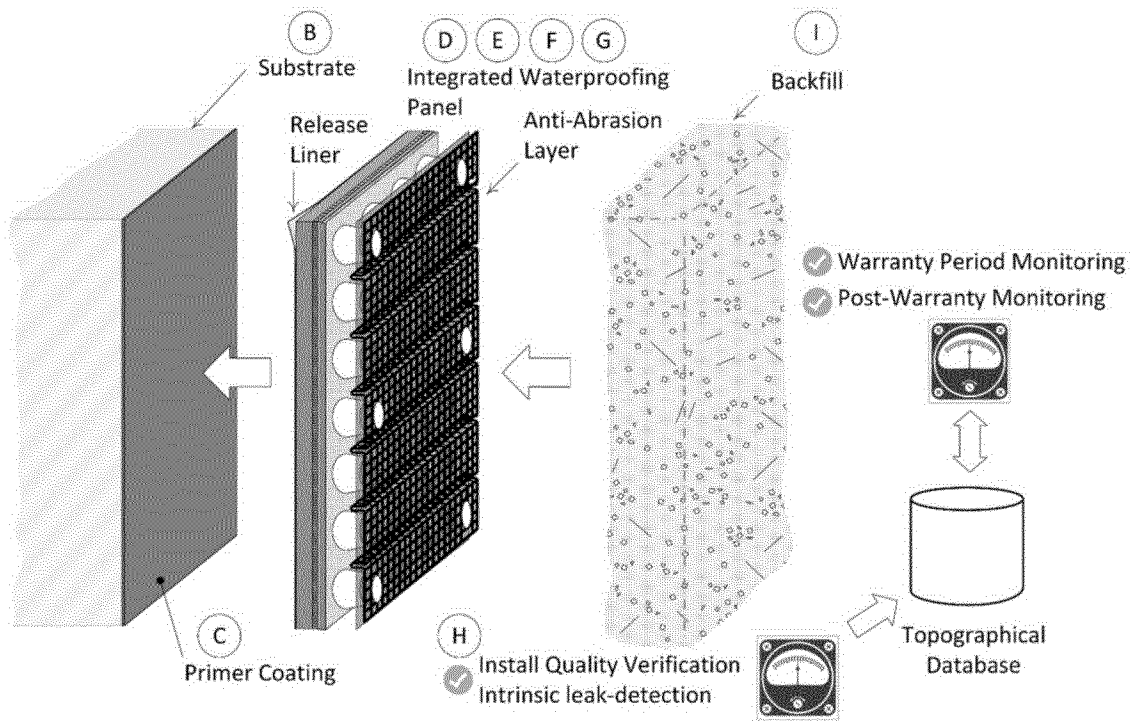
FIG. 17B

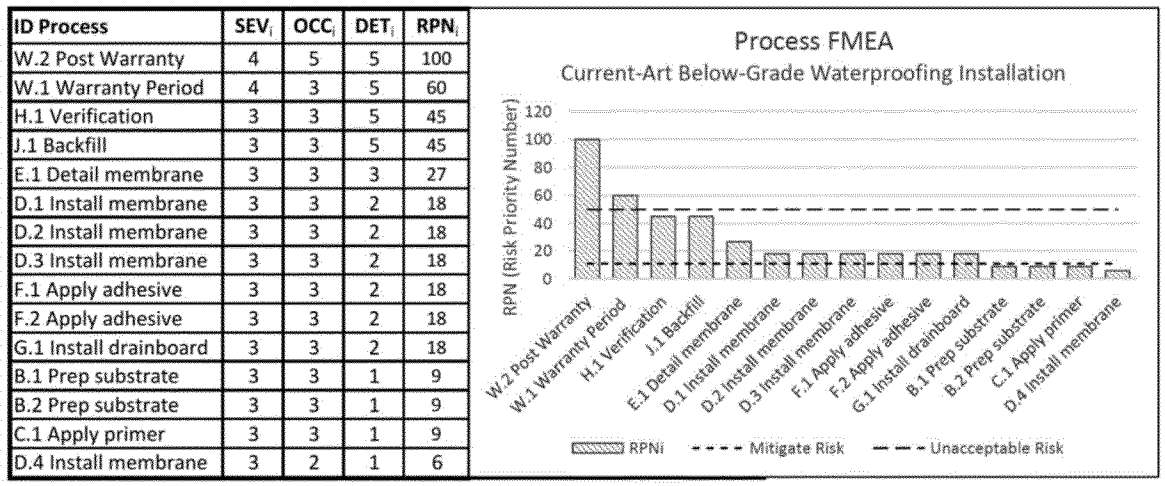
FIG. 18
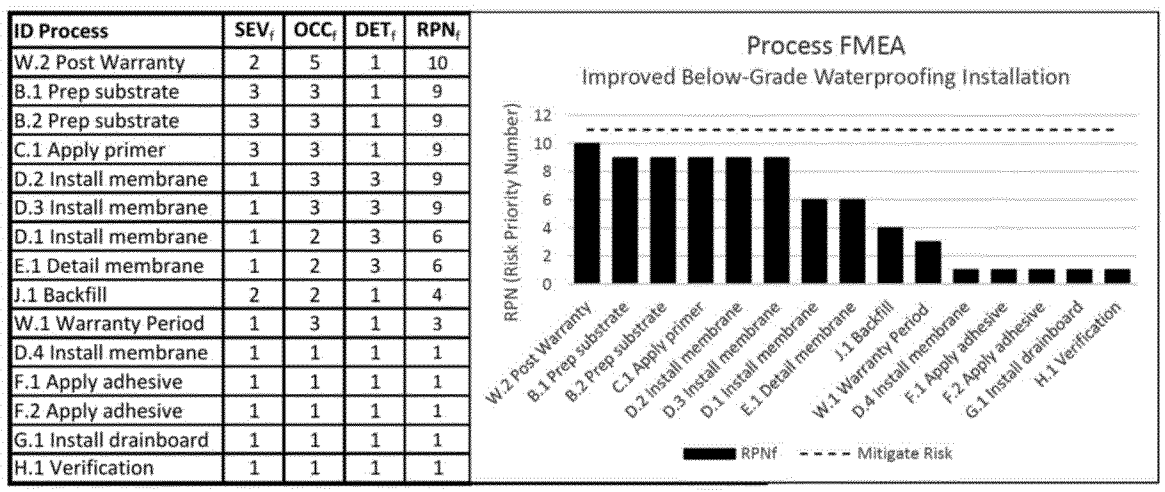
FIG. 19 addition, there can also be an electrical conduit that couples the electrically-conductive membrane layer or metal strips to an electrical-condition-measurement device. In even more variations, the improved waterproofing-panel assembly also comprises a fluid-applied membrane on the target building's concrete substrate.

In embodiments, an electrical-condition-measurement device measures an external resistance to provide: (a) intrinsic leak-detection capability, (b) monitoring of a functional topography of the composite waterproofing membrane, (c) an inference to confirm whether the composite waterproofing membrane contacts the building's surface, and (d) combinations thereof. In addition, the improved waterproofing-panel assembly can further comprise a conductive primer positioned between the proximal surface side and the building's surface, and an electrical conduit that couples the conductive primer to an electrical-condition-measurement device, wherein the electrical-condition-measurement device measures an external resistance to provide: (a) intrinsic leak-detection capability, (b) monitoring of a functional topography of the composite waterproofing membrane, (c) an inference to confirm whether the composite waterproofing membrane contacts the building's surface, and (d) combinations thereof.

In various applications, the electrical-condition-measurement device is selected from the group consisting of a hand-held ohmmeter, a capacitance measurement using an LCR meter, and a permanently wired voltage and leakage-current device. In an embodiment, the improved waterproofing-panel assembly appends, attaches, adheres, secures, or connects to the building's surface without penetrating the composite waterproofing membrane. The improved waterproofing-panel assembly is adapted to contact soil, sand, rocks, gravel, clay, water, or combinations thereof, wherein the building's surface is selected from the group consisting of a basement floor, a slab, a subterranean basement vertical wall, a partially subterranean basement vertical wall, a basement vertical wall, and a slab's side surface. Further, in variations, the improved waterproofing-panel assembly can also comprise an anti-abrasion layer over the filter fabric.

The method of installing the improved waterproofing-panel assembly comprises appending, attaching, adhering, securing, or connecting an improved waterproofing-panel assembly to a building's surface without penetrating the composite waterproofing membrane and applying pressure to the improved waterproofing-panel assembly. In some embodiments, the method also entails connecting the electrical conduit that couples the electrically-conductive membrane layer or metal strips to the electrical-condition-measurement device or applying the conductive primer positioned under the interior-surface side, and connecting the electrical conduit that couples the electrically-conductive membrane layer or metal strips to the electrical-condition-measurement device or connecting the second electrical conduit to the electrically-conductive membrane layer or metal strips to the electrical-condition-measurement device.

Ideally, using Building Information Modelling (BIM) techniques, the improved waterproofing-panel assemblies are pre-fabricated under factory-controlled conditions that eliminates most of the construction-site flaws, variations, and inconsistencies that cause bad installations. These factory-pre-fabricated improved waterproofing-panel assemblies can be precisely joined in the field to create a final below-grade waterproofing structure, though as for any in-field installation specific installation detailing, including the proper sealing at interface joints between sections being installed, will still have to be performed.

The foregoing Brief Summary is intended to merely provide a short, general overview of the inventive disclosure described throughout this patent application, and therefore, is not intended to limit the scope of the inventive disclosure contained throughout the balance of this patent application, including any appended claims and drawings.

BRIEF DESCRIPTION OF THE APPENDICES AND DRAWINGS

The following is a brief description of the Appendices and Drawings provided to support the inventive disclosures herein, and it must be noted that these illustrations are not to scale and are simply intended to convey the basic mechanical structures of the apparatus depicted:

Appendix A Provides a formal process Failure Modes and Effects Analysis (FMEA) worksheet for the improved commercial building waterproofing system.

FIG. 1A depicts one embodiment of an exploded view of a corner section the improved waterproofing panel membrane with its various components.

FIG. 1B depicts one embodiment of the details of the improved waterproofing membrane with its various layers.

FIG. 1C depicts one embodiment of the structure of the conductive components inside the improved waterproofing membrane.

FIG. 2 depicts one embodiment of a view of a partially assembled section of the improved waterproofing membrane and the drain panel assembly.

FIG. 3 depicts one embodiment of a view of a fully assembled section of the improved waterproofing membrane and the drain panel assembly.

FIG. 4A depicts one embodiment of the installation details of the improved waterproofing system with inside and outside corner assemblies.

FIG. 4B depicts one embodiment of the cross-sectional details of the inside-corner assembly of an improved waterproofing system from FIG. 4A.

FIG. 4C depicts one embodiment of the cross-sectional details of the outside-corner assembly of an improved waterproofing system from FIG. 4A.

FIG. 5A depicts one embodiment of a cross-sectional view of a horizontal field joint that is used to vertically join drain panel assemblies of an improved waterproofing system end-to-end.

FIG. 5B depicts one embodiment of the detail of the horizontal field joint depicted in FIG. 5A.

FIG. 6A depicts one embodiment of a top cross-sectional view of an improved waterproofing panel prior to installation.

FIG. 6B depicts one embodiment of a top cross-sectional view of an improved waterproofing panel installed on a concrete wall with under and over end-lap details to horizontally adjoining improved waterproofing panel assemblies on each side.

FIG. 7A depicts one embodiment of a vertical installation of the drain panel assembly of an improved waterproofing system on an existing concrete wall.

FIG. 7B depicts one embodiment of the details of the waterproof-riveting configuration between the drain panel assembly anti-abrasion layer and the dimple board of an improved waterproofing system.

FIG. 8A depicts one embodiment of a cross sectional view of a horizontal under-slab installation of the drain panel assembly of an improved waterproofing system.

FIG. 8B depicts one alternative embodiment of a cross sectional view of a horizontal under-slab installation of the drain panel assembly of an improved waterproofing system.

FIG. 8C depicts a variation of the alternative embodiment of a cross sectional view of a horizontal under-slab installation of the drain panel assembly of an improved waterproofing system shown in FIG. 8B.

FIG. 8D depicts an embodiment of the rubberized-asphalt membrane (from FIGS. 8B and 8C) resistance characteristics, shown as a log-log relationship, for three different membrane thicknesses. These relationships apply for all installations; that is, both horizontal and vertical installations.

FIG. 8E depicts an embodiment of the rubberized-asphalt membrane (from FIGS. 8B and 8C) capacitance characteristics, shown as a log-log relationship, for three different membrane thicknesses. These relationships apply for all installations; that is, both horizontal and vertical installations.

FIG. 9 depicts one embodiment of a cross sectional view of a vertical blindside installation of the drain panel assembly of an improved waterproofing system.

FIG. 10A depicts one embodiment of an abstract rendering of the installation verification of an improved waterproofing membrane using a capacitance measurement.

FIG. 10B depicts one embodiment of the equivalent capacitor of the configuration depicted in FIG. 10A.

FIG. 11A depicts one embodiment of an abstract rendering of the installation verification of an improved waterproofing system using a capacitance measurement when there is a void between the waterproofing membrane and the concrete wall.

FIG. 11B depicts one embodiment of the equivalent capacitors of the configuration depicted in FIG. 11A.

FIG. 11C depicts another embodiment of the equivalent capacitors of the configuration depicted in FIG. 11A.

FIG. 11D depicts one embodiment of a schematic of the electrical model for the equivalent electrical circuit depicted in FIG. 11A.

FIG. 12 depicts one embodiment of an abstract rendering of the installation verification of an improved waterproofing membrane using a leak-detection measurement using resistance.

FIG. 13 depicts one embodiment of a block diagram of the electronic leak-detection method.

FIG. 14A depicts one embodiment of a simplified electronic schematic using an existing RFID sensor chip for an improved waterproofing system.

FIG. 14B depicts one embodiment of a graphical representation of the output response for simplified electronic schematic using an existing RFID sensor chip for an improved waterproofing system depicted in FIG. 14A.

FIG. 15A depicts one alternative embodiment of an exploded view of a corner section the improved waterproofing panel membrane with its various components, wherein this particular embodiment also features a fluid-applied membrane.

FIG. 15B depicts a posterior view of FIG. 15A's alternative embodiment of an exploded view of a corner section the improved waterproofing panel membrane with its various components, wherein this particular embodiment also features a fluid-applied membrane.

FIG. 15C depicts a side cross-sectional view of FIG. 15A's alternative embodiment of an exploded view of a corner section the improved waterproofing panel membrane with its various components, wherein this particular embodiment also features a fluid-applied membrane.

FIG. 16A depicts a typical overall current-art process flow for the installation of a prior-art waterproofing panel system.

FIG. 16B diagrams the steps in FIG. 16A. (A corner fragment is shown, with the drawing not to scale.)

FIG. 17A depicts an embodiment of an improved process flow for the manufacturing and installation of an improved waterproofing panel system.

FIG. 17B diagrams the steps in FIG. 17A. (A corner fragment is shown, with the drawing not to scale.)

FIG. 18 depicts the current-art initial process risk assessments for each identified potential failure mode, and are graded from highest to lowest.

FIG. 19 depicts one embodiment of the initial process risk assessments for each identified potential failure mode for an improved waterproofing system manufacturing and installation process, and are graded from highest to lowest.

DETAILED DESCRIPTION

I. Overview

The inventive disclosures contained herein are designed to address the limitations of the above-identified existing art. To improve and/or eliminate the variation in installation quality from the layered multistep field-installation of commercial waterproofing systems, the job-site assembly technique is replaced with a factory-controlled process that bonds geocomposite drainage panels to waterproofing membranes prior to installation. Additionally, a filter layer of each geocomposite drainage panel is mechanically captured by a factory-applied outer perforated anti-abrasion layer made from the same material as the core of the drainage panel, which acts to protect the filter material from puncturing and tearing. Finally, the waterproofing membrane incorporates an electrically conductive layer that allows the membrane itself to serve as an electronic sensor and provide a means for installation verification through capacitance measurement, characterization of the installation topography by capacitance and resistance measurements, and intrinsic post-installation functional validation (i.e., leakage detection) by resistance measurement. In even more variations, the improved waterproofing-panel assembly also comprises a fluid-applied membrane on the target building's concrete substrate.

In an embodiment, a factory-controlled process is used to bond high-impact polystyrene drainage panel cores to the polyethylene-reinforced side of a rubberized-asphalt waterproofing membrane using an industrial-grade chemically-compatible organic adhesive compound, preferably a low Volatile Organic Compound (VOC) adhesive compound, and on the opposing installation side of the waterproofing membrane, there is a pressure-sensitive adhesive (commonly referred to as a "peel and stick" adhesive) release liner of silicone, or a functionally equivalent non-stick material, for easy application of waterproofing membranes to existing concrete vertical walls, and depending on the application, there are also non-pressure-sensitive adhesive waterproofing membranes using a non-woven geotextile for blind-side vertical wall or under-slab floor installations. The waterproofing membrane can have various thicknesses, and typically ranges between 60 to 100 mils, depending on the application. The outer side of the drainage panel opposite to the waterproofing membrane has multiple layers of non-woven synthetic filter material such as polypropylene to protect the drainage channels from soil infiltration and clogging after installation and earthen back-fill. To trap and protect the filter layer from damage, and maintain the structural integrity of the filtering and drainage system, a perforated anti-abrasion layer made from high-impact polystyrene or any functionally equivalent fungus and rot-resistant material, is attached to the dimple tops of the drainage panel core using a plurality of non-protruding polystyrene fasteners in a leak-proof configuration, as well as an industrial-grade low-VOC adhesive. Because of the additional strength and mechanical stability afforded by the anti-abrasion layer, the waterproofing panel may also have pressure applied by a device such as a roller after installation. The drainage panel will also withstand normal construction traffic without damage during horizontal installations. The anti-abrasion layer also has a bend-relief feature in the form of transverse creases that provide the integrated panel with longitudinal flexibility to facilitate storage and shipment in rolls.

The pressure-sensitive adhesive drainage panel with an integrated filter, offers the advantage of replacing the field-applied wet adhesive with a factory-controlled adhesive layer, thereby negating the need for application of the wet adhesive in the field, and eliminating the variations in curing times and quality of the wet adhesive that typically arise from environmental factors such as ambient temperature, humidity and particulate contamination resulting from wind-borne material such as dust and various types of organic matter. Furthermore, because the waterproofing drainage panel also includes the anti-abrasion protective layer, the added lateral stability during installation effectively eliminates the conditions favoring the creation of wrinkles and fish mouths in the waterproofing membrane. Panel-to-panel vertical seams are sealed with overlapping end laps that create a fully adhered bond between waterproofing membranes, along with an overhanging filter and anti-abrasion layers feature that extends past the dimple top, shingling over the leading edges of adjacent panels, preventing soil infiltration after the system has been installed. Panel-to-panel horizontal seams are made using factory-made polystyrene core field joints that have a self-adhesive peel-and-stick rubberized-asphalt backing and a single or double-sided adhesion flaps that form watertight interfaces to each panel's waterproofing membrane, as well as pressure-sensitive adhesive strips on the upper surface of the joint that act to reinforce the membrane termination. To provide protection after the horizontal joint has been detailed, a polystyrene cap strip is installed afterward, which also serves to prevent soil infiltration into the drainage panel core. Additionally, the system provides factory-made inner and outer corner vertical end-laps with a core structure and termination method identical to the horizontal panel field joint, and these inner and corner end-laps are compliant to variations in the corner angles of the substrate. Furthermore, the inner corner end-lap may also be used horizontally as the termination joint at the wall-to-footer Interface. The field joint, end-lap and footer termination structures are designed to facilitate the application of detailing cant beads at the exposed membrane end-seams. Finally, vertical-panel seams from cuts made in the field are over-lapped with composite strips of anti-abrasion material and filter fabric to seal these irregular joint openings.

A variety of factory-made standardized accessories allows for the accommodation of penetrations and other variables encountered during installation. For single penetrations, standardized half-pieces are used to fit around the penetrating pipe or conduit, and these have panel interfaces that are similar to those used for the vertical and horizontal terminations described above. For multiple or irregular penetrations, a cofferdam may be installed around the penetrations using a selection of various lengths of corner pieces, with panel-sided interface features similar to those described above. A dam feature is incorporated that acts as a form to allow liquid waterproofing material to be poured around the penetrations and to be held in place until the material has cured. When installed on a properly detailed and primed substrate, this waterproofing system is designed to eliminate the typical quality problems arising from the human-factor and environmental variation during field installation. The factory-controlled process that integrates the waterproofing membrane and drainage panel, facilitates an inherently wrinkle and void-free application of the membrane to the substrate. Furthermore, only one process step—the pressure-sensitive adhesive operation—is required during the installation, thereby saving labor hours and significantly reducing the time required to finish the job. The variety of factory-made field joints allows high-quality terminations and panel unions to be made at the inside and outside corners, footers and between panels, while the integrated drain panel provides built-in UV protection of the waterproofing membrane, which helps to simplify construction logistics since the waterproofing installation need not be buried within the typical 30 to 60 days. Furthermore, the integrated anti-abrasion layer eliminates any concerns of damage to the filter fabric during the earthen back-fill operation; conversely, any damage to a conventional drainage board filter layer that happens during the back-fill operation will not be detected until water stops flowing and hydrostatic pressure increases due to sediment-clogged drainage passages. For these reasons, the term 'Poka-Yoke' (mistake-proofing a process) can be applied to this waterproofing system.

In another embodiment, an electrically-conductive film of conductive-particle infused polyethylene augmented with strips of metallic mesh, is integrated onto the drainage panel side of the water proofing membrane under the protective polypropylene backing film, into which a continuous DC or time-varying AC low-voltage potential is introduced via an electrical interface at the top of the waterproofing panel. This conductive layer is used to provide the means for making the electrical measurements necessary for installation verification and functional validation by leakage detection of the waterproofing system. It should be recognized that a sufficiently fine metallic mesh, foil, or film may also be used to form the conductive layer itself without altering the function of this invention embodiment.

To prepare a concrete wall for the application of an improved waterproofing system, the already leveled and detailed concrete substrate is coated with a primer to seal the substrate. The preferred method for installation on existing vertical walls uses an electrically conductive primer, which is chemically compatible with the rubberized-asphalt waterproofing membrane, and exhibits a surface resistivity after application of between 50,000 and 250,000 ohms-per square. It must be noted that the electrically conductive primer is necessary for the installation verification measurement, but it would not be required for the leakage detection measurement.

Additionally, for blind-side installations and under-slab applications where the non-woven geotextile is used instead of the pressure-sensitive adhesive release liner, the conductive primer is not required. Rather, in these applications, the concrete wall or floor is poured in place against a pre-installed waterproofing system and for both of these applications without conductive primer, the leak detection measurement will still function.

AC voltage is used to assess the waterproofing membrane's dielectric behavior through the measurement of the panel with intrinsic leak detection is the surface that is applied to/facing the substrate (e.g., concrete building wall), and the anterior side of the integrated drain panel with intrinsic leak detection is the surface that has the anti-abrasion layer facing the earthen backfill.

As applicable, the terms "about" or "generally", as used herein unless otherwise indicated, means a margin of +−20%. Also, as applicable, the term "substantially" as used herein unless otherwise indicated means a margin of +−10%. It is to be appreciated that not all uses of the above terms are quantifiable such that the referenced ranges can be applied.

As used in this specification, drawings, and any appended claims, the term "below-grade" is a construction-industry term for below-ground or subterranean installations.

III. An Improved Building Foundation Waterproofing and Drainage System With Intrinsic Leak Detection Capabilities This Section III is directed to an improved waterproofing and drainage system with intrinsic leak detection for use in building structures, such as vertical and horizontal foundational structures that are disposed below ground. Refer to FIGS. 1A though 15C.

In an embodiment, the improved waterproofing-panel assembly 15 has a composite waterproofing membrane 1, a drain-board core 7, a filter fabric 9, an anti-abrasion layer 10; and a plurality of flat-topped high-impact polystyrene rivets 11. The drain board 7 prevents the build-up of hydrostatic pressure against a wall after installation of the improved waterproofing-panel assembly 15, and the filter fabric 9 prevents soil from clogging the drainage channels in the improved waterproofing-panel assembly 15. In variations, the drain-board core 7 can have a plurality of flat-topped dimples 8. In a typical application, the flat-topped dimples are comprised of a high-impact polystyrene with the ability to withstand a compressive loading of at least 18,000 lbf/ft$^2$ and provide a gravity-assisted, water-drainage flow of no less than 20 gallons/minute per foot of cross-sectional width. In many applications, the filter fabric 9 is comprised of a non-woven polypropylene material. Preferably, the filter fabric 9 is comprised of multiple layers of non-woven polypropylene material. In more variations, the anti-abrasion layer 10 is comprised of a perforated high-impact polystyrene sheet, preferably at least 60 mils in thickness. The anti-abrasion layer 10 allows a water flow rate of no less than 100 gallons/minute per ft$^2$ of area, with a plurality of transverse creases 12 to provide longitudinal flexibility.

In other embodiments, the composite waterproofing membrane 1 has a rubberized-asphalt layer 4. The rubberized-asphalt layer 4 has a proximal (that is, interior) surface side 104 positioned to be closer to a building wall, and a distal (aka, exterior) surface side 106 positioned on the opposite side of the interior surface side 104 as illustrated in the close-up view of a corner 2 of the waterproofing membrane 1 in FIG. 1B. The rubberized-asphalt layer 4 is commonly a mixture of rubber and asphalt—also called bitumen—and is reinforced on or over the exterior surface side 106 with a high-density polyethylene (HDPE) cross-laminated film backing 6. Positioned on or under the interior surface side 104 is a pressure-sensitive rubberized-asphalt adhesive coating 107 protected by a release liner 3. In many variations, the release liner 3 is comprised of a non-stick material such as silicon or treated paper. In some alternative variations, and depending on the application, the pressure-sensitive rubberized-asphalt adhesive coating 107 and release liner 3 may be replaced with a non-woven polypropylene fabric material.

In many embodiments, an electrically-conductive membrane layer 5 is laminated between the rubberized-asphalt layer 4 and the outer reinforcing film backing 6. Furthermore, a plurality of conductive metallic strips 79 approximately 0.5 inches in width are laminated between the electrically conductive membrane 5 and the HDPE (high-density polyethylene) cross-laminated film backing 6. The plurality of metallic strips 79 are longitudinally positioned in the waterproofing membrane 1, and are spaced transversely a predetermined distance. That predetermined distance is preferably every 8 inches or thereabouts. In many applications, the overall thickness of the composite waterproofing membrane 1 will range between 60 and 100 mils depending on the application.

In still more embodiments, the electrically conductive membrane layer 5 has an additional thin layer of carbon-impregnated HDPE film, typically 2 to 3 mils in thickness, that is chemically compatible with the rubberized-asphalt, with a surface resistivity of approximately 500 ohms per square. In many variations, the metallic strips 79 are composed of Type-316 type stainless steel with a count ranging from 80 to 120 wires per inch, and a wire diameter of less than 5 mils, although metalized plastics such as aluminum-coated polypropylene film or purely metal films such as aluminum foil may also be used to provide the same function. Together, the electrically conductive membrane layer 5 and the woven-metal-mesh strips 79 are bonded to form a sensing element 150 within the composite waterproofing membrane 1, where (a) the electrically conductive membrane layer 5 provides generally conductive layer throughout the waterproofing membrane, while (b) the woven metal mesh strips 79 improve the conductivity along the length of the waterproofing membrane 1 roll and also provide an electrical connection point to the waterproofing membrane 1. The dimensions and spacing of the conductive film 5 and metal mesh strips 79 may be altered without changing or altering the function of these components. Similarly, in a preferred embodiment, different conductive materials such as metalized plastic films and metallic foils may also be substituted for either component without substantially altering the electrical function of the sensing element. FIG. 1C reveals an embodiment of how the metallic strips 79 are arranged within the composite waterproofing membrane 1 and shows a corner fragment of the composite waterproofing membrane 1. The view of this illustration is a view of the exterior side surface of the of the waterproofing layer 1 wherein most of the cross-laminated HDPE backing layer 6 is shown peeled away except for the fragment to the left. The peeled-away backing layer 6 exposes the electrically conductive membrane 5. A small portion of the electrically conductive membrane 5 is also peeled away to expose the rubberized-asphalt waterproofing layer 4 below.

In still more embodiments, and referring still to FIG. 1C, the metal mesh strip 79 with width $W_1$ of the preferred embodiment appears above the electrically conductive membrane 5 because the metal mesh strip 79 is laminated between the electrically conductive membrane 5 and the cross-laminated HDPE backing layer 6 (which peeled away). An optional metalized foil or plastic strip 80 is also shown for reference purposes, and in this view, the metalized of side of the plastic strip is oriented downward to make electrical contact with the electrically conductive membrane 5. Furthermore, the foil or metalized plastic strip 80 is shown with a rounded zigzag pattern to provide longitudinal strain relief within the composite waterproofing membrane 1, and the magnitude of the pitch of this zigzag pattern would be defined by width $W_2$. The distance between the center-lines of the metallic strips is defined by distance $D_0$; in the preferred embodiment, width $W_1$ is 0.5 inches and distance $D_0$ is 8 inches. It should be understood that these dimensions may be altered to optimize the characteristics of the sensing elements within the composite waterproofing membrane 1 for maximum performance of the associated external electronic measurement devices.

In an embodiment of an assembled improved waterproofing membrane 1 and the drain panel 13 assembly, the assembled geocomposite drain panel 13 (which is the drain-board core 7, the filter fabric 9, and the anti-abrasion layer 10) has installed 14 reinforcing rivets 11. In variations, the filter fabric 9 is secured between the drain-board core 7 and the anti-abrasion layer 10 by using an industrial-grade chemically-compatible low volatile organic compound (VOC) adhesive to adhere to the dimple tops 8 of drainboard core 7. Additionally, a plurality of rivets 11 are installed 14 through the anti-abrasion layer 10 into existing holes on a fraction of the plurality of dimple tops 8 of drain core board 7. FIG. 7B illustrates an embodiment of the detail of an installed rivet 14 configuration detail, wherein the rivet 11 has been flared under the dimple of the drain-board core 7 to firmly reinforce the attachment of the anti-abrasion layer 10, and wherein the industrial-grade chemically-compatible low-VOC adhesive 40 has been used to fill the inside end of the dimple tops 8 of drain-board core 7 to provide a leak-proof joint. Additionally, the industrial-grade chemically-compatible low-VOC adhesive 40 is used at all the dimple tops 8 of drain-board core 7 contact points with anti-abrasion layer 10. In variations, the ratio of the plurality of drain-board core 7 dimples 8 to the plurality of rivets 11 and 14 may range between 4:1 and 10:1 depending on the application. The ratios depicted in the Figures indicate a ratio of 4:1. In many embodiments, the mechanical pull-strength strength of the drain-board core 7 and anti-abrasion layer 10 preferably exceeds 400 $lbf/ft^2$.

In embodiments, the improved waterproofing-panel assembly 15 features a geocomposite drain panel 13 that is attached to the cross-laminated film backing 6 (see FIG. 1B) using an industrial-grade chemically-compatible low-VOC adhesive (typically, the bond strength is less than 1,000 $lbf/in^2$, as applicable for non-structural adhesives). In such embodiments, the overall thickness of the improved waterproofing-panel assembly 15 is approximately 0.5 to 0.6 inches (0.062+0.40+0.062, membrane+drain-board core/filter+anti-abrasion layer).

In even more embodiments, the improved waterproofing-panel assembly 15 is installed on concrete or cinder-block wall 16 (see FIG. 4A), while FIGS. 4B and 4C illustrate more information about outside and inside vertical corner details 21 and 20 respectively. A factory-made inside-vertical corner 17 (see FIGS. 4A and 4B) and outside-vertical corner 19 (see FIGS. 4A and 4C) allow the improved waterproofing panels 15 to be joined, preferably vertically joined, at a corner 160 of the wall 16 (see, e.g., FIG. 4C) or plurality of walls 16 (see, e.g., FIG. 4B) to create a water-tight seal. In example embodiments as shown at FIGS. 4B and 4C, high-impact polystyrene cores 24 and 29 are positioned at the corner 160 which creates a first wall surface 162 and a second wall surface 164. The first and second wall surfaces 162, 164 can be at 90-degree angles, as illustrated in FIGS. 4A and 4B, or any angle used in a polygonic structure.

In still more applications, each high-impact polystyrene cores 24 and 29 has at least two polymeric (and preferably polystyrene) flaps 240, 242. The flap 240 is designed to be applied to the first wall surface 162; while the flap 242 is designed to be applied to the second wall surface 164. If the first and second wall surfaces 162, 164 are at right angles, then the flaps 240, 242 are opposed at 90 degrees. The polystyrene flaps 240, 242 are compliant and the 90-degree flap angle is easily changed to accommodate variations in the wall angle. Each flap 240, 242 is backed with a release liner 3 that exposes a pressure-sensitive rubberized-asphalt adhesive 25 to attach the vertical corner pieces 17 and 19 to the wall 16. The width of the rubberized-asphalt membrane 25 on the wall 16 side of inside and outside vertical corners 17 and 19 is about 6 inches, and this is indicated by dimensions $D_2$ and $D_4$ in FIG. 4A. There are also pressure-sensitive adhesive rubberized-asphalt strips 26 on the front surfaces of the polystyrene flap surfaces 240, 242 opposite the wall 16, which create a reinforced under-lap bond with the over-lapped rubberized-asphalt membrane 1 of waterproofing panel 15. In many variations, the width of the inside and outside vertical corner polystyrene flaps 240, 242 is about 4 inches as indicated by dimensions $D_1$ and $D_3$ in FIG. 4A, and these dimensions each represents the length of end-lap engagement between the rubberized-asphalt membranes 26 of the inside 17 or outside 19 corners and the rubberized-asphalt membrane 1 of waterproofing panel 15. In typical applications, industrial adhesive and sealant such as mastic is used to detail the ends and edges of the waterproofing membrane 1 by forming vertical canted beads 22, 28, as indicated by FIGS. 4B and 4C, respectively. Prior to the application of the inside vertical corner 17, the seam in wall 16 is sealed using an industrial polyurethane sealant 23 as indicated, e.g., in FIG. 4B. To seal the end of the drain-board core 7, factory-made outside 18 and inside 17 corner caps comprised of anti-abrasion material are placed over the detailed 90-degree joints using a pressure-sensitive adhesive with release liner 3.

In many embodiments, the improved waterproofing panel assemblies 15 are vertically joined using a seam 30 (see FIGS. 5A and 5B) between the adjacently installed waterproofing panels 15. In some variations, groups of improved waterproofing panel assemblies 15 are joined via such seams 30 in a controlled factory setting, while in other variations, adjacent improved waterproofing panel assemblies 15 are joined via such seams 30 in the field during installation at a building site. The seam 30 is closed using a factory-made horizontal field joint using a similar configuration to the inside 17 and outside 19 vertical corners as depicted in FIGS. 4A, 4B, and 4C, except the polystyrene flaps 25 are opposed at 180 degrees from each other with a length of about 6 inches as represented by dimension $D_6$ in FIG. 5A and the polystyrene flaps 25 are attached to the polystyrene core 31, which has a pressure-sensitive adhesive rubberized-asphalt backing 25 and single-sided or double-sided adhesion flaps that form water-tight interfaces to each improved waterproofing-panel assembly's 15 waterproofing membrane 1, as well as pressure-sensitive rubberized-asphalt adhesive strips 26 on the upper surface of the joint that act to reinforce the membrane 1 termination. This under-lap length is about 4 inches and is indicated by dimension $D_5$ in FIG. 5A. This configuration provides an electrical conduit 34, like a wire, to electrically connect the conductive membrane layer 5 of the composite waterproofing membrane 1 across the horizontal joint 30. Horizontal canted beads of adhesive sealant 32 such as mastic seals and protect the horizontal edges of the improved waterproofing-panel assembly's 15 waterproofing membrane 1. In variations, to provide protection after the horizontal joint has been detailed, a polystyrene cap strip 33 is installed to prevent soil infiltration into the drainage panel core, and the polystyrene cap strip 33 also provides flow channels 35 that allow a gravity-assisted water drainage flow of no less than 20 gallons/minute per linear foot across the horizontal field joint 30.

In still more embodiments, the improved waterproofing panel assemblies 15 are horizontally joined using protruding flaps 75, 76 that overlap adjacent panels 15 (see FIGS. 6A and 6B, with FIG. 6A showing a top view of an improved waterproofing-panel assembly 15 in an uninstalled condition, and FIG. 6B showing a top view of adjacent improved waterproofing panel assemblies 15 joined together). In some variations, groups of improved waterproofing panel assemblies 15 are joined via such flaps 75, 76 in a controlled factory setting, while in other variations, adjacent improved waterproofing panel assemblies 15 are joined via such seams 75 in the field during installation at a building site. In variations, the protruding flap 75 on one side of an improved waterproofing-panel assembly 15 extends from the main lateral edge on the panel assembly 15 on one side by about 4 inches, as represented in FIG. 6B by distance $D_8$, with the pressure-sensitive rubberized-asphalt adhesive coating release liners 3 below and above the flap 75. On the other side, in variations, another flap 76 extends about 3 inches as represented in FIG. 6B by distance $D_8$ distance $D_7$ from the edge of the anti-abrasion layer 10 and filter fabric layer 9, which are attached to drain-board core 7. When the improved waterproofing panel assemblies 15 are installed on the wall 16 as illustrated in FIG. 6B, the composite waterproofing membrane 1 is under-lapped for distance $D_8$ below the adjacent panel's 15 composite waterproofing membrane 1, and the anti-abrasion layer 10 and filter fabric layer 9 is over-lapped for distance $D_7$ over the opposite adjacent panel's composite waterproofing anti-abrasion layer 10. In a typical installation, the installed waterproofing panels are rolled with roller 10 to apply pressure or other appropriate pressure is applied in order to ensure adhesion on all end-lap joints 75, 76. For covering irregular joints created by the necessity of cuts made in the field, a strip of anti-abrasion and filter fabric material 77 can be provided with a plurality of capture features 78 to engage and lock into the improved waterproofing-panel assembly's 15 anti-abrasion layer 10. Moreover, in variations, the capture feature 78 has a rounded end that will not damage the improved waterproofing-panel assembly 15 filter fabric layer 9.

In an embodiment, the in-field vertical installation of an improved waterproofing-panel assembly is depicted in FIGS. 7A and 7B, in which the concrete wall 16 and improved waterproofing-panel assembly 15 are shown in cross-section view, along with earthen back-fill 36. The cross-sectional views of FIG. 7A also shows the high-impact polystyrene drain-board core 7, the high-impact polystyrene anti-abrasion layer 10, which protects the filter fabric layer 9 during the application of earthen back-fill 36, and the transverse crease 12 feature in the anti-abrasion layer 10. Area 37 is shown in greater detail in FIG. 7B. A plurality of rivets 11 are installed 14 through the anti-abrasion layer 10 into existing holes on a fraction of the plurality of dimple tops 8 of drain core board 7. In a variation, the rivet 11 is flared under the dimple of the drain-board core 7 to firmly reinforce the attachment of the anti-abrasion layer 10, and wherein the industrial-grade chemically-compatible low-VOC adhesive 40 has been used to fill the inside end of the dimple tops 8 of drain-board core 7 to provide a leak-proof joint. Additionally, the industrial-grade chemically-compatible low-VOC adhesive 40 is used at all the dimple tops 8 of drain-board core 7 contact points with anti-abrasion layer 10. In additional variations, the ratio of the plurality of drain-board core 7 dimples 8 to the plurality of rivets 11 and 14 may range between 4:1 and 10:1 depending on the application. The ratios depicted in the Figures indicate a ratio of 4:1. In many embodiments, the mechanical pull-strength strength of the drain-board core 7 and anti-abrasion layer 10 preferably exceeds 400 lbf/ft². In many applications, the improved waterproofing-panel assembly 15 with composite waterproofing membrane 1 is applied over a conductive primer coating 38 applied to the concrete wall 16 surface. In variations, the conductive primer coating 38 meets the following criteria:

Compressive strength of about 7,800 psi ASTM D-695;
Tensile strength of 2,200-3,200 psi ASTM D-695 or ASTM D-638;
Elongation of about 2%;
Hardness Shore D of about 85 ASTM 2-2240;
Resistivity of 0.5-10.5 Mohms;
Static Charge Decay: 5,000-volt charge disperses to zero in less than 0.10 seconds;
Conductivity complies with DOD-HDBK-263 (Electrostatic Discharge Control Handbook for Protection of Electrical Parts, Assemblies & Equip.); and
Surface Resistance of <250 k ohms NFPA 99.

In some embodiments, the conductive primer coating is selected from the group of products consisting of Corobond™ Conductive Epoxy Primer available from the Sherwin-Williams Company, Stonhard™ Conductive Novolac Primer available from Stonhard, Inc., and Lexite™ Conductive Primer available from Metalcrete Industries.

In embodiments calling for horizontal under-slab installation of the improved waterproofing panels assemblies 15, as depicted in FIG. 8A, wherein the improved waterproofing-panel assembly 15 is applied prior to the pouring of concrete floor 43 with the anti-abrasion layer 10 disposed downward in contact with the earth 42. The improved waterproofing-panel assembly 15, with composite waterproofing membrane 1 and a non-woven polypropylene fabric layer 44, faces upwards and the floor concrete 43 is poured on top of the horizontal improved waterproofing-panel assembly 15. The cross-sectional view in FIG. 8A also shows the high-impact polystyrene drain-board core 7 and the high-impact polystyrene anti-abrasion layer 10, which protects the filter fabric layer 9 during the under-slab installation.

However, in some cases for under-slab installations, the making of panel-to-panel electrical connections to support intrinsic leak detection is not practical; therefore, a modification is required. The bulk resistance of the waterproofing membrane 1 will change as a function of waterproofing panel 15 surface area (i.e., the area in contact with the substrate 43 [e.g., concrete]). This can be used to help map the topography of an installed waterproofing system, because the bulk resistance and capacitance should correlate with the areas of the panels 15 that were installed. It should be noted that these relationships apply for all installations; that is, both horizontal and vertical installations. Unlike vertical installations on below-grade walls, under-slab installations will generally have a very large area to cover, and unless a roll of waterproofing-panel assemblies 15 is very large to allow it to go between each side of the building (such rolls will usually be too large and heavy to be practical), the under-slab sections must be put down in sections, which in turn necessitates that each waterproofing-panel assembly 15 either be electrically connected to its adjacent waterproofing-panel assembly 15 or that wires from each waterproofing-panel assembly 15 be extended to the perimeter of the structure. It should be noted that employing both of these options is generally impractical. To overcome this limitation, referring to FIG. 8B, the improved waterproofing-panel assembly 15 is further configured with an upper layer of non-woven geotextile material 44 placed against the ground 42, as in FIG. 8A, except that instead of pouring the concrete under-slab 43 directly on top, a layer of wire mesh 39 is first unrolled over an integrated drain panel 13 with waterproofing membrane 1; that is the improved waterproofing-panel assembly 15. In some variations, such a wire mesh 39 can be 40 AWG (American Wire Gauge). The gauge of wire in the mesh 39 needs to be small-enough, and the mesh 39 course enough, to keep the mass of a large roll below 25 lbs. (in some applications, the roll can be 300 ft. in length by 4 ft. in width). The mesh layer 39 is extended to the perimeter of the structure. In embodiments, the fine-wire mesh 39 can be made of any highly conductive metal such as copper or stainless steel. Any electrical connections to the mesh 39 are made by simply overlapping the fine-wire mesh 39 by at least 1 ft. Another asphaltic membrane 41 is applied (that is, unrolled) over/above the fine-wire mesh layer 41. This over-covering asphaltic membrane 41 has an upper layer of non-woven geotextile 44. In many variations, the lower surface of the over-covering asphaltic membrane 41 facing the fine wire mesh layer 39 is comprised of rubberized asphalt. The total thickness 47 of the two layers of rubberized asphalt 4 can vary. The ratio of the two is not critical, as long as the total thickness 47 is at least 60 mils.

FIG. 8C shows a variation of the embodiment of FIG. 8B with the lower waterproofing-panel assembly 15 replaced by another asphaltic membrane 48 with an upper layer of non-woven geotextile 44. The fine-wire mesh layer 39 is sandwiched between the asphalt layers 41, 48. This configuration is shown because some under-slab installations without basements (such as plazas) may eliminate the drainage panel 13. from the overall assembly 15.

In addition, the integrated drain panel with water proofing membrane 15 with intrinsic leak detection layer 5 can be used in a stand-alone under-slab application as shown in in FIG. 8B, but each end-to-end panel 15 joint will require an electrical connection to be made between the panel 15 conducting layers 5 in the field.

FIG. 8D depicts an embodiment of the rubberized-asphalt membrane (from FIGS. 8B and 8C) resistance characteristics, shown as a log-log relationship, for three different membrane thicknesses, and FIG. 8E depicts an embodiment of the rubberized-asphalt membrane (from FIGS. 8B and 8C) capacitance characteristics, shown as a log-log relationship, for three different membrane thicknesses. It should be noted that the relationships depicted in FIGS. 8D and 8E apply for all installations; that is, both horizontal and vertical installations.

In vertical blindside-installation applications, such as the embodiment depicted in FIG. 9, the improved waterproofing-panel assembly 15 is applied prior to pouring the concrete wall 16 with the anti-abrasion layer 10 facing the blindside scaffolding cross members 45. The plurality of perforations in the anti-abrasion layer allow a plurality of devices 46 such as strings or tie-wraps to be used to secure the improved waterproofing-panel assembly 15 vertically against the scaffolding cross members 45 through a plurality of openings 47 in the scaffolding cross members 45, thereby decreasing (and often eliminating) the need to secure the panel to blindside scaffolding cross members 45 using penetrating fasteners such as nails or screws. The improved waterproofing-panel assembly 15 with composite waterproofing membrane 1 and a non-woven polypropylene fabric layer 44 faces towards the wall concrete 16, which is poured behind the vertically oriented improved waterproofing-panel assembly 15. The cross-sectional view in FIG. 9 also shows the high-impact polystyrene drain-board core 7 and the high-impact polystyrene anti-abrasion layer 10, which also protects the filter fabric layer 9 during the blindside installation.

In an embodiment, as depicted in FIGS. 10A and 10B, an installation of an improved waterproofing system can be quality-controlled/leak-checked using capacitance measurement on a normal waterproofing membrane 1 and substrate configuration. The composite waterproofing membrane 1 is shown applied to a vertical concrete wall 16 onto which a conductive primer 38 has been applied to the surface of the concrete wall 16. A voltage source V within the test device 50 applies a DC voltage through switch 51 between the positively charged conductive membrane layer 5, and the negatively charged conductive primer 38, effectively creating capacitor $C_A$ with dielectric permittivity $\varepsilon_r$ for the rubberized-asphalt layer 4. The equivalent electrical circuit for capacitor $C_A$ is shown in FIG. 10B.

$$C_A = \varepsilon A/d = \varepsilon_r \varepsilon_0 A/d \qquad \text{(Equation 1)}$$

Where:
$\varepsilon$=dielectric permittivity
A=area of the capacitor plates (in this case the waterproofing membrane area)
d=distance between the capacitor plates (in this case the thickness of the rubberized-asphalt membrane)
$\varepsilon_r$=relative dielectric permittivity of the rubberized-asphalt membrane, approximately 3
$\varepsilon_0$=dielectric permittivity of free space, 8.854 . . . E-12 Farads/meter When switch 51 is opened and switch 52 closed, the LCR meter in test device 50 measures the components of inductance (L), capacitance (C) and resistance (R) of the capacitor $C_A$ formed by the conductive membrane layer 5, the asphalt waterproofing membrane 4, and the substrate conductive primer 38 with applied AC voltage at test frequency $f_t$. Furthermore, it is preferable that the LCR meter have a variable test frequency $f_t$. Additionally, because the physical configuration of the composite waterproofing membrane 1, there will be relatively large values of C and R when compared to L, and the composite waterproofing membrane 1 will behave much like a capacitor with a very high ESR (Equivalent Series Resistance). The values obtained for C and R can be used to characterize the dielectric behavior of the installed composite waterproofing membrane 1. Finally, in practical applications, only the variable frequency LCR meter is necessary to make this measurement on the composite waterproofing membrane 1. The voltage source V is only provided for illustrative purposes in FIGS. 10A and 11A to show how the composite waterproofing membrane 1 forms capacitor $C_A$ by holding electrical charge.

When installation verifications are performed on systems where there are one or more defects/voids, as illustrated in FIGS. 11A through 11C, the installation verification uses a capacitance measurement on an abnormal defective waterproofing membrane 1 and substrate configuration. FIG. 11A is identical to what was described for FIG. 10A except the installation of the composite waterproofing membrane 1 has been compromised by a void area 49 between the rubberized-asphalt waterproofing membrane 4 and the wall 16 substrate conductive primer 38, creating capacitor $C_B$ with dielectric permittivity $\varepsilon_r$ for the rubberized-asphalt layer 4 and dielectric permittivity near that of free space $\varepsilon_0$ for the voided area. The equivalent capacitors for the upper area without a void $C_{B1}$, and the lower area without a void $C_{B3}$, and the center area with the void $C_{B2}$ are shown in FIG. 11B. The equivalent electrical circuit for capacitors $C_{B1}$, $C_{B2}$ and $C_{B3}$ is shown in FIG. 11C.

$$C_B = C_{B1} + C_{B2} + C_{B3} \quad \text{(Equation 2)}$$

Where:
$C_{B2}$ will always be less than the capacitance of the voided area since:

$$1/C_{B2} = 1/C_{B2a} + 1/C_{B2a}$$

or $$CB2 = CB2a \cdot CB2b/(CB2a + CB2b) \quad \text{(Equation 3)}$$

And:
$C_{B2a}$=the capacitor formed by the void 49 with dielectric permittivity $\varepsilon_0$
$C_{B2b}$=the capacitor formed by the rubberized-asphalt waterproofing membrane 4 with relative dielectric permittivity $\varepsilon_r$.

Since the relative dielectric permittivity of rubberized asphalt has a value close to 3, and assuming the distance of the void 49 is the same as the thickness of the rubberized-asphalt waterproofing membrane 4, and assuming that the void is filled with air, then using Equation 3 above, the capacitance of $C_{B2}$ with the void 49 would be 25% of the capacitance of $C_{B2}$ without the void 49.

Factors such the distance and area of void 49 will affect this approximation, but the implication is that a void 49 of sufficient area would be detectable by measurements using an LCR meter as described above. Furthermore, a custom-designed capacitance sensing device would provide detection capability that could be optimized to the characteristics of the composite waterproofing membrane 1.

The schematic in FIG. 11D illustrates one approach used to computer-model the method for measuring the electrical effects described in FIG. 11C. The composite waterproofing membrane 1 of FIG. 11A is represented by an n-element series of lumped element resistors $R_{Mn}$ and capacitors $C_{mn}$, where $R_M$ represents the surface resistivity of the electrically conductive layer 5, $C_M$ represents the capacitance of the composite waterproofing membrane 1, and 'n' represents the nth element in the n-element series. $R_P$ and $R_C$ represent the surface resistivity of the electrically conductive primer 38 and volume conductivity of the concrete wall 16, respectively. The LCR device 50 provides a variable frequency AC voltage source with the capability to measure the time-varying current $I(\Omega t)$ through test impedance $Z_{LCR}$, which introduces the test current into the common input node feeding the electrically conductive layer 5 elements $R_{M1}$, $R_{M2}$, $R_{M3}$ ... $R_{mn}$ when LCR device 50 places a test voltage $V(\Omega t)$ between the common input node and the electrical ground 81. It should also be noted that the common input node electrically represents the conductive metallic strip 79 shown in FIG. 1C.

In one embodiment, the lumped-element model was partitioned into 8×8-inch squares for the rubberized asphalt layer 4 of thickness 100 mils, and the lumped membrane capacitance element $C_{Mn}$ was calculated as shown in FIG. 8E. Additionally, the electrically conductive layer 5 is assumed to have a DC resistance at or near zero, and each lumped membrane resistance element $R_{Mn}$ was calculated as shown in FIG. 8D. The electrically conductive primer 38 layer has a surface resistivity of 50,000 ohms per square, so each lumped primer resistance element $R_{Pn}$ was set to 50 kohms, assuming that each 8×8-inch square is continuously connected at the edges. Finally, the lumped concrete resistance element $R_{Cn}$ was set to 1000 ohms based a volume resistivity for the concrete substrate 16 equal to 1000 ohms and assuming continuous planar contact between the electrically conductive primer 38 layer and the concrete substrate 16.

The frequency-response sensitivities of the gain and phase of the LCR device 50 test voltage $V(\Omega t)$ and test current $I(\Omega t)$ were investigated using this lumped-element high ESR capacitance model by changing a series of capacitive elements as described in Equation 3 above to produce changes in lumped capacitance values within the model yielding the results summarized in Table 1 below:

TABLE 1

| | LCR Device Frequency-Response Sensitivities | | | |
|---|---|---|---|---|
| Change in capacitance | Δ Gain (dB) | Δ Gain (1-Ao/Ai) | Δ Phase (degrees) | Effective magnitude of voided area 49 on 4' × 10' waterproofing panel |
| 5% | 0.346 | 1.7% | 0.60 | 2 ft.2 or an area equivalent to 17" × 17" |
| 10% | 0.707 | 3.6% | 1.27 | 4 ft.2 or an area equivalent to 24" × 24" |

A change in gain of nearly 4% with a phase angle difference of 1.27 degrees is detectable with standard LCR instrumentation, and the nearly 2% gain and 0.60-degree phase-angle change could be detectable (based on the measurement uncertainty) with an LCR instrument that provides a variation in test frequency [see datasheet for NI 4072 6 ½-Digit Digital Multimeter, 1.8 MS/s Isolated Digitizer, and LCR Meter]. Difficulties would arise from panel-to-panel installation variation that would potentially reduce the signal-to-noise ratio and, therefore, the uncertainty in the measurement, which in turn would determine the minimum size of a voided area that could be quantitatively detected reliably. However, statistical methods such as, but not limited to, to logarithmic regression (log of resistance and capacitance vs. log of installed membrane area) and residual-error analysis (difference between observation and expectation) would allow a statistically out-of-family (OOF) normalized LCR measurement to be detected, which would effectively improve the detectability of this measurement method.

The installation verification using capacitance measurement is intended to detect areas of the composite waterproofing membrane 1 are not well attached to the concrete wall 16, but not small defects such as 'fish mouths', which is sufficient because the factory integrated nature of the improved waterproofing-panel assembly 15 eliminates the possibility of defects introduced through field installation such as 'fish mouths'.

In another embodiment, FIG. 12 provides an abstraction of a leakage-detection-verification method using electrical-resistance measurement on an installed waterproofing membrane 1. The improved waterproofing-panel assembly 15 is shown applied to a vertical concrete wall 16 onto which conductive primer 38 has been applied to the surface of the concrete wall 16. A voltage source V within the sensor device 53 applies a DC voltage through switch 54 between the conductive membrane layer 5 positive connection 58, and the negative connection 56a attached to the electrical earth ground 59 of the building structure. In one preferred embodiment, a current detector I within the sensor device 53 measures the electrical leakage current $I_{L2}$ flowing in series through the resistance $R_M$ of the asphalt waterproofing membrane 5 and then through the resistance Rc of the concrete structure 16. When a water leak compromises the composite waterproofing membrane 1, there will be a much lower water leakage resistance $R_L$ that will appear in parallel with the membrane resistance Rm. The measured leakage current $I_L$ will increase and provide indication that the composite waterproofing membrane 1 is either degrading or has failed. An alternate measurement path would be possible by attaching the negative connection directly to point 56b, which is the conducting primer 38 that is coating concrete wall 16 and measuring electrical leakage current $I_{L2}$. Additionally, by opening switch 54 and closing switch 55, electrical leakage current $I_{L3}$ could be measured, which is the return path through structure ground 59 and earth 36 at connection point 57 instead of directly from the structure's earth ground at 56a. In both cases, the structural concrete 16 provides the conduction path between the waterproofing membrane 1 and the structural earth ground 59. For reference, oven-dried concrete has a very high-volume resistivity, but once concrete has been exposed to earth and moisture, the volume resistivity of concrete drops to between 100 and 1000 ohm-meters (information obtained from U.S. Concrete Association). Soil volume resistivity varies with location, type, and moisture levels, but typically ranges between 100 and 5000 ohm-meters (see, e.g., MIL-HDBK419A: "GROUNDING, BONDING, AND SHIELDING FOR ELECTRONIC EQUIPMENT AND FACILITIES"). In both cases, due to the large contact areas of structures, the net parasitic resistances seen by the detection system are several orders of magnitude below the resistance of rubberized-asphalt membrane material, which is typically between 100 to 200 Mohms (1.+E8 to 2.+E8 ohms) (W.R. GRACE BITUTHENE® 6000 EIM SPEC SHEET).

The embodiment depicted in FIG. 12 also shows a detailing sealant material 60 covering the ends of the composite waterproofing membrane 1 which could be mastic-adhesive sealant or another suitable construction sealant, and this is necessary to prevent moisture from working its way under the edges of the rubberized-asphalt membrane 4 and degrading the bond with the concrete wall 16. Additionally, the detailing material acts as an electrical insulator and prevents stray leakage current paths. Typically, the above-ground end of the waterproofing membrane 5 is covered by a plastic or metal termination bar, which provides mechanical protection for the edge, and also serves as a cofferdam to hold the sealant material 60 when it is first applied. In the case of the electronic leak detection configuration, the termination bar would also provide the electrical connections to the ends of the metallic strips 79 in the electrically-conductive membrane layer 5 of the composite waterproofing membrane 1 for the positive connection point of the sensor device 53 and/or the positive connection lead of the LCR instrument of device 50 in FIGS. 10A and 11A, as well as hold an electrically conductive strip against the conductive primer 38 coating the concrete wall 16, which is where the negative connection of the LCR instrument in device 50 will be made, or serve as an alternate negative connection 56b for the current leakage device 53. Because of lightning strikes to buildings, which cause large amounts of electrical charge to travel to earth ground 59 through the structure's grounding system connections, high voltage surges can be present on the connection point to earth ground 56a; therefore, the current leakage device 53 would require protection from Electrical Fast Transient (EFT) that would arise due to the inductance of the structural grounding conductors.

FIG. 13 shows the block diagram for a generic electronic device that will perform the function of the leakage detector 53 shown in FIG. 12. Voltage source 61 applies a DC potential across the composite waterproofing membrane 1 of FIG. 1B at the negative 63 and positive 64 connection points through protection circuit 62, which blocks excess external voltage that may be induced into the composite waterproofing membrane 1 by an EFT from damaging the electronic detection components. Current sensing circuit 65 measures the current level leaking through the rubberized-asphalt membrane 4 of FIG. 1B, and signal conditioner 66 amplifies and scales the output from the current sensing circuit 65 and passes the signal through a filtering circuit to remove electronic noise before the signal is read by the data processing module 68. A transceiver device 69 allows the processing module 68 to transmit leakage data to a remote receiver and also receive commands from a remote transmitter. The device represented by FIG. 13 may take several different forms including but not limited to: a handheld off-the-self ohmmeter where the operator performs the functions of the remote reader and command unit; a current-leakage detector that transmits data over a dedicated or networked hardwired interface; a remotely linked data logger; a stand-alone battery-powered recorder; a wireless device that transmits and receives information through a radio frequency link; and/or a computerized data acquisition and control system.

FIG. 14A provides the schematic design for a prototype FIG. 13 device. A Melexis Semiconductor MLX90129 13.56 MHz RFID sensor tag integrated circuit 73 operating in passive RFID mode is used to realize the FIG. 13 functional elements 61, 66, 68 and 69, while the rest of the FIG. 13 functions are created using discrete passive electronic components. The device is connected to the waterproofing membrane 1 of FIG. 1B at the negative 71 and positive 70 connection points. The FIG. 13 protection circuit 62 is realized by FIG. 14A, item 72, where Transient Voltage Suppression (TVS) diode D2 provides positive voltage protection by clamping the voltage across the positive 70 and negative 71 connection points at approximately +5 VDC, and the Schottky barrier diode D1 provides reverse polarity voltage protection for positive voltage appearing at the negative 71 connection point by clamping voltage at approximately +0.2V. Resistors R2 and R3 provide current-limiting protection when either D1 or D2 are conducting current when suppressing voltage transients. Together, R2, R3, D1 and D2 will protect the MLX90129 RFID chip 73 against an 1000V surge appearing at either the positive 70 and negative 71 connection points and will offer protection up to 10 KV for very short durations (<100 μsec). Capacitors C1 and C2 with resistors R2 and R3 provide a modest level of higher frequency noise voltage suppression. When self-powered through the L1 antenna coil 74 by an external RFID reader device, the MLX90129 RFID chip 73 provides a regulated voltage from its SENSSUP1 pin of 3.0±0.1 VDC, which appears at the positive 70 connection point when no current is flowing through resistor R1. The MLX90129 RFID chip 73 VSS pin is referenced to the negative 71 connection point. Resistor R1 and the $R_M$ resistance of the rubberized-asphalt waterproofing membrane 4 in FIG. 12 form a voltage divider, which converts the leakage current through the rubberized-asphalt waterproofing membrane 4 to a voltage between differential input pins SENS1 and SENS2 of the MLX90129 RFID chip 73, where an internal signal conditioning circuit provides the voltage to the processing unit of the MLX90129 RFID chip 73.

FIG. 14B shows the voltage relationship between rubberized-asphalt waterproofing membrane 4 resistance and the Vsense (SENS1-SENSE2) DC voltage. Notice that at 200 Mohms (2.E+08 ohms) the Vsense voltage is approximately 2.28 VDC, and then drops rapidly when the rubberized-asphalt waterproofing membrane 4 resistance changes between 1 Mohm (1.E+06 ohms) and 1 Kohms (1.E+03 ohms) leveling off at approximately 0.25 VDC.

Because this device is intended to detect a leakage of water through the rubberized-asphalt waterproofing membrane 1, this response characteristic provides a satisfactory leak-detection output. The circuit configuration shown in FIG. 14A could be modified to provide more instrumentation-like ohmmeter capability, but at the expense of greater power draw from the L1 antenna coil 74, which would act to reduce the range from which the reader could obtain information. Using back scattering, the voltage value measured by the MLX90129 RFID chip 73 between its SENS1 and SENS2 pins, is clocked back to the external RFID reader device through the RF link as an encoded serial digital signal. The MLX90129 RFID chip 73 will respond to commands transmitted by the external RFID reader device and will transmit its unique ID, the voltage across SENSE1 and SENSE2, or the reading from an internal temperature sensor embedded within the chip. Because the MLX90129 uses anti-collision technology, multiple MLX90129 devices can be simultaneously interrogated by a single external RFID reader device.

When assigned to an improved waterproofing-panel assembly 15, the MLX90129 device associated with that particular panel will be identified by the unique ID code stored in the MLX90129 RFID chip 73 that provides a specific address for each panel 15 in a waterproofing installation, from which data can be acquired and recorded for future reference. In a final product configuration, the RFID sensor tag represented in FIG. 14A will be approximately the size and shape of a credit card, with the antenna 74 taking up most of the area. The MLX90129 RFID chip 73 operates in the 13.56 MHz Industrial Scientific and Medical (ISM) worldwide band and allows a remote reader to obtain data from a distance between 1 and 3 meters. With the configuration shown in FIG. 14A, and with the MLX90129 RFID chip 73 external memory and other non-essential devices either not installed or disabled, the range is closer to 3 meters with the proper antenna orientation. This will enable an operator with a hand-held reader with data-storage capability to walk beside the building foundation and gather waterproofing system verification data keyed by the RFID address which will be tied to waterproofing-panel 15 location. If a RFID leak sensor tag is used that operates in the ISM 902928 MHz frequency range, the range would be extended up to 12 meters, which would enable either a remotely located or several remotely located fixed position readers to be used for continuously gathering verification data from the waterproofing system.

Turning back to leak-detection capabilities for the under-slab installations depicted in FIGS. 8A-8C, which can also be applied to vertical installations as well, FIG. 8D plots the resistance of the rubberized-asphalt membrane 41, 48 as a function of the membrane surface area for three different membrane thicknesses. This relationship is calculated using Pouillet's Law, using values for Grace Bituthene 6000 EIM (W. R. Grace, 110-BIT-3E, Grace Waterproofing Systems: Bituthene® 6000 EIM, Singapore: W. R. Grace (S) Pte Ltd, 2014.), typical performance properties, where volume resistivity=$4\times10^{13}$ ohms-cm:

$$R_{membrane} \text{(cm}^2\text{)} = \text{(Resistivity} \times \text{thickness (cm))}/A_{membrane} \text{ (cm}^2\text{)} \quad \text{(Equation 3)}$$

Where:
$R_{membrane}$=Resistance of the rubberized-asphalt membrane
$A_{membrane}$=Surface area of the rubberized-asphalt membrane FIG. 8D depicts an embodiment of the rubberized-asphalt membrane (from FIGS. 8B and 8C) resistance characteristics, shown as a log-log relationship, for three different membrane thicknesses, and FIG. 8E depicts an embodiment of the rubberized-asphalt membrane (from FIGS. 8B and 8C) capacitance characteristics, also shown as a log-log relationship, for three different membrane thicknesses. It should be noted that the relationships depicted in FIGS. 8D and 8E apply for all installations; that is, both horizontal and vertical installations.

Stand-Alone Drain Panel with Intrinsic Leak Detection

In addition to membrane-applied or sheet-applied waterproofing barriers, there are also fluid-applied barriers used in the building-construction industry. Below-grade, fluid-applied (that is, pre-applied to the structural substrate, such as a concrete) waterproofing membranes make up a substantial portion of the commercial-construction market, especially in the case of residential structures. Examples would include, but are not limited to, the following:

Barricoat-R, manufactured by Carlisle Coatings & Waterproofing. This product is a roller-applied, water-based, asphalt emulsion modified with a blend of synthetic rubbers and special additives;

CCW-525 and CCW-525R, manufactured by Carlisle Coatings & Waterproofing. These products are liquid-applied, single-component, moisture-cured, elastomeric modified polyurethane that cures to form a flexible, monolithic, waterproof membrane on vertical or horizontal surfaces below grade;

CCW-703, manufactured by Carlisle Coatings & Waterproofing. This product is a liquid-applied membrane is a two-component polyurethane waterproofing system;

Procor®, manufactured by GCP Applied Technologies, Inc. This product is a two component, synthetic-rubber, cold-vulcanized, fluid-applied waterproofing membrane. It cures to form a resilient, monolithic, fully bonded elastomeric sheet; and TREMproof 201/60, manufactured by Tremco Inc. This product is a high-solids, VOC compliant, modified polyurethane waterproofing membrane.

To add a leak-detection capability to fluid-applied-type of below-grade waterproofing installation requires that the leak-detection mechanism be moved from the waterproofing membrane 1 to the drain panel 7.

Refer to FIGS. 15A-15C. In this particular embodiment, the improved waterproofing-panel assembly features a variation of the drain panel 13A that includes a filter fabric and anti-abrasion layer 10A and an added electrically-conducting layer 38B that provides the leak-detection capability. For purposes of this discussion, the posterior side of the integrated drain panel with intrinsic leak detection 13A is the surface that is applied to the substrate 16, and the anterior side of the integrated drain panel with intrinsic leak detection 13A is the surface that has the anti-abrasion layer 10A facing the earthen backfill. The structure substrate 16 is shown with a fluid-applied membrane 38A using a product selected from one of the examples listed above, or a similar commercially available product. The integrated drain panel with intrinsic leak detection 13A is applied to the fluid-applied membrane 38A using an appropriate adhesive (already discussed, supra) or as recommended by the fluid-applied membrane manufacturer.

FIG. 15B depicts an embodiment of a posterior-view section of the integrated drain panel with intrinsic leak detection 13A with the added electrically conducting layer 38B partially peeled away revealing the drain panel subassembly 13A. In variations, the electrically conducting layer 38B is made from a high-density polyethylene (HDPE), cross-laminated film backing with an electrically-conductive metal film or foil or wire mesh 38C bonded to the posterior side, henceforth referred to as the electrically-conductive metal element 38C. The electrically-conductive metal element 38C is intended to not extend all the way to the edge of the drain panel 13A; rather, the electrically-conductive metal element 38C is recessed back approximately 0.125 inches 38D. This feature serves to preserve electrical insulation at the edges of the integrated drain panel with intrinsic leak detection 13A. In variations, the HDPE cross-laminated film backing is bonded to the drain panel subassembly 13A with an industrial-grade chemically-compatible low-VOC adhesive 40. Similarly, in some applications, the electrically-conductive metal element 38C is bonded to the HDPE cross-laminated film backing with an industrial-grade chemically-compatible low VOC adhesive 40. It should be noted that if an integrated drain panel with intrinsic leak detection 13A is cut for fit in the field, then the cut edge must be detailed (covered) with a detailing sealant material 60 prior to assembly.

FIG. 15C depicts an embodiment of a cross-section-view of the integrated drain panel with intrinsic leak detection 13A with the added electrically conducting layer 38B containing an electrically-conductive metal element 38C. For reference, the drain panel subassembly 13A is shown with dimples 8 partially cut-away in this view. In variations, the core of the electrically conducting layer 38B is made from the HDPE cross-laminated film backing containing an electrically-conductive metal element 38C bonded to the posterior side. In some applications, the electrically-conductive metal element 38E is not intended to extend all the way to the edge of the drainage panel 13A; rather, the electrically-conductive metal element 38C is recessed back approximately 0.125 inches 38D. This feature serves to preserve electrical insulation at the edges of the integrated drain panel with intrinsic leak detection 13A. In more applications, the HDPE cross-laminated film backing core of the electrically conducting layer 38B is approximately 5 mils thick. Typically, the electrically-conductive metal element 38C is either a metallic film approximately 2 to 3 mils thick, or a 40 AWG metal wire mesh that is approximately 25% filled.

In embodiments, the electrical layer in the integrated drain panel with intrinsic leak detection 13A is electrically terminated in a similar manner to the termination of the waterproofing-panel assembly 15 in other embodiments, described supra, where it can be measured by external instruments such as an LCR meter and ohmmeter/multimeter. The electrical-leakage current, whether AC or DC, between the electrically conducting added layer 38B and the substrate 16 may be measured as an indicator of moisture infiltration through the waterproofing membrane 1. In variations, an installed specially-designed RFID tag (encapsulating the function of the instrumentation mentioned above) at the electrical termination, along with an RFID reader, may be used to allow remote sensing of the condition of the waterproofing installation to take place as described for the waterproofing-panel assembly 15 in other embodiments, supra. The side-to-side and end-to-end joining of the integrated drain panels with intrinsic leak detection 13A is identical to that described for the waterproofing-panel assembly 15 already described, supra.

It should be recognized that those skilled in the art of electronic design will be able to create many different leakage detection circuit sensor configurations with a variety of remote readers that will provide the functionality of the device shown in FIG. 13. Furthermore, it would also be possible to combine the functions of the frequency optimized LCR device described in FIG. 11A with the leak detection device of FIG. 13.

IV. A Method for Manufacturing and Installing an Improved Building Foundation Waterproofing and Drainage System With Intrinsic Leak Detection Capabilities This Section IV is directed to an improved process for manufacturing and installing an improved waterproofing and drainage system with intrinsic leak detection for use in building structures, such as vertical and horizontal foundational structures that are disposed below ground, the improved system depicted in FIGS. 1A though 15C and further described in Section III, supra, the current state of the art process being depicted in FIGS. 16A-16B, and the improved process being depicted in FIGS. 17A-17B.

Below-grade commercial waterproofing systems, as represented by the current-art installations currently available in the market, are engineered to protect below-ground structures and their contents from the infiltration of ground water. These prior-art waterproofing systems, however, contain potential failure modes that arise through the system manufacturing and configuration, as well as through the installation process. These failure modes can be identified and the associated effects quantified using a process Failure Modes and Effects Analysis (FMEA).

Typical Prior-Art Fabrication-and-Installation Process

The typical example of the current state of the art for the installation of existing below-ground waterproofing systems for buildings is depicted in FIGS. 16A-16B, which is followed for most current-art systems. The overall current-art process is outlined in a flow diagram in FIG. 16A, while the key process steps in FIG. 16A are diagrammed in FIG. 16B (a corner fragment is shown, with the drawing not to scale). Installation of waterproofing on an existing-vertical-foundation-wall case applies for this example (i.e., not blindside or under-slab installation cases). Table 2, below, describes the process steps in a typical current-art configuration and installation:

TABLE 2

Current-Art Process-Step Description (See FIGS. 15A-15B)

| ID | Process Step | Description |
|----|--------------|-------------|
| A | Start Installation | The Architectural Specification N (unique for each construction project) defines the waterproofing materials and general installation requirements. Contractors for installation are chosen based on the contractor's certifications O and experience. |
| B | Prepare Substrate in Field | Level installation surfaces, remove rough spots that could damage the membrane. |
| C | Prime Substrate in Field | Apply primer coating (surface is enhanced for optimal membrane adhesion). |
| D | Install Membrane in Field | Remove membrane release liner and apply membrane to the substrate. |
| E | Detail Membrane as required | Edges, joints, and seams are filled using sealant. |
| L | Inspection On-Site | Waterproofing system manufacturer's on-site representative ensures: The recommended installation process has been followed by the contractor (warranty certification requirement). The membrane installation meets quality requirements. A sample test (e.g. pull test) may be required (as defined by the specification). |
| F | Apply Adhesive | Adhesive is applied to the membrane. |
| G | Install Drainage Board | The drainage board is affixed to the membrane with the adhesive. |
| H | Verify Installation | Verification (prior to backfilling): The manufacturer's representative verifies that the recommended drainage board installation process has been followed by the contractor (warranty certification requirement) and the system installation meets quality requirements (good drainage board adhesion, proper overlaps, no tears in filter fabric, etc.) using visual methods and audit of construction records. The contractor attempts to verify that the system installation will not leak; options for testing the leak-proof integrity are limited due to the configuration of the system (e.g. vertical installation instead of horizontal). Often, the quality can only be assessed qualitatively, primarily through visual inspection and with onsite audits during the installation phase. |
| I | On-Site Inspection | On-site inspection; test for warranty. |
| J | Bury Installation | Earthen backfill is used to bury the installation below ground. |
| K | Installation Complete | The waterproofing system manufacturer's warranty period begins. |
| M | On-Site Inspection | On-site inspection; test for warranty. |

Besides being inefficient, the above current-art fabrication-and-installation process discussed in Table 2 involves many in-filed steps that further introduce opportunities for the introduction of installation errors/defects that may not be detected, if at all, until much time, materials, and efforts have been expended. In the event of the detection of such errors/defects, additional time-consuming and expensive in-field remediation must then be initiated.

Improved Fabrication-and-Installation Process Using FMEA Principles

A Failure Mode and Effects Analysis (FMEA) is a systematic group of activities intended to:

Identify and evaluate the potential modes of failure of a product and/or process, and the associated effects which result from these failures;

Provide an estimation for the probability of the failure occurrence and the severity of the failure effect;

Identify actions that could eliminate or reduce the occurrence of the failure modes and/or mitigate the failure effects; and Document the design and/or process and how the product or process can be improved.

FMEA is a standard tool used by engineers during design analysis and manufacturing process development; the FMEA discipline was an innovation of the aerospace industry in the mid-1960s.

Appendix A provides a formal process FMEA worksheet, which is separated into two tables, each associated with the same general process steps. The potential failure modes of the process described above in FIGS. 16A-16B, and Table 2, are listed on each line of the FMEA worksheet; the FMEA steps are contained in the columns from left to right (in their order of progression). The key for each category (Severity $S_o$, Occurrence $P_o$, and Detectability $Pd_o$) appear below the FMEA tables shown in Appendix A. The reduced number of category levels (five instead of 10) follow the approach typically used for medical-devices and are favored for a more qualitative FMEA (i.e., when actual process information, such as hard failure rates for each operation, are not available).

A brief description of the FMEA is provided in the bulleted list below. The information from the first entry line of the FMEA (i.e., Potential Failure Mode B.1) is provided after each FMEA step description as an example.

ID/Process Step: Each failure mode is assigned an identification (e.g. "B.1"=Failure Mode 1, of Process Step B), and that process step is listed (e.g., "Prep Substrate").

Potential Failure Mode: The potential failure mode appears (e.g., "Void"=a depression in the surface of the substrate).

Potential Failure Effect: The potential effect caused by the failure mode is given (e.g., "Membrane Non-Adhesion"=because of the depression in the substrate, the membrane adhesive will not function as intended).

Severity $S_i$ (SEV): The initial assessment for the severity of the potential failure effect (e.g., "3"=is a marginal severity category, where the failure could result in damage to structural contents, compromise structural usage, and cause immitigable environmental damage

APPENDIX A
FMEA WORKSHEET
(Sheet 1 of 4)

FMEA Type / Phase: Process / Field Installation
Part or Process: Below-Grade Waterproofing Installation
Design / Manufacturing Responsibility: Supplier / General Contractor
Product Name: Below-Grade Waterproofing System
Product Model: General Commercial Construction Materials
Product P/N: Various
FMEA Date (Orig.): 20151106     Rev.: 20170106
References: U.S. Patent Application Nos. U.S. 62/148,312

| ID / Process Step | | Potential Failure Mode | Potential Failure Effect | Severity $S_i$ (SEV) | Potential Cause(s) of Failure | Occurrence $P_i$ (OCC) | Current Controls |
|---|---|---|---|---|---|---|---|
| B.1 | Prep substrate | Small area void | Membrane Non-adhesion | 3 | Improper/poor method by contractor | 3 | Inspection |
| B.2 | Prep substrate | Sharp elevation | Membrane damage | 3 | Improper/poor method by contractor | 3 | Inspection |
| C.1 | Apply primer | Non-adhesion | Membrane Non-adhesion | 3 | Substrate surface contamination (e.g. oil) | 3 | Process requirement |
| D.1 | Install membrane | Fish mouth/wrinkle | Leakage | 3 | Improper/poor method by contractor, membrane flex | 3 | Inspection |
| D.2 | Install membrane | Non-adhesion | Leakage | 3 | Contamination of adhesive backing (windblown material, or FOD = Foreign Object Debris) | 3 | Inspection |
| D.3 | Install membrane | Large area void | Leakage | 3 | Uneven substrate, Improper/poor method by contractor | 3 | Inspection |
| D.4 | Install membrane | Material compromise | Leakage | 3 | UV damage, excessive exposure before dainboard installation | 2 | Process requirement |
| E.1 | Detail membrane | Non-seal | Leakage | 3 | Improper/poor method by contractor | 3 | Inspection |
| F.1 | Apply adhesive | Non-adhesion | poor drainboard adhesion, compromised drainage | 3 | Membrane surface contamination (e.g. oils, greases, FOD) | 3 | Inspection |
| F.2 | Apply | Contamination | poor | 3 | Wind-blown | 3 | Inspection |

APPENDIX A
FMEA WORKSHEET
(Sheet 2 of 4)

| ID / Process Step | Potential Failure Mode | Potential Failure Effect | Severity $S_i$ (SEV) | Potential Cause(s) of Failure | Occurrence $P_i$ (OCC) | Current Controls |
|---|---|---|---|---|---|---|
| | adhesive | drainboard adhesion, compromised drainage | | contaminants (FOD) in adhesive | | |
| G.1 | Install drainage board | Poor adhesion | Compromised drainage | 3 | Dried out adhesive, contractor waited too long before drainboard installation | 3 | Process requirement |
| H.1 | Verification | Un-detected defect(s) | Leakage | 3 | Process errors by contractor, material defects | 3 | Inspection |
| I.1 | Backfill | Filter damage | Clogged drainage channels from soil infiltration, build-up of hydrostatic pressure | 3 | Sharp object/debris in backfill | 3 | None |
| W.1 | Warranty Period | Leakage | Water in building | 4 | Latent undetected defect | 3 | None |
| W.2 | Post Warranty | Leakage | Water in building | 4 | Aging of installation and materials over the life of the building | 5 | None |

| D / Process Step | | Potential Failure Mode | Detect $Pd_i$ (DET) | $RPN_i$ | Risk Mitigation | Action Results | | | | |
|---|---|---|---|---|---|---|---|---|---|---|
| | | | | | | Action for Mitigation | $S_f$ (SEV) | $P_f$ (OCC) | $Pd_f$ (DET) | $RPN_f$ |
| B.1 | Prep substrate | Small area void | 1 | 9 | | Golding modification | 3 | 3 | 1 | 9 |
| B.2 | Prep substrate | Sharp elevation | 1 | 9 | | Golding modification | 3 | 3 | 1 | 9 |
| C.1 | Apply primer | Non-adhesion | 1 | 9 | | Golding modification | 3 | 3 | 1 | 9 |
| D.1 | Install membrane | Fish mouth/wrinkle | 2 | 18 | Factory-Integrated Panel, Intrinsic Leak Detection | Golding modification | 1 | 2 | 3 | 6 |
| D.2 | Install membrane | Non-adhesion | 2 | 18 | Factory-Integrated | Golding modification | 1 | 3 | 3 | 9 |

APPENDIX A
FMEA WORKSHEET
(Sheet 3 of 4)

| D / Process Step | | Potential Failure Mode | Detect Pd$_i$ (DET) | RPN$_i$ | Risk Mitigation | Action Results | | | | |
|---|---|---|---|---|---|---|---|---|---|---|
| | | | | | | Action for Mitigation | S$_f$ (SEV) | P$_f$ (OCC) | Pd$_f$ (DET) | RPN$_f$ |
| | | | | | Panel, Intrinsic Leak Detection | | | | | |
| D.3 | Install membrane | Large area void | 2 | 18 | Factory-Integrated Panel, Intrinsic Leak Detection | Golding modification | 1 | 3 | 3 | 9 |
| D.4 | Install membrane | Material compromise | 1 | 6 | | Golding modification | 1 | 1 | 1 | 1 |
| E.1 | Detail membrane | Non-seal | 3 | 27 | Factory-produced field joints, Intrinsic Leak Detection | Golding modification | 1 | 2 | 3 | 6 |
| F.1 | Apply adhesive | Non-adhesion | 2 | 18 | Factory-Integrated Panel, Intrinsic Leak Detection | Golding modification | 1 | 1 | 1 | 1 |
| F.2 | Apply adhesive | Contamination | 2 | 18 | Factory-Integrated Panel, Intrinsic Leak Detection | Golding modification | 1 | 1 | 1 | 1 |
| G.1 | Install drainage board | Poor adhesion | 2 | 18 | Factory-Integrated Panel, Intrinsic Leak Detection | Golding modification | 1 | 1 | 1 | 1 |
| H.1 | Verification | Un-detected defect(s) | 5 | 45 | Intrinsic Install Verification and Leak Detection | Golding modification | 1 | 1 | 1 | 1 |
| I.1 | Backfill | Filter damage | 5 | 45 | Integrated Anti-abrasion Layer | Golding modification | 2 | 2 | 1 | 4 |
| W.1 | Warranty Period | Leakage | 5 | 60 | Intrinsic Leak Detection, Preemptive Repair | Golding modification | 1 | 3 | 1 | 3 |

APPENDIX A
FMEA WORKSHEET
(Sheet 4 of 4)

| D / Process Step | | Potential Failure Mode | Detect $Pd_i$ (DET) | $RPN_i$ | Risk Mitigation | Action Results | | | | |
|---|---|---|---|---|---|---|---|---|---|---|
| | | | | | | Action for Mitigation | $S_f$ (SEV) | $P_f$ (OCC) | $Pd_f$ (DET) | $RPN_f$ |
| W.2 | Post Warranty | Leakage | 5 | 100 | Intrinsic Leak Detection, Preemptive Repair | Golding modification | 2 | 5 | 1 | 10 |

$S_o$ SEVERITY  Failure effect severity categories (2 to 5) adapted from MIL-STD-882D [4]

1. Nuisance: The failure does not affect product quality, but is inconvenient to the user/customer
2. Negligible: (increased costs due to rework, construction delays and post-installation repairs)
3. Marginal: The failure could result in minimal compromise to structural usage, minor building
4. Critical: environmental damage (dampness)
5. Catastrophic: The failure could result in damage to structural contents, compromise structural usage, mitigatable environmental damage (internal wetness, high humidity)
The failure could result in potentially permanent damage to structural contents, structural non-usage, reversible environmental damage (standing water, toxic mold formation)
The failure causes permanent damage to structural contents, structural damage or failure, severe and irreversible environmental damage (toxic mold spread/contamination)

$Pd_o$ DETECTION  The relative ease of detecting the failure (based on a defect making it through the installation/verification process, and being delivered to the structural customer)

1. Very High:
2. High: Controls will almost always certainly detect the existence of the defect (i.e., the process
3. Moderate: automatically ensures detection)
4. Low: Controls have a good chance of detecting the existence of the defect
5. Very Low: Controls may detect the existence of the defect
Controls have a poor chance of detecting the defect
Controls probably will not or cannot detect the existence of the defect $P_o$ OCCURANCE  The relative likelihood that the failure will occur; from historical data / observation 1. Very Low: Less than 1 in 2e-5 => +/- 4 sigma
2. Low: Up to 1 in 1000 => +/- 3 sigma
3. Medium: Up to 1 in 80
4. High: Up to 1 in 20
5. Very High: More than 1 in 20

RPN  Risk Priority Number = $S \times P \times P_d$ (1 to 125)

≤ 10  Acceptable Risk
11 to 50  Risk must be mitigated
> 50  Risk is unacceptable